US009637748B2

(12) United States Patent
Johnson et al.

(10) Patent No.: US 9,637,748 B2
(45) Date of Patent: May 2, 2017

(54) CONJUGATIVE PLASMIDS AND METHODS OF USE THEREOF

(71) Applicant: Wisconsin Alumni Research Foundation, Madison, WI (US)

(72) Inventors: Eric A. Johnson, Madison, WI (US); Kristin M. Marshall, Madison, WI (US); Marite Bradshaw, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 14/096,584

(22) Filed: Dec. 4, 2013

(65) Prior Publication Data

US 2014/0106458 A1     Apr. 17, 2014

Related U.S. Application Data

(63) Continuation of application No. 12/905,592, filed on Oct. 15, 2010, now abandoned.

(60) Provisional application No. 61/252,029, filed on Oct. 15, 2009.

(51) Int. Cl.
C12N 15/74     (2006.01)

(52) U.S. Cl.
CPC ................................ *C12N 15/74* (2013.01)

(58) Field of Classification Search
None
See application file for complete search history.

(56) References Cited

U.S. PATENT DOCUMENTS 5,955,368 A     9/1999 Johnson et al.

FOREIGN PATENT DOCUMENTS

WO     WO2009006281 A1     1/2009

OTHER PUBLICATIONS

Arndt, et al., A Structural Perspective of the Sequence Variability Within Botulinum Neurotoxin Subtypes A1-A4, J. Mol. Biol., 2006, 362(4):733-742.
Aureli, et al., Two Cases of Type E Infant Botulism Caused by Neurotoxigenic Clostridium Butyricum in Italy, Journal of Infectious Diseases, 1986, 154(2)207-211.
Bannam, et al., Functional Identification of Conjugation and Replication Regions of the Tetracycline Resistance Plasmid pCW3 from Clostridium Perfringens, Journal of Bacteriology, 2006, 188(13):4942-4951.
Beverley, Characterization of the 'Unusual' Mobility of Large Circular DNAs in Pulsed Field-Gradient Electrophoresis, Nucleic Acids Research, 1988, 16(3):925-939.
Blaiotta, et al., Conditions for Conjugative Transposon Transfer in Lactococcus Lactis, Letters in Applied Microbiology, 2000, 31:343-348.
Bradshaw, et al., Regulation of Neurotoxin Complex Expression in Clostridium Botulinum Strains 62A, Hall A-hyper, and NCTC 2916, Anaerobe, 2004, 10:321-333.
Brynestad, et al., Enterotoxin Plasmid from Clostridium Perfringens is Conjugative, Infection and Immunity, 2001, 69(5):3483-3487.
Carter, et al., Independent Evolution of Neurotoxin and Flagellar Genetic Loci in Proteolytic Clostridium Botulinum, BMC Genomics, 2009, 10:115, pp. 1-18.
Darling, et al., Mauve: Multiple Alignment of Conserved Genomic Sequence With Rearrangements, Genome Research, 2004, 14:1394-1403.
Dineen, et al., Cloning, Nucleotide Sequence, and Expression of the Gene Encoding the Bacteriocin Boticin B From Clostridium Botulinum Strain 213B, Applied and Environmental Microbiology, 2000, 66(12):5480-5483.
Dover, et al., Letters to the Editor—Novel Clostridium Botulinum Toxin Gene Arrangement with Subtype A5 and Partial Subtype B3 Botulinum Neurotoxin Genes, Journal of Clinical Microbiology, 2009, 47(7)2349-2350.
East, et al., Organization and Phylogenetic Interrelationships of Genes Encoding Components of the Botulinum Toxin Complex in Proteolytic Clostridium Botulinum Types A, B and F: Evidence of Chimeric Sequences in the Gene Encoding the Nontoxic Nonhemagglutinin Component, International Journal of Systematic Bacteriology, 1996, 46(4):1105-1112.
Eklund, et al., Evidence for Plasmid-Mediated Toxin and Bacteriocin Production in Clostridium Botulinum Type G, Applied and Environmental Microbiology, 1988, 54(6):1405-1408.
Eklund, et al., Outgrowth and Toxin Production of Nonproteolytic Type B Clostridium Botulinum at 3.3 to 5.6 C, Journal of Bacteriology, 1967, 93(4):1461-1462.
Franciosa, et al., Differentiation of the Gene Clusters Encoding Botulinum Neurotoxin Type A Complexes in Clostridium Botulinum Type A, Ab, and A(B) Strains, Applied and Environmental Microbiology, 2004, 70(12):7192-7199.
Franciosa, et al., Evidence that Plasmid-Borne Botulinum Neurotoxin Type B Genes Are Widespread Among Clostridium Botulinum Serotype B Strains, PLoS One, 2009, 4(3):e4829, pp. 1-9.

(Continued)

*Primary Examiner* — Nancy Treptow
(74) *Attorney, Agent, or Firm* — Quarles & Brady, LLP

(57) ABSTRACT

The present invention provides novel *C. botulinum* conjugatively transmissible plasmids and methods of use thereof. Specifically, described herein are novel, conjugatively transmissible clostridial plasmids which are capable of being transferred among and between clostridial species. The novel plasmids of the present invention therefore permits the delivery of heterologous clostridial genes into a clostridial host, such as *C. botulinum*, and the expression of genes of interest in that host, including clostridial toxins and the nontoxigenic components of the toxin complex, toxin fragments, or antigenic portions thereof, in a way both that ensures abundant expression and facilitates purification. Furthermore, toxins with altered structures, chimeric, hybrid toxins, and other toxin derivatives valuable in medicine could be synthesized in this system.

14 Claims, 22 Drawing Sheets

(56) References Cited

OTHER PUBLICATIONS

Gimenez, et al., New Strains of Clostridium Botulinum Subtype Af, Zbl. Bakt. Hyg., I. Abt. Orig. A, 1978, 240:215-220.
Gimenez, et al., Identification of Strain B 657 of Clostridium Botulinum, Revista Argentina de Microbiologia, 1983, 15(1):51-55.
Gimenez, et al., Characterization of the Neurotoxin Isolated from a Clostridium Baratii Strain Implicated in Infant Botulism, Infection and Immunity, 1992, 60(2):518-522.
Hall, et al., Isolation of an Organism Resembling Clostridium Barati Which Produces Type F Botulinal Toxin from an Infant With Botulism, Journal of Clinical Microbiology, 1985, 21(4):654-655.
Harvey, et al., Botulism Due to Clostridium Baratti Type F Toxin, Journal of Clinical Microbiology, 2002, 40 (6):2260-2262.
Hatheway, Toxigenic Clostridia, Clinical Microbiology Reviews, 1990, 3(1):66-98.
Hatheway, et al., Examination of Feces and Serum for Diagnosis of Infant Botulism in 336 Patients, Journal of Clinical Microbiology, 1987, 25(12):2334-2338.
Hatheway, et al., Atypical Toxin Variant of Clostridium Botulinum Type B Associated with Infant Botulism, Journal of Clinical Microbiology, 1981, 14(6):607-611.
Hauser, et al., Plasmid Localization of a Type E Botulinal Neurotoxin Gene Homologue in Toxigenic Clostridium Butyricum Strains, and Absence of This Gene in Non-Toxigenic C. Butyricium Strains, FEMS Microbiology Letters, 1992, 99:251-256.
Heap, et al., The ClosTron: Mutagenesis in Clostridium Refined and Streamlined, Journal of Microbiological Methods, 2010, 80:49-55.
Heap, et al., A Modular System for Clostridium Shuttle Plasmids, Journal of Microbiological Methods, 2009, 78:79-85.
Heap, et al., The ClosTron: A Universal Gene Knock-Out System for the Genus *Clostridium*, Journal of Microbiological Methods, 2007, 70:452-464.
Hill, et al., Genetic Diversity Among Botulinum Neurotoxin-Producing Clostridial Strains, Journal of Bacteriology, 2007, 189(3):818-832.
Hill, et al., Recombination and Insertion Events Involving the Botulinum Neurotoxin Complex Genes in Clostridium Botulinum Types A, B, E and F and Clostridium Butyricum Type E Strains, BMC Biology, 2009, 7:66, pp. 1-18.
Hughes, et al., Epsilon-Toxin Plasmids of Clostridium Perfringens Type D Are Conjugative, Journal of Bacteriology, 2007, 189(21):7531-7538.
Hutson, et al., Genetic Characterization of Clostridium Botulinum Type A Containing Silent Type B Neurotoxin Gene Sequences, Journal of Biological Chemistry, 1996, 271:10786-10792.
Jacobson, et al., Phylogenetic Analysis of Clostridium Botulinum Type A by Multi-Locus Sequence Typing, Microbiology, 2008, 154(Pt 8):2408-2415.
Johnson, et al., Characterization of Clostridium Botulinum Strains Associated with an Infant Botulism Case in the United Kingdom, Journal of Clinical Microbiology, 2005, 43(6):2602-2607.
Johnson, et al., Characterization of Neurotoxin Mutants in Clostridium Botulinum Type A., Clinical Infectious Diseases, 1997, 25(Suppl 2):S168-S170.
Jovita, et al., Gene Organization and Sequence Determination of the Two Botulinum Neurotoxin Gene Clusters in Clostridium Botulinum Type A(B) Strain NCTC 2916, Current Microbiology, 1998, 36:226-231.
Lin, et al., Transposon Tn916 Mutagenesis in Clostridium Botulinum, Applied and Environmental Microbiology, 1991, 57(10):2946-2950.
Lynt, et al., Differences and Similarities Among Proteolytic and Nonproteolytic Strains of Clostridium Botulinum Types A, B, E and F: A Review, Journal of Food Protection, 1982, 45(5):466-474.
Marshall, et al., Conjugative Botulinum Neurotoxin-Encoding Plasmids in Clostridium Botulinum, PLoS One, 2010, 5(6):e11087, pp. 1-15.
Marshall, et al., Plasmid Encoded Neurotoxin Genes in Clostridium Botulinum Serotype A Subtypes, Biochemical and Biophysical Research Communications, 2007, 361:49-54.
McCroskey, et al., Characterization of an Organism That Produces Type E Botulinal Toxin But Which Resembles Clostridium Butyricum from the Feces of an Infant with Type E Botulism, Journal of Clinical Microbiology, 1986, 23(1):201-202.
McCroskey, et al., Type F Botulism Due to Neurotoxigenic Clostridium Baratii from an Unknown Source in an Adult, Journal of Clinical Microbiology, 1991, 29(11):2618-2620.
Neve, et al., Conjugal Transfer and Characterization of Bacteriocin Plasmids in Group N (Lactic Acid) Streptococci, Journal of Bacteriology, 1984, 157(3):833-838.
Parsons, et al., TcpA, an FtsK/SpoIIIE Homolog, Is Essential for Transfer of the Conjugative Plasmid pCW3 in Clostridium Perfringens, Journal of Bacteriology, 2007, 189(21):7782-7790.
Peck, Biology and Genomic Analysis of Clostridium Botulinum, Advances in Microbial Physiology, 2009, 55:183-265,320.
Raphael, et al., Genetic Homogeneity of Clostridium Botulinum Type A1 Strains with Unique Toxin Gene Clusters, Applied and Environmental Microbiology, 2008, 74(14):4390-4397.
Rood, et al., Identification of a Transferable Tetracycline Resistance Plasmid (pCW3) from Clostridium Perfringens, Plasmid, 1978, 1:563-570.
Rood, Virulence Plasmids of Spore-Forming Bacteria, Plasmid Biology, Chapter 19, ASM Press, Washington D.C., 2004, pp. 413-422.
Sakaguchi, et al., The Genome Sequence of Clostridium Botulinum Type C Neurotoxin-Converting Phage and the Molecular Mechanisms of Unstable Lysogeny, Proc. Natl. Acad. Sci., 2005, 102(48):17472-17477.
Sambrook, et al., Molecular Cloning—A Laboratory Manual, 3rd Ed., 2001, Cold Spring Harbor Laboratory Press, Cold Spring Harbor, NY.
Santos-Buelga, et al., Characterization of the Genes Encoding the Botulinum Neurotoxin Complex in a Strain of Clostridium Botulinum Producing Type B and F Neurotoxins, Current Microbiology, 1998, 37:312-318.
Sayeed, et al., Virulence Plasmid Diversity in Clostridium Perfringens Type D Isolates, Infection and Immunity, 2007, 75(5):2391-2398.
Schantz, et al., Properties and Use of Botulinum Toxin and Other Microbial Neurotoxins in Medicine, Microbiological Reviews, 1992, 56(1):80-99.
Scott, et al., Cryptic Plasmids in Clostridium Botulinum and C. Botulinum-Like Organisms, FEMS Microbiology Letters, 1978, 4:55-58.
Sebaihia, et al., Genome Sequence of a Proteolytic (Group I) Clostridium Botulinum Strain Hall A and Comparative Analysis of the Clostridial Genomes, Genome Research, 2007, 17:1082-1092.
Smedley, et al., The Enteric Toxins of Clostridium Perfringens, Reviews of Physiology, Biochemistry and Pharmacology, 2004, 152:183-204.
Smith, et al., Sequence Variation within Botulinum Neurotoxin Serotypes Impacts Antibody Binding and Neutralization, Infection and Immunity, 2005, 73(9):5450-5457.
Smith, et al., Analysis of the Neurotoxin Complex Genes in Clostridium Botulinum A1-A4 and B1 Strains: BoNT/A3, /Ba4 and /B1 Clusters Are Located Within Plasmids, PLoS One, 2007, 12:e1271, pp. 1-10.
Strom, et al., Plasmids in Clostridium Botulinum and Related Clostridium Species, Applied and Environmental Microbiology, 1984, 48(5):956-963.
Umeda, et al., Genetic Characterization of Clostridium Botulinum Associated with Type B Infant Botulism in Japan, Journal of Clinical Microbiology, 2009, 47(9):2720-2728.
Wang, et al., Genetic Analysis of Type E Botulinum Toxin-Producing Clostridium Butyricum Strains, Applied and Environmental Microbiology, 2000, 66(11):4992-4997.
Zhou, et al., Transfer of Neurotoxigenicity from Clostridium Butyricum to a Nontoxigenic Clostridium Botulinum Type E-Like Strain, Applied and Environmental Microbiology, 1993, 59(11):3825-3831.
Zhou, et al., The Genes for the Clostridium Botulinum Type G Toxin Complex Are on a Plasmid, Infection and Immunity, 1995, 63(5):2087-2091.
PCT International Search Report and Written Opinion, PCT/US2010/052863, Feb. 4, 2011.

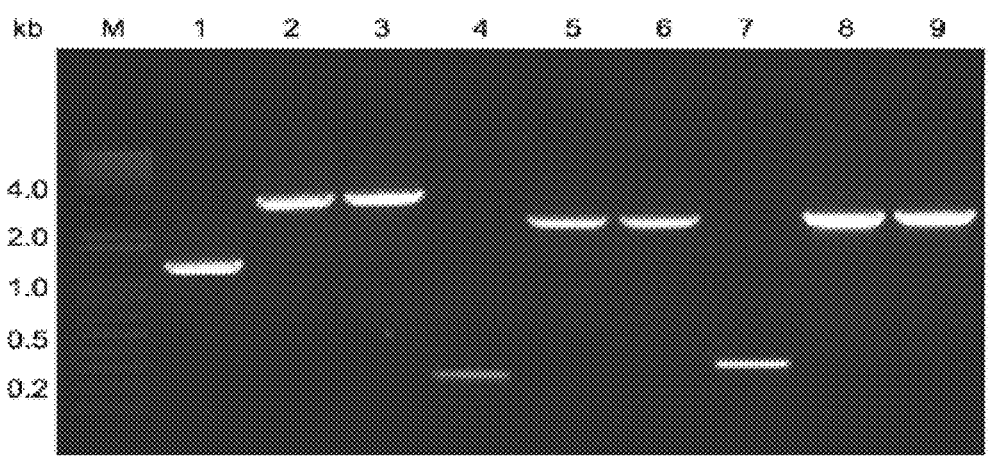
Figure 1
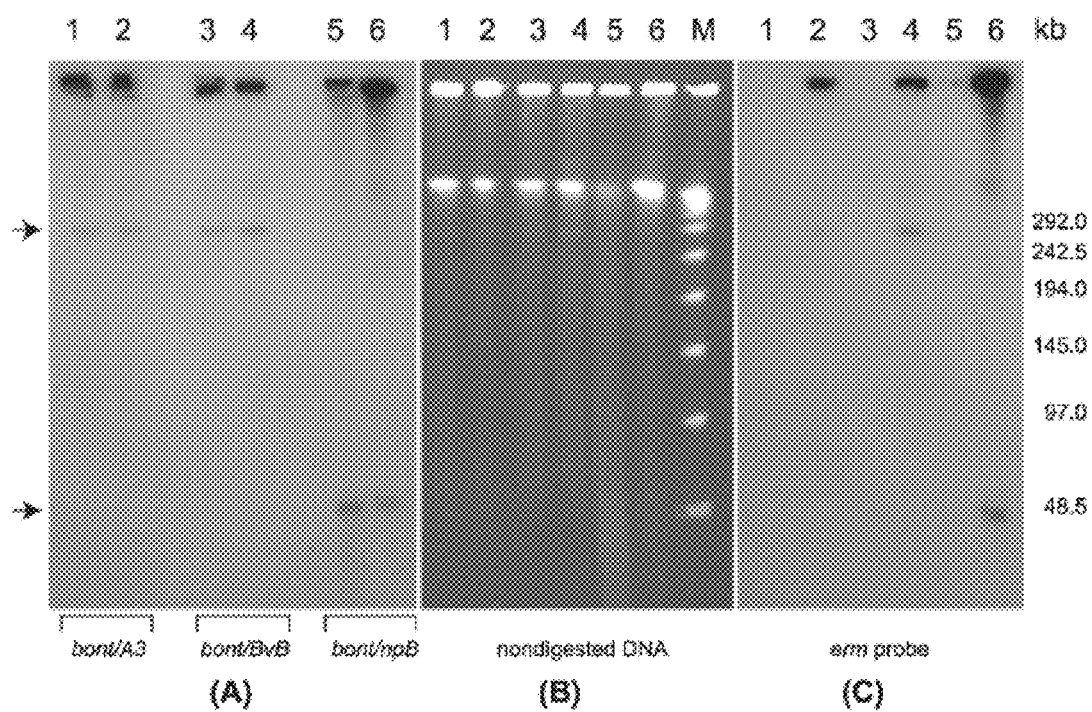
Figure 2 - A-C

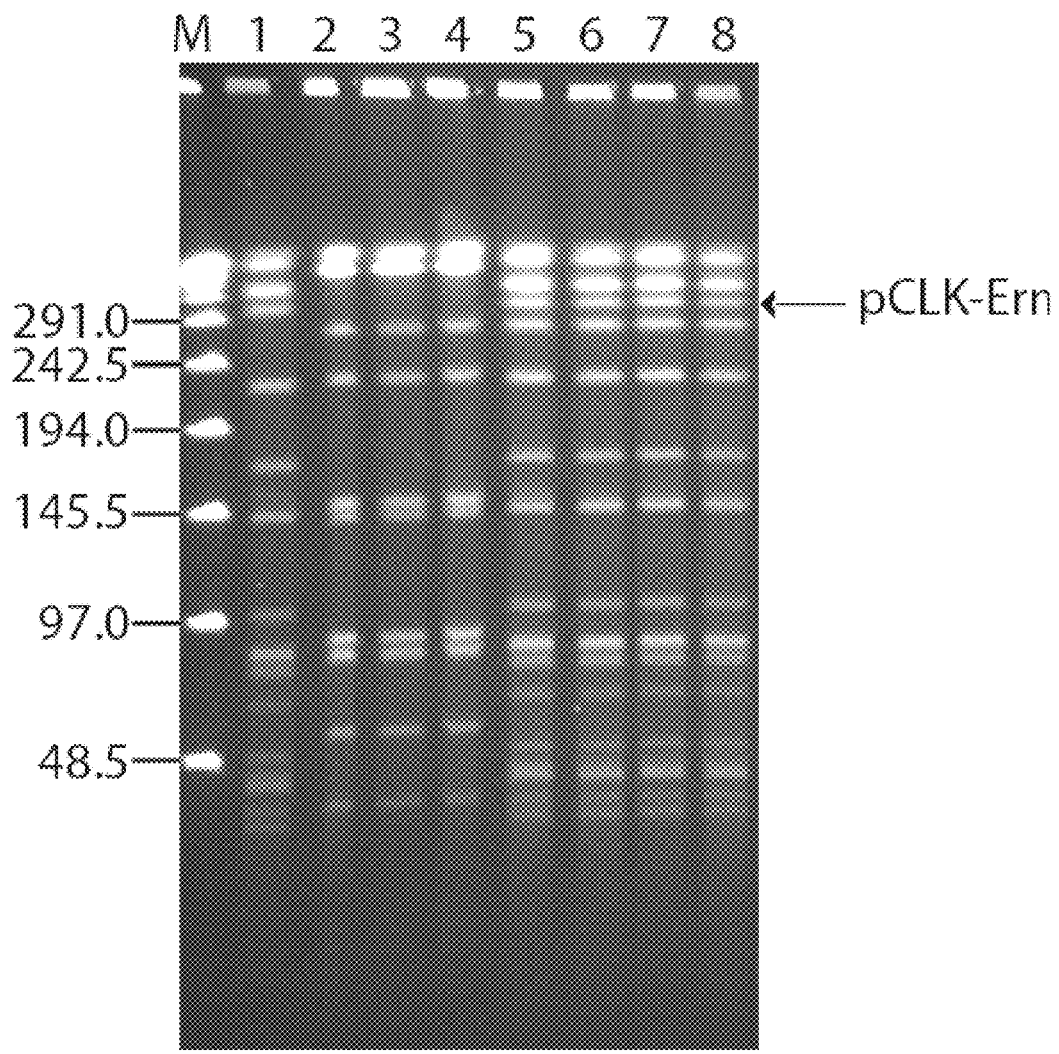
Figure 3 - A

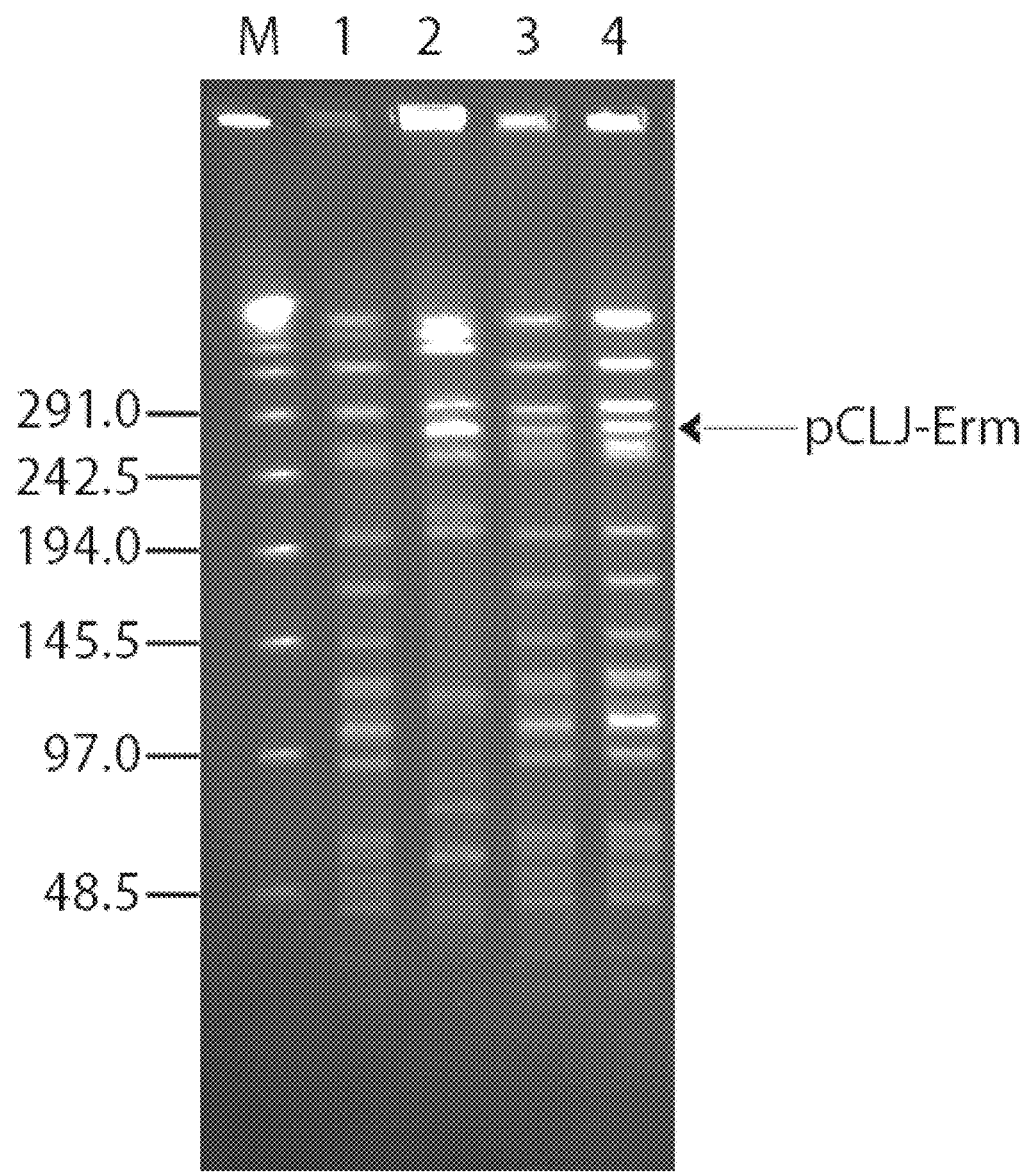
Figure 3 - B

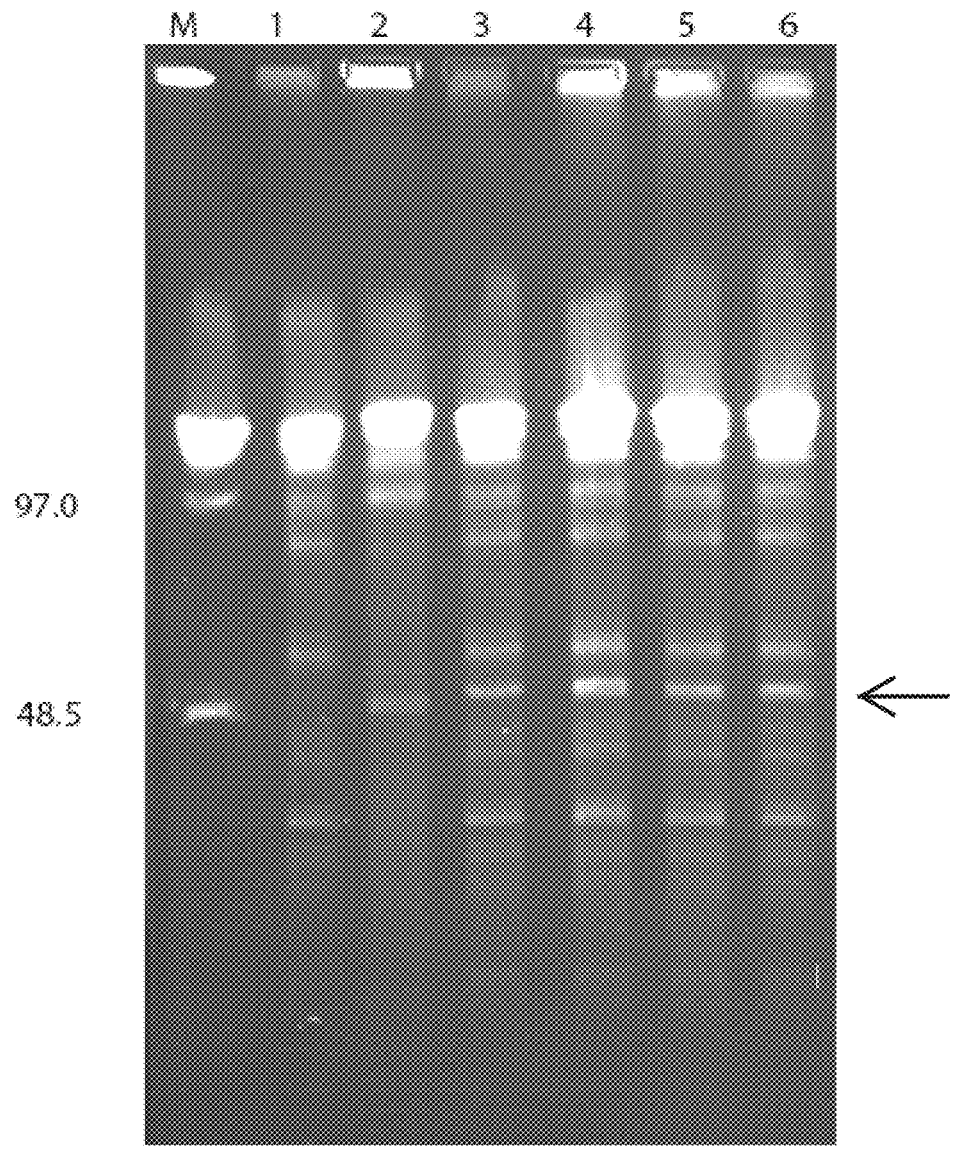
Figure 3 - C

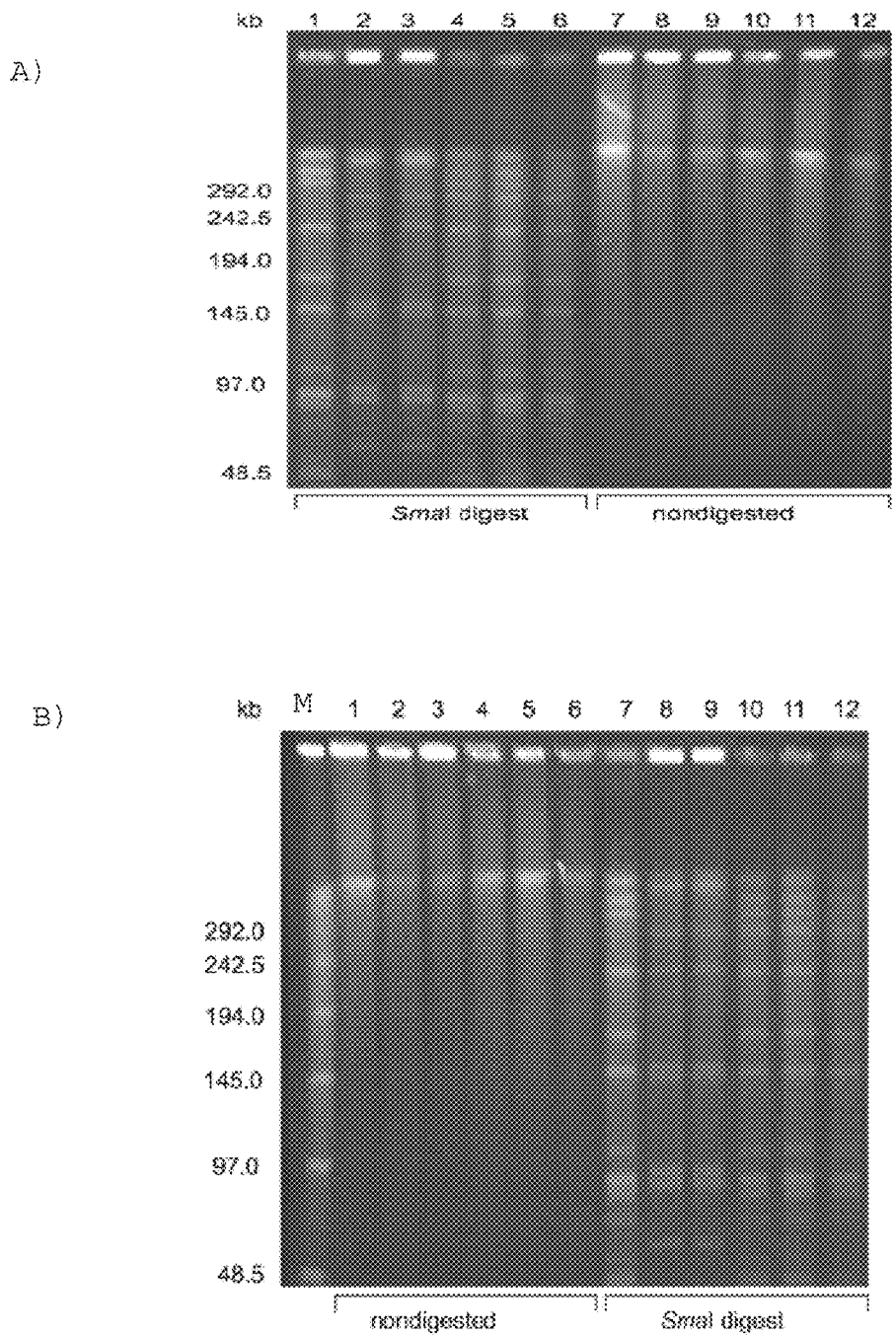
Figure 4 - A-B

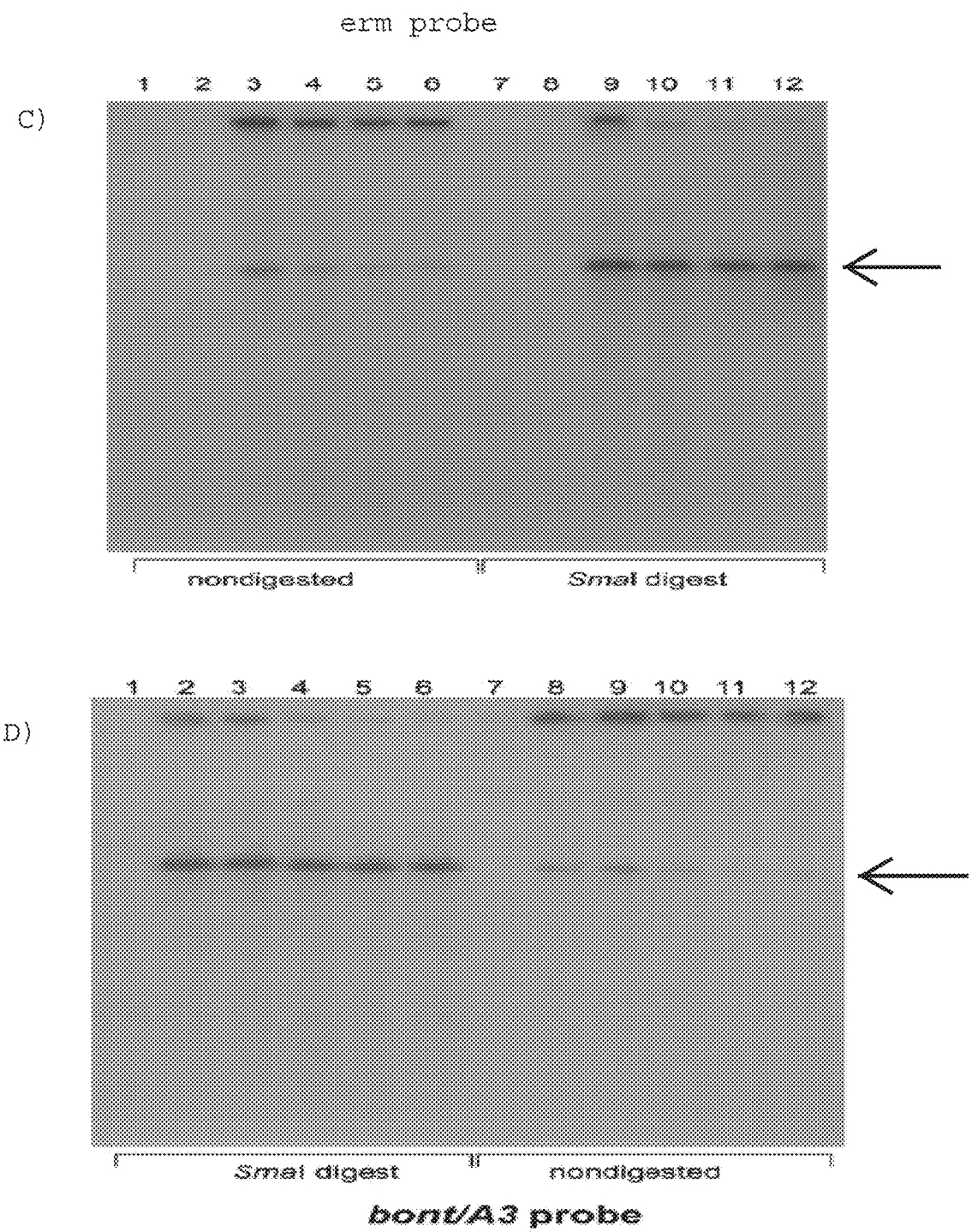
Figure 4 - C-D

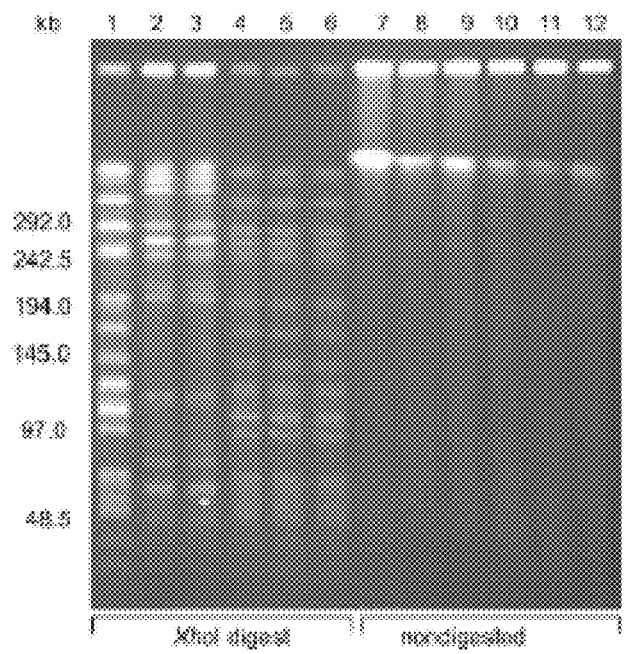
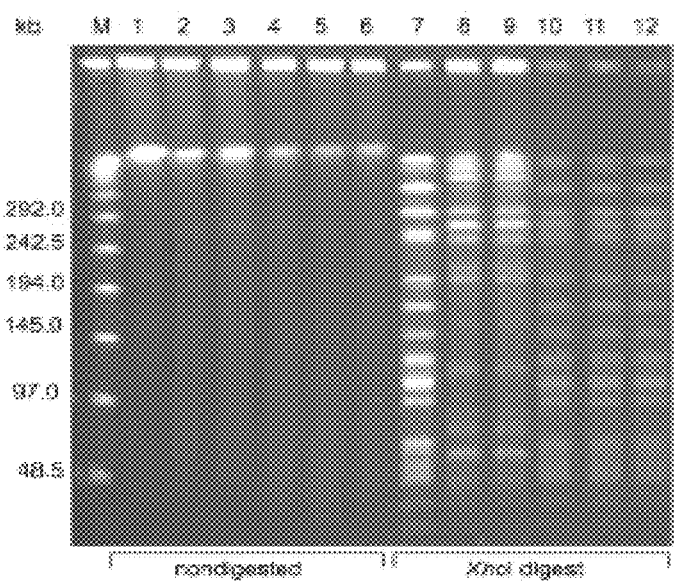
Figure 5 - A

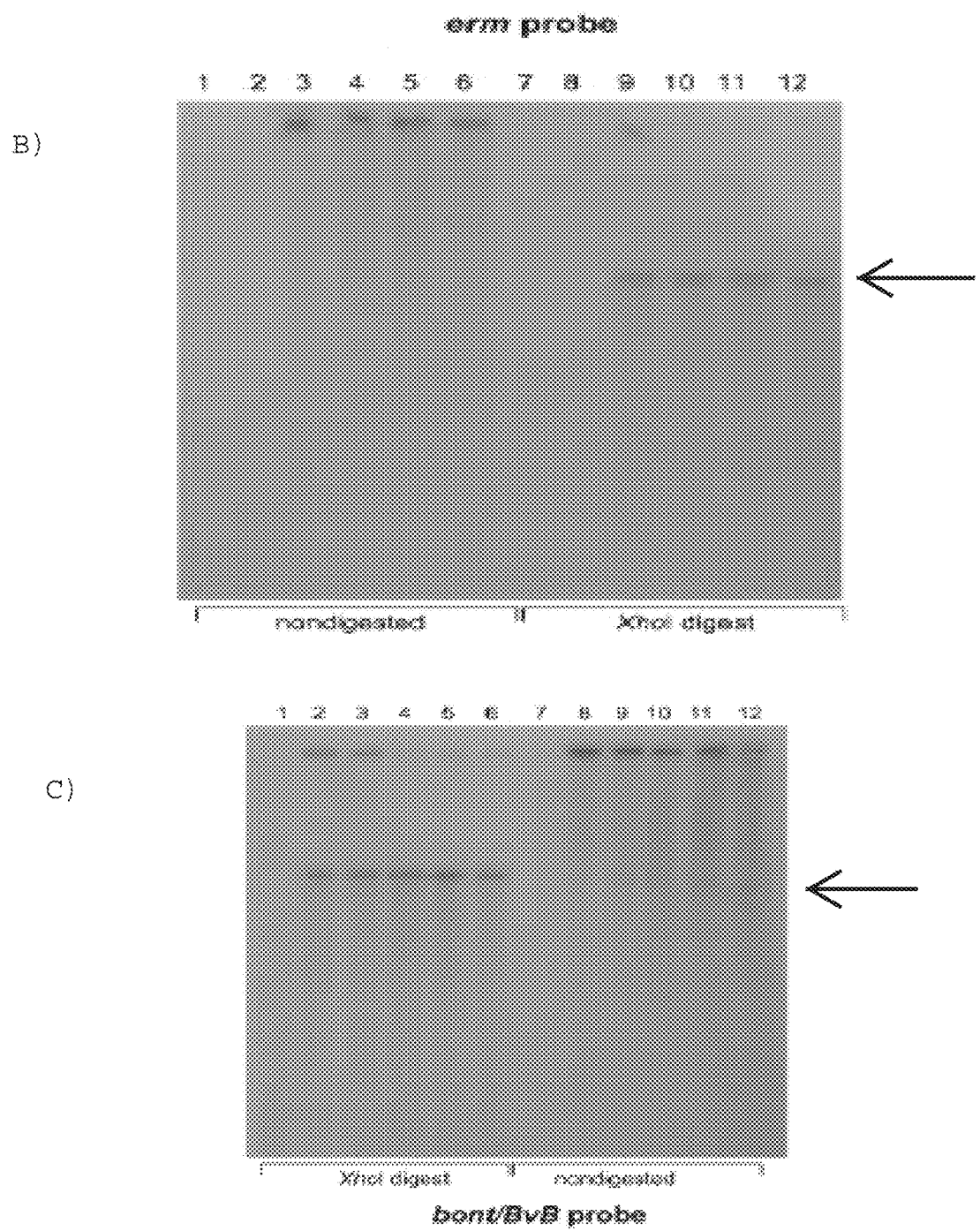
Figure 5 - B-C

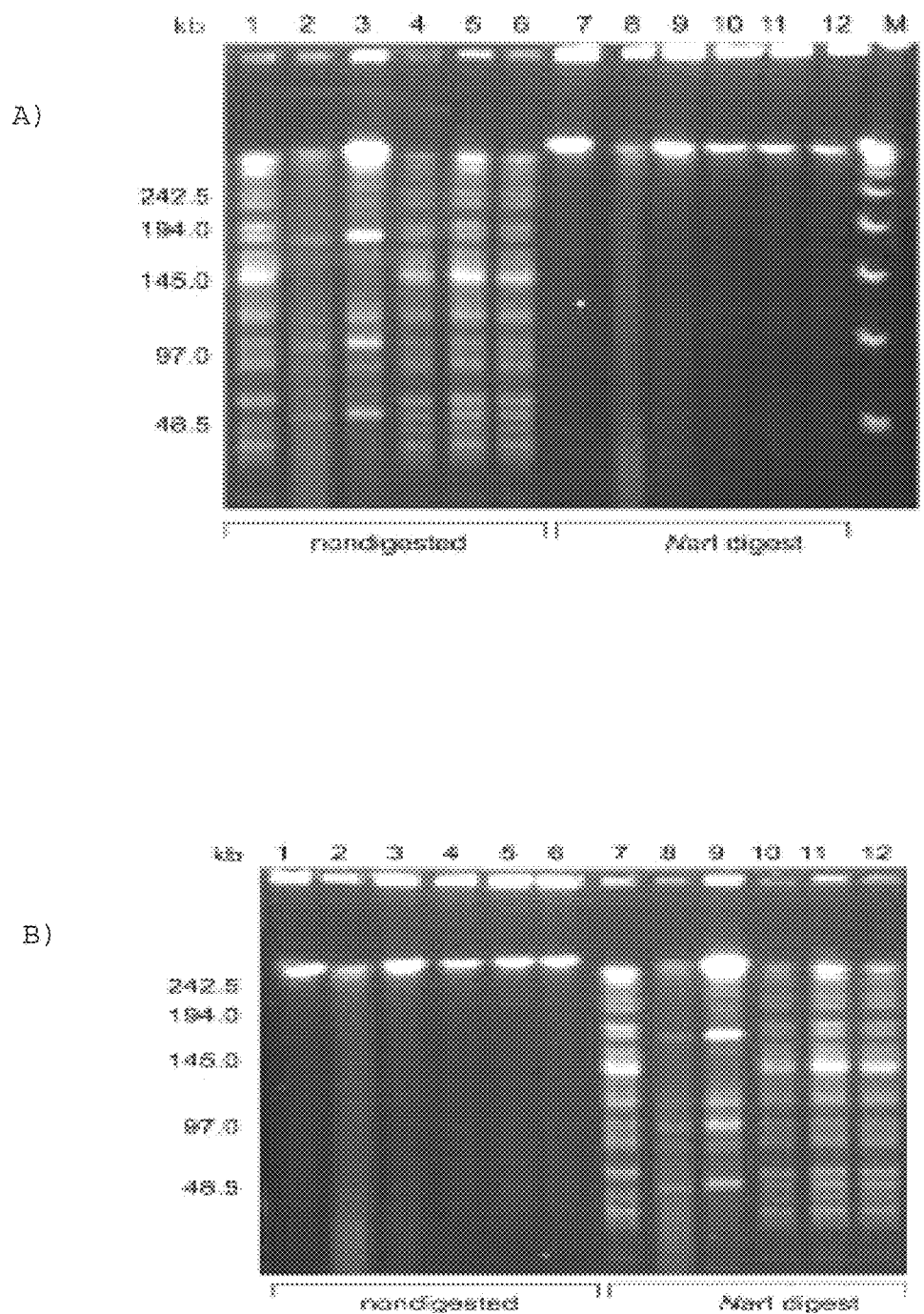
Figure 6 - A-B

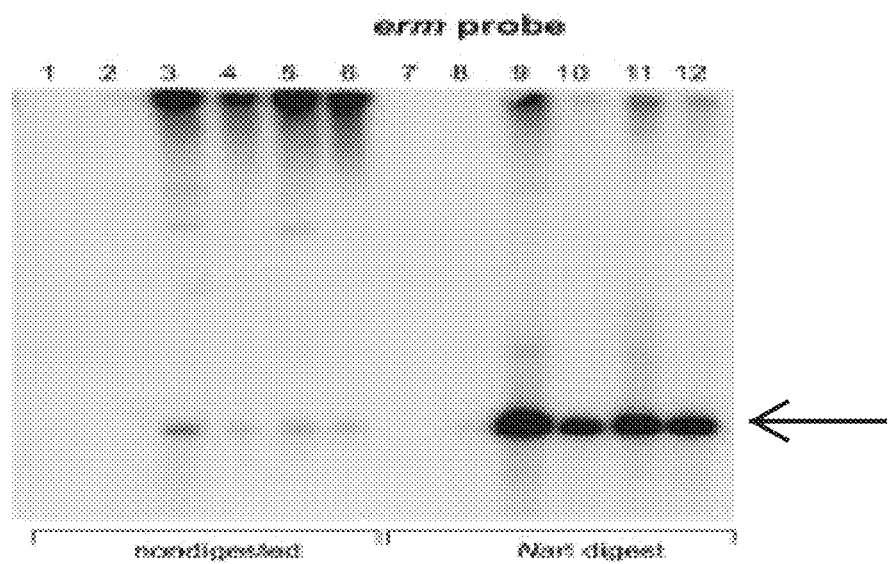
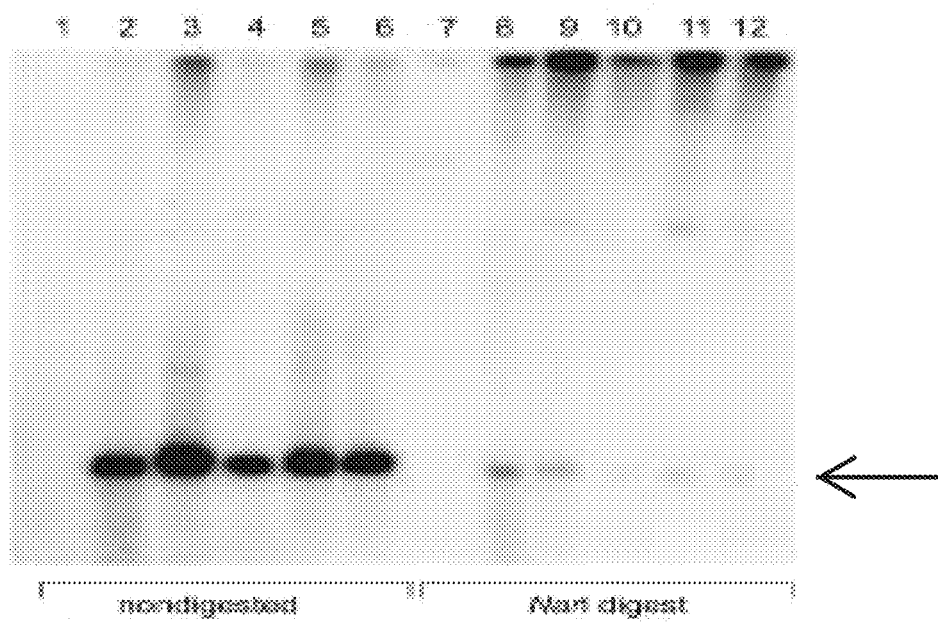
Figure 6 - C-D

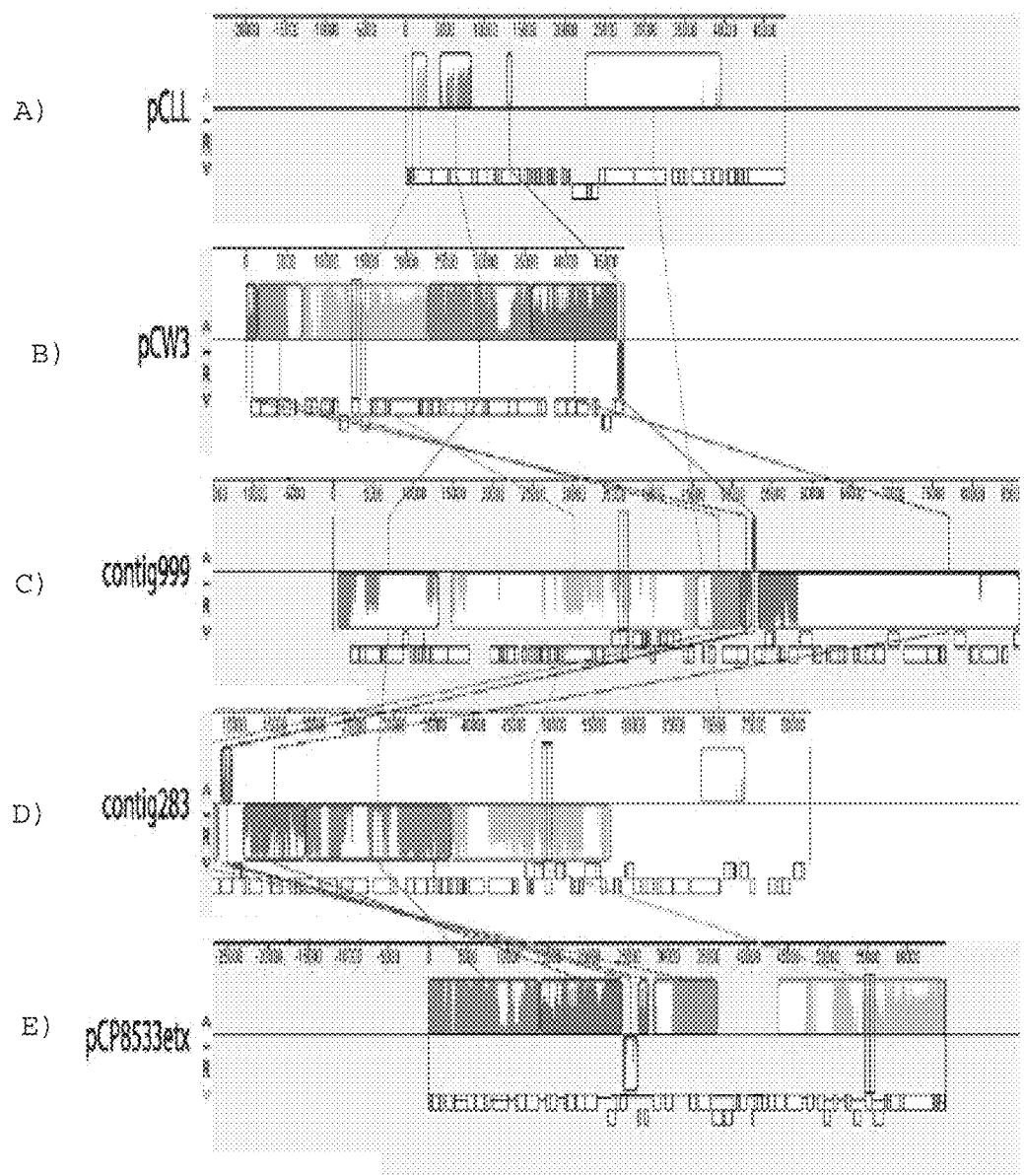
Figure 9 - A-E

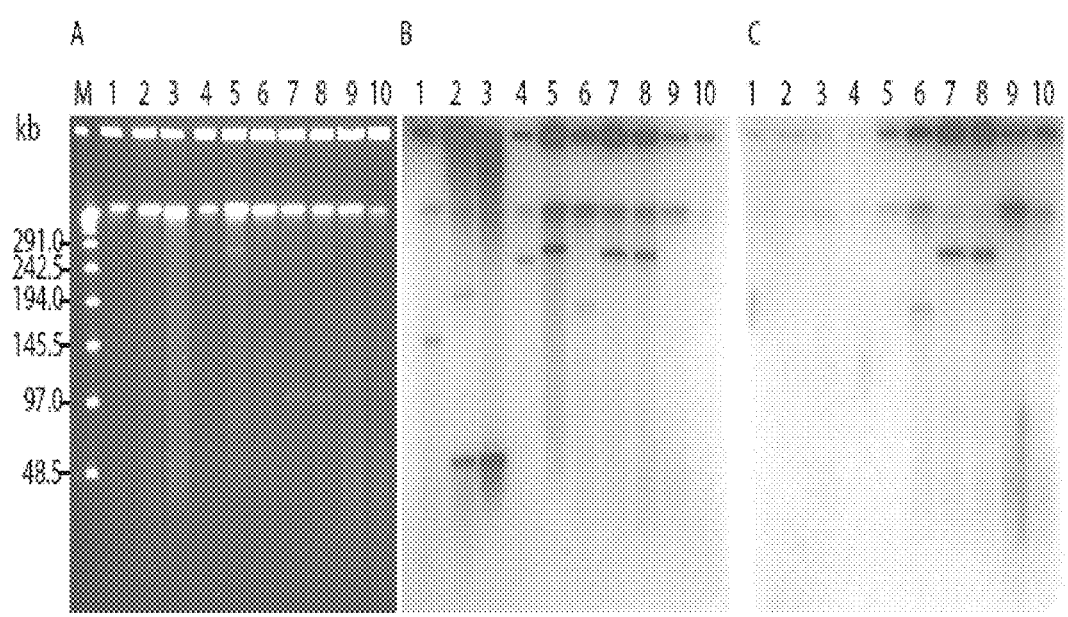
Figure 10 - A-C

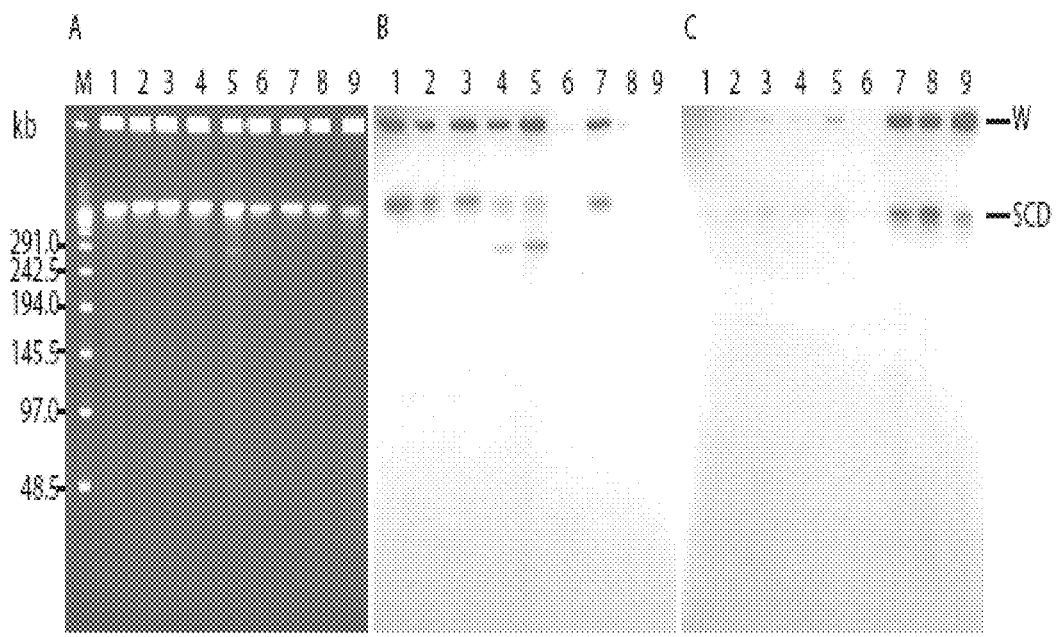
Figure 11 - A-C

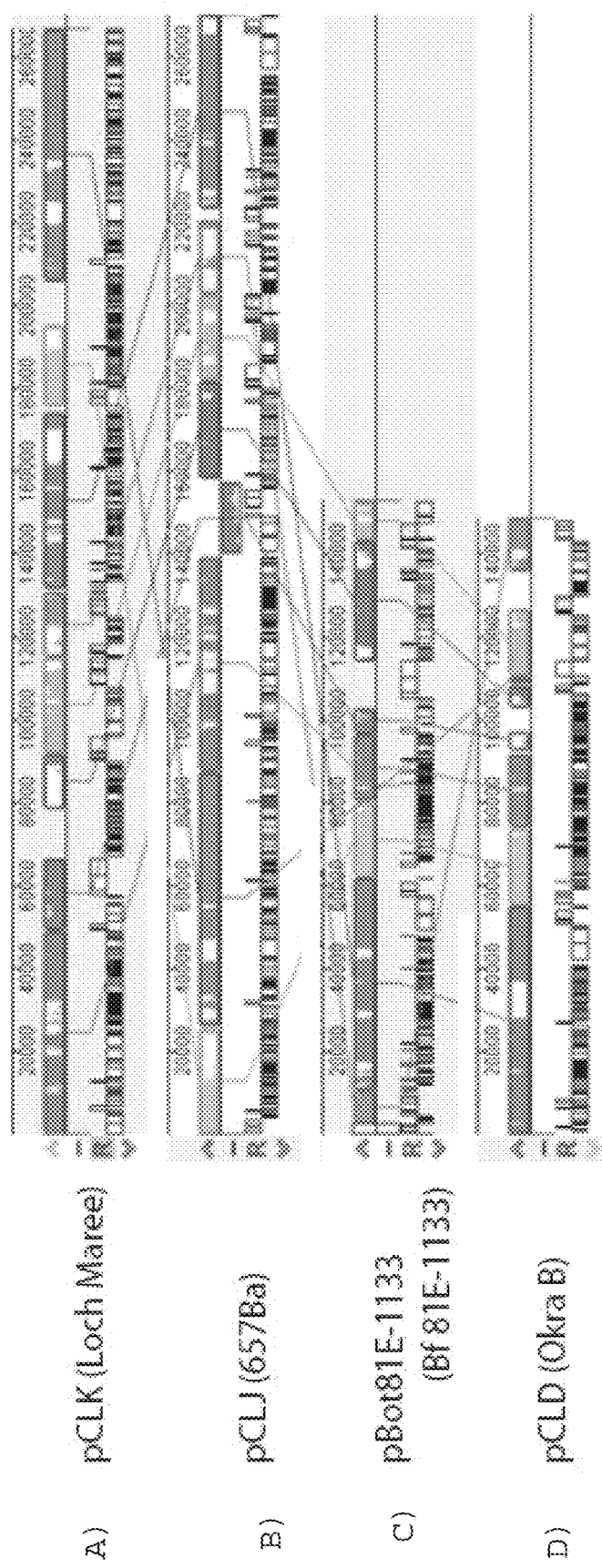
Figure 12 - A-D

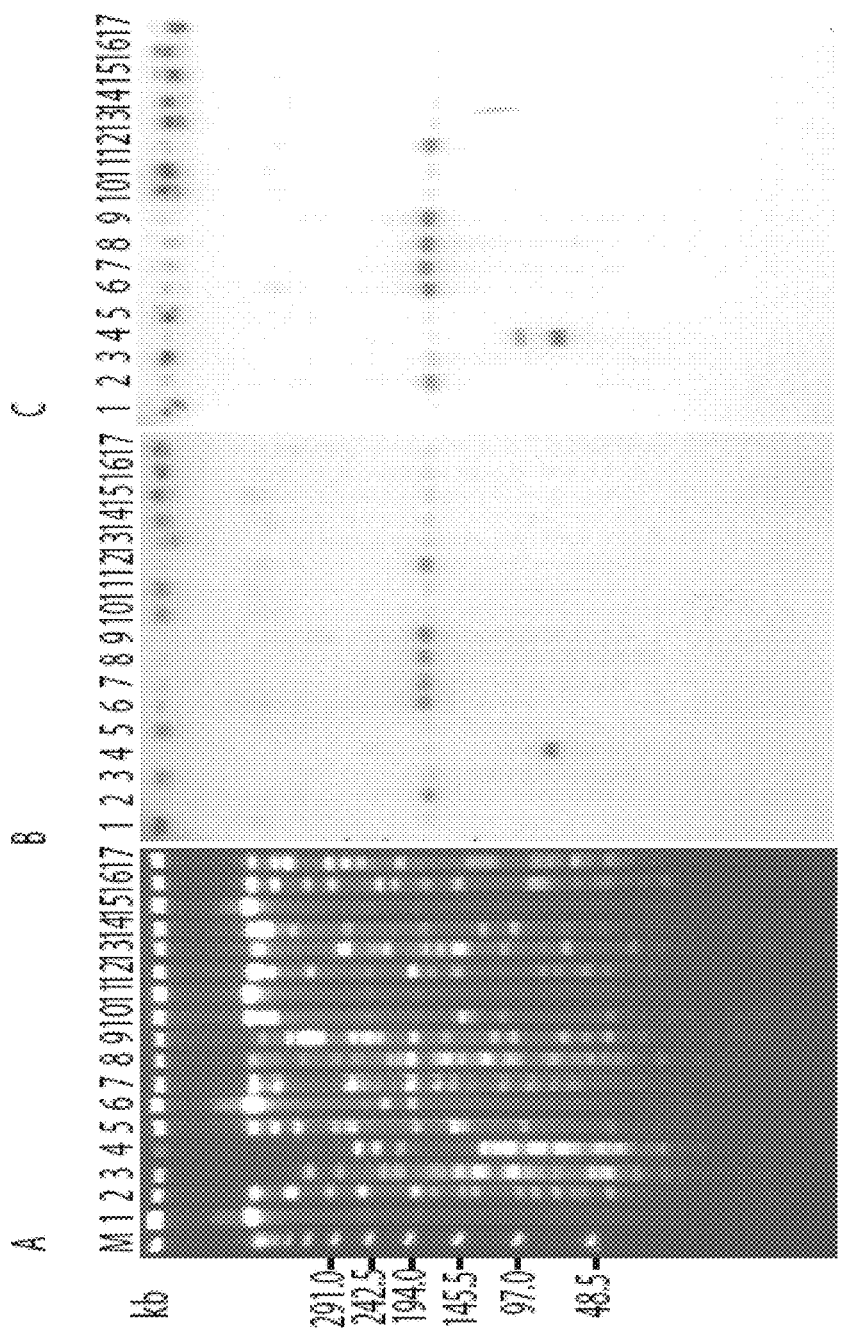
Figure 13 - A-C

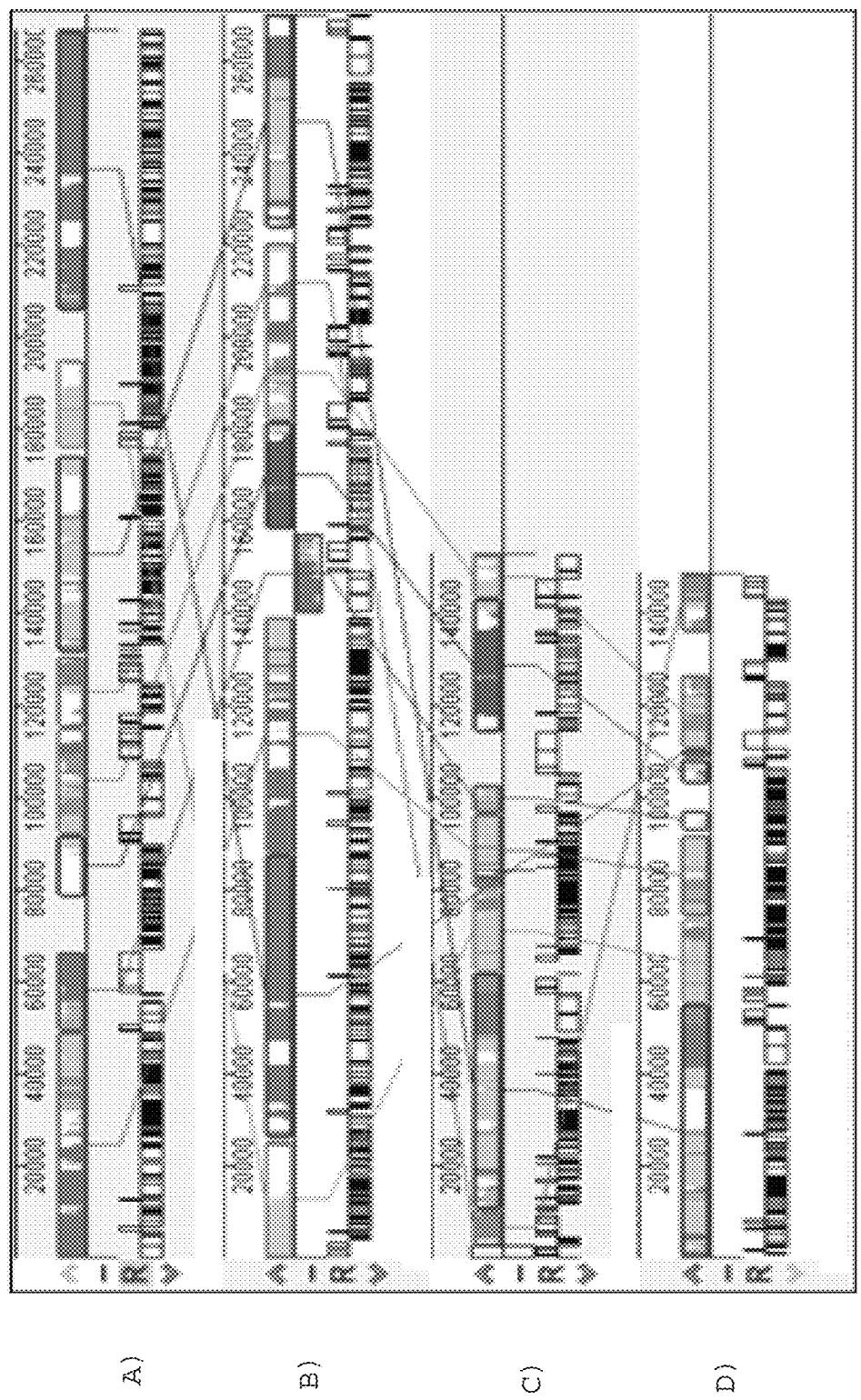
Figure 14 - A-D

Figure 15 - A-F

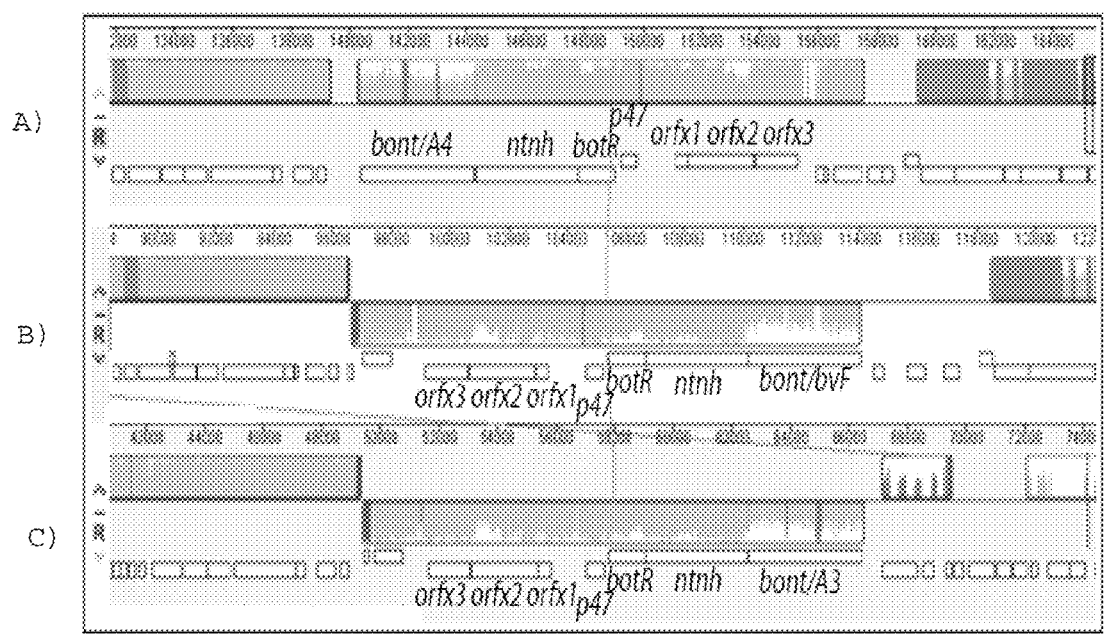
Figure 16 - A-B

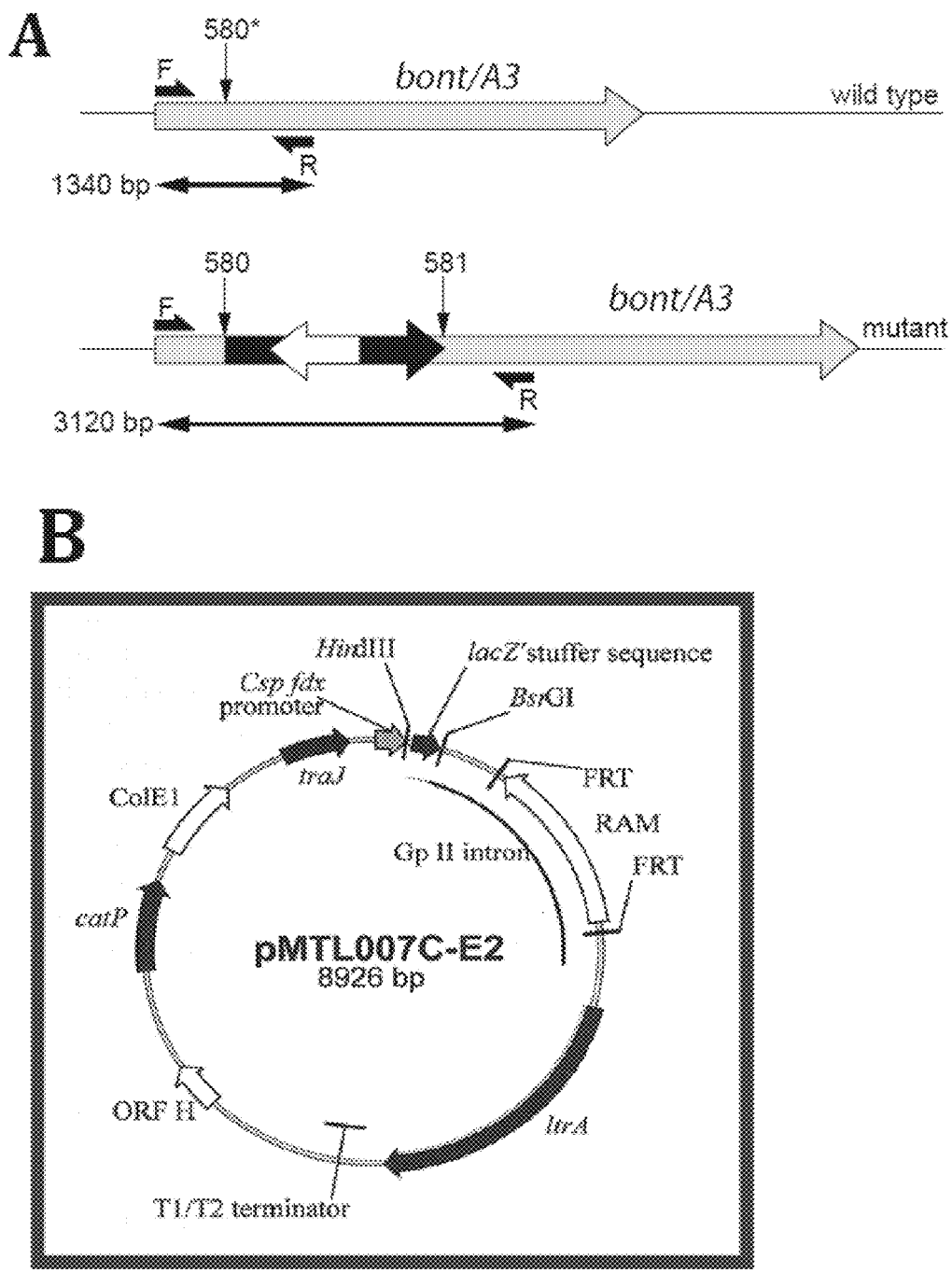
Figure 17 - A-B

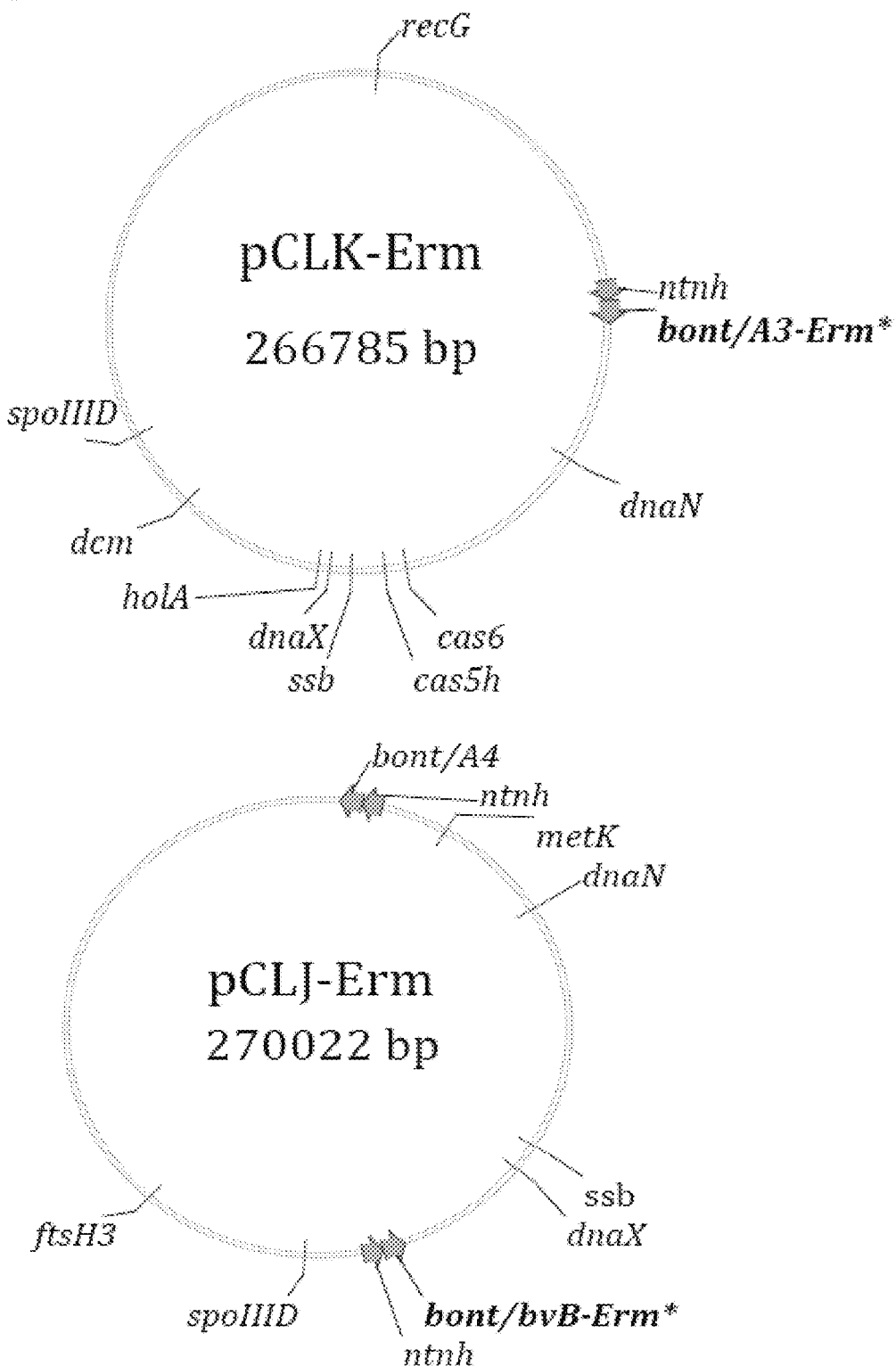
Figure 17 - C

CONJUGATIVE PLASMIDS AND METHODS OF USE THEREOF

CROSS-REFERENCE TO RELATED APPLICATIONS

This application is a continuation application of U.S. patent application Ser. No. 12/905,592, filed Oct. 15, 2010, which claims the benefit of U.S. Provisional Application No. 61/252,029, filed Oct. 15, 2009, both of which are incorporated herein by reference for all purposes.

STATEMENT REGARDING FEDERALLY-SPONSORED RESEARCH OR DEVELOPMENT

The invention was made with government support under Grant Nos. AI-057153 and AI-065359 awarded by the National Institutes of Health. The government has certain rights in the invention.

FIELD OF THE INVENTION

This invention is directed to the conjugal transfer of BoNT-encoding plasmids and their derivatives in *Clostridium botulinum* and discloses technology related to that disclosed in International Patent Application Serial No. WO 2009/006281 filed Jun. 27, 2008, which is hereby incorporated herein by reference for all purposes.

BACKGROUND OF THE INVENTION

Bacteria of the genus *Clostridium* are gram positive and include many pathogenic species responsible for significant mortality and morbidity in both humans and animals. For instance, *Clostridium tetani* is a common soil dwelling organism which produces a neurotoxin responsible for the disease tetanus. *Clostridium perfringens* is a common cause of gas gangrene and food poisoning. *Clostridium difficile* is a common cause of gastroenteritis and pseudomembraneous colitis, particularly among elderly hospital patients who have had their intestinal flora depopulated by treatment with antibiotics.

*Clostridium botulinum* is an anaerobic, gram-positive, spore-forming organism that produces the extraordinarily lethal botulinum neurotoxins (BoNTs), a distinctive neurotoxin of extraordinary potency and the cause of botulism, which can cause severe neuroparalytic illness in humans and animals. BoNT is the etiologic agent of botulism, a paralytic disease resulting from the inhibition of neurotransmitter release at the neuromuscular junction. There are several forms of botulism, and infant and foodborne represent the majority of botulism cases reported in the U. S. Despite the unsavory reputation of BoNTs as a deadly poison and as a potential bioterrorism agent, their use in treatment for numerous hyperactive muscle disorders has been widely demonstrated.

Because of their extreme toxicity, the neurotoxins produced by *Clostridium botulinum* have been the subject of extensive study. Botulinum neurotoxins (BoNT) are classified into seven serotypes, referred to as serotypes A through G, on the basis of their immunological properties. Multiple subtype neurotoxins have been and continue to be discovered especially among serotypes A, B, E and F (Arndt et al. 2006; Carter et al. 2009; Dover et al. 2009; Hill et al. 2007; Smith et al. 2005). In many cases, the amino acid sequences of the toxins have been deduced and compared. See, for example, Minton, "Molecular Genetics of Clostridial Neurotoxins," in Clostridial Neurotoxins, C. Montecucco (Ed.) Springer-Verlag, Berlin (1995).

*Clostridium* strains producing BoNTs are broadly characterized into four groups based on metabolic, physiological and genetic properties (Hatheway 1990). Group I contains proteolytic strains of serotypes A, B and F. Group II contains nonproteolytic strains of serotypes B, E and F. Unlike proteolytic strains, nonproteolytic strains lack the ability to digest meat and milk proteins and rely on exogenous proteins for the proteolytic nicking of the neurotoxin into its active di-chain form (Lynt et al. 1982). Group III includes strains of serotypes C and D and Group IV includes strains of *C. botulinum* serotype G, also referred to as *Clostridium argentinense*.

The genes encoding BoNT serotypes C, D and G have long been established to be associated with extrachromosomal elements (Sakaguchi et al. 2005; Zhou et al. 1995). Specifically, the BoNT/C1 and BoNT/D clusters are carried on bacteriophages, and in *C. botulinum* serotype G, the neurotoxin gene, bont/G, was shown to reside on a large plasmid of ca. 114 kb. However, genes encoding serotypes A, B, E and F were believed to be located on the chromosome. Recently, strains of serotype A, proteolytic and nonproteolytic strains of serotype B, and dual neurotoxin producing Ba, Ab and Bf strains have been shown to harbor neurotoxin genes on very large plasmids (Marshall et al. 2007; Smith et al. 2007; Franciosa et al. 2009). Interestingly, in dual neurotoxin-producing strains of Ba, Ab and Bf subtypes analyzed thus far, it appears that both neurotoxin genes are usually located on the same plasmid. Plasmids identified in proteolytic strains of *C. botulinum* range in size from approximately 150 to 270 kb and several plasmids found in serotypes A and B and dual neurotoxin producing Ba and Bf strains have been shown to be highly conserved, yet they carry different neurotoxin subtype genes. BoNT-encoding plasmids seem to be more prevalent among strains of serotype B than other serotypes. Unlike the large plasmids observed in proteolytic serotype B strains, plasmids found in nonproteolytic B strains are consistently smaller (approximately 48 kb) and share no homology with plasmids of proteolytic *C. botulinum* strains Interest in BoNTs has accelerated due to its potential as pharmaceutical agent for the treatment of segmental movement disorders, spasticity, pain syndromes, and various other neural disorders. In addition, the potential for the use of BoNTs in bioterrorism has been noted and, as a result, government agencies are actively investigating countermeasures against them.

In use, BoNT specifically and tightly binds to cholinergic neurons. BoNT is found natively both in bacterial cultures and in contaminated foods as a progenitor toxin complex in which the neurotoxin is associated with nontoxic components including nontoxic nonhemagglutinin (NTNH), hemagglutinin (HA) proteins, RNA, and other uncharacterized protein components. The neurotoxin component of the toxin complex is a 150 kDa protein comprising a heavy (HC) and a light (LC) chain. The LC contains the catalytic domain that cleaves nerve proteins essential for neurotransmission. Specifically, upon endocytosis and internalization into the nerve terminal, the light chain of the toxin acts to block or slow the exocytotic release of neurotransmitters, particularly acetylcholine. Selective injection of botulinum toxin into neuromuscular regions produces a local weakening of proximal muscles and relief from excessive involuntary muscle contractions. In addition to directly affecting cholinergic neurotransmission, BoNT also exerts other poorly understood effects including altering activity of autonomic ganglia.

Upon endocytosis and internalization into the nerve terminal, the light chain of the toxin acts to block or slow the exocytotic release of neurotransmitters, particularly acetylcholine. Accordingly, the ability of BoNT to specifically target peripheral nerves and its long duration of action make it a very attractive potential therapeutic tool. Complications and drawbacks of botulinum toxin therapy include immunological resistance in some patients and diffusion and resulting apoptosis of neighboring muscles. These side effects can be avoided by proper expression, purification and preparation of the toxin or toxin chains or fragments for pharmaceutical use (Schantz et al. 1992).

BoNT-encoding plasmids carrying neurotoxin genes have been identified in numerous proteolytic and nonproteolytic strains of *C. botulinum* serotypes A and B and in bivalent subtypes Bf and Ab (Marshall et al. 2007; Smith et al. 2007; Franciosa et al. 2008). Although plasmids among proteolytic strains of *C. botulinum* are quite large and tend to vary in size, plasmids found in nonproteolytic *C. botulinum* strains are much smaller and are consistently observed to be approximately 48 kb.

Two main strategies have been utilized to obtain clostridial neurotoxins, individual chains of the toxins, or non-toxigenic components of the toxin complex. The first strategy is to isolate the desired protein itself from cultures of the toxigenic *C. botulinum* strain, and then biochemically separating the chains. However, separating the chains of the purified toxins, or toxin domains, or toxin fragments is technically challenging, laborious, the yields are low. The clinical use of purified botulinum toxin fragments is thus complicated by the need for extreme purity since even minute amounts of any contaminating active toxin can be non-specific and potentially dangerous. Biochemical preparations of toxin chains or fragments are always contaminated with low levels of active neurotoxin.

The second strategy is to recombinantly produce the toxin or toxin fragments in native or heterologous hosts. Unfortunately, the expression of clostridial genes in most heterologous hosts has been found to be inefficient. Available information on clostridial gene expression in *E. coli* in particular, and also other heterologous hosts, indicates that the expression of clostridial genes in these hosts occurs at very low levels and is relatively inefficient, and necessary post-translational modifications such as proteolytic activation and molecular folding to not occur. Furthermore, expression of clostridial proteins in heterologous hosts may result in production of degraded product and/or produced as insoluble matter. Expression of clostridial genes in clostridial species is, as might be expected, more efficient and the resulting proteins are less prone to structural or sequence errors and undergo proper posttranslational modifications.

Handling of and culturing of these bacteria is difficult since not only are they highly toxic, the organisms are obligate anaerobes which die if exposed to oxygen. Therefore, the clostridia must be handled under specialized conditions. These technical difficulties reduce efficiency of approaches that can be used for gene transfer in other bacteria such as electroporation, transformation and transduction. For instance, currently used clostridial shuttle vectors are constructed using replication genes from small (less than 10 kb) cryptic clostridial plasmids such as pIP404 (*C. perfringens*), pCD6 (*C. difficile*, pCB102 (*C. butyricum*), pBP1 (*C. botulinum*) or from small plasmids (2.4-25.5 kb) isolated from *E. faecalis* (pAMβ1), *B. subtilis* (pIM13) (Davis et al. 2005; Heap et al. 2009). Besides the replication genes functional in clostridia, these vectors also contain an antibiotic resistance gene functional in both clostridia and *E. coli*, and these plasmids can be transferred to clostridial strains by electroporation. For instance, vectors that additionally contain *E. coli* oriT sequences can be introduced into clostridial strains by conjugation from a suitable *E. coli* donor strain, but there are technical difficulties as described below.

In general, these vectors can be transferred to clostridial strains and are maintained in these strains in the presence of the antibiotic that is encoded from the plasmid vector. Transfer efficiency of these vectors varies and is strain dependent. However, these plasmids are not designed to maintain large gene inserts, e.g. larger than approximately 4 kb. Therefore, they cannot be used for transfer of gene clusters such as botulinum neurotoxin clusters that are 12-16 kb. However, botulinum neurotoxins are naturally produced as protein complexes consisting of a neurotoxin associated with several nontoxigenic components. The complex protects the neurotoxin in the host cell as well as in the human/animal gut. In order to increase the yield and production of high quality botulinum neurotoxins, vectors that can transfer large gene clusters are necessary.

Accordingly, the study and the production of clostridial toxin genes as well as other clostridial genes organized in gene clusters would be greatly facilitated by a plasmid providing the conjugal transfer of BoNT-encoding plasmids in other *Clostridium* species, thereby providing a plasmid and method for the widespread distribution of BoNT-encoding plasmids in other *Clostridium* species, especially *Clostridium* species that do not naturally produce these gene products.

SUMMARY OF THE INVENTION

The invention provides a novel conjugative transfer plasmid comprising: an origin of replication effective in *Clostridium* species; a protein coding sequence for a gene of interest operably joined to a promoter effective in *Clostridium* species; and an origin of conjugative transfer capable of modulating the conjugative transfer of the plasmid into a recipient *Clostridium* species, wherein the gene of interest is expressed in the recipient *Clostridium* species.

In one embodiment, the gene of interest is a botulinum neurotoxin gene for expressing clostridial toxins, toxin fragments, or antigenic portions thereof. The gene of interest may be from the same *Clostridium* species as the recipient *Clostridium* species or from a different *Clostridium* species.

In one embodiment, the plasmid may be selected from any donor *Clostridium* species. For instance, the plasmid may be found on *C. botulinum* strains selected from the group consisting of serotypes A, B, C, D, E, F or G. Alternatively, the plasmid may be from *C. botulinum* strains selected from the group consisting of Ba, Ab, Bf, Af or A(B). The plasmid may be from the same *Clostridium* species as the recipient *Clostridium* species or from a different *Clostridium* species. In one embodiment, the plasmid is selected from the group consisting of pBotCDC-A3, pCLJ, pCLL, pBot81E-1133 and pCLD.

In one embodiment, the promoter effective in *Clostridium* species is NTNH-BoNT promoter from *C. botulinum*.

In one embodiment, the recipient *Clostridium* species is toxic or nontoxic, such as LNT01 or Hall A-Hyper. The recipient *Clostridium* species may also be proteolytic or nonproteolytic.

In one embodiment, the conjugative transfer plasmid further comprises an antibiotic resistant gene that confers resistance to the recipient *Clostridium* species to erythromycin, kanamycin, ampicillin, tetracycline, chloramphenicol, spectinomycin, gentamycin, zeomycin or streptomycin. In one embodiment, the conjugative transfer plasmid further comprises an antibiotic resistant gene for conferring resistance to the recipient *Clostridium* species to erythromycin, tetracycline, chloramphenicol or thiamphenicol.

In an alternate embodiment, the present invention provides a novel conjugative transfer plasmid comprising a BoNT-encoding plasmid containing an origin of replication effective in *Clostridium* species, the BoNT encoded by the plasmid operably joined to a promoter effective in the *Clostridium* species; and an origin of conjugative transfer capable of modulating the conjugative transfer of the BoNT-encoding plasmid into a recipient *Clostridium* species, wherein the BoNT encoded by the plasmid is expressed in the recipient *Clostridium* species.

In one embodiment, the BoNT-encoding plasmid may be selected from any donor *Clostridium* species. For instance, the BoNT-encoding plasmid may be selected from *C. botulinum* serotypes A, B, C, D, E, F or G. Alternatively, the plasmid may be selected from *C. botulinum* strains Ba, Ab, Bf, Af or A(B). The BoNT-encoding plasmid may be from the same *Clostridium* species as the recipient *Clostridium* species or from a different *Clostridium* species. In one embodiment, BoNT-encoding plasmid is selected from the group consisting of pBotCDC-A3, pCLJ, pCLL, pBot81E-1133 and pCLD.

In one embodiment, the BoNT encoded by the plasmid is a botulinum neurotoxin gene for expressing clostridial toxins, toxin fragments, or antigenic portions thereof. The BoNT encoded by the plasmid may be from the same *Clostridium* species as the recipient *Clostridium* species or from a different *Clostridium* species.

In one embodiment, the BoNT-encoding plasmid further comprises an antibiotic resistant gene confers resistance to the recipient *Clostridium* species to erythromycin, tetracycline, chloramphenicol, and others known to be encoded from a plasmid. Where the recipient *Clostridium* species is *C. botulinum*, the antibiotic resistant gene confers resistance to the recipient *Clostridium* species to erythromycin, tetracycline, chloramphenicol or thiamphenicol.

In an alternate embodiment, the present invention provides a novel method of conjugatively transferring a gene of interest into a recipient *Clostridium* species. The method comprises conjugatively transferring a plasmid comprising an origin of replication effective in *Clostridium* species, a protein coding sequence for a gene of interest operably joined to a promoter effective in *Clostridium* species, and an origin of conjugative transfer capable of modulating the conjugative transfer of the plasmid into the recipient *Clostridium* species, wherein the gene of interest encoded by the plasmid is expressed in the recipient *Clostridium* species.

In one embodiment, the gene of interest is a botulinum neurotoxin gene for expressing clostridial toxins, toxin fragments, or antigenic portions thereof. The gene of interest may be from the same *Clostridium* species as the recipient *Clostridium* species or from a different *Clostridium* species.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed descriptions are to be regarded as illustrative in nature and not restrictive.

BRIEF DESCRIPTION OF THE FIGURES

FIG. 1. Confirmation of tagging *C. botulinum* BoNT-encoded plasmids pBotCDC-A3-Erm (strain CDC-A3), pCLJ-Erm (strain 657Ba) and pCLL-Erm (strain Eklund 17B) by PCR analysis. PCR products of wild-type *C. botulinum* strains CDC-A3 (Lane 1), 657Ba (Lane 4) and Eklund 17B (Lane 7) and two erythromycin resistant, thiamphenicol sensitive clones of each of CDC-A3 (Lanes 2 and 3), 657Ba (Lanes 5 and 6) and Eklund 17B (Lanes 8 and 9) strains; 1 kb Plus ladder (Invitrogen) (Lane M).

FIG. 2. Confirmation of tagging *C. botulinum* BoNT-encoding plasmids pBotCDC-A3-Erm (strain CDC-A3), pCLJ-Erm (strain 657Ba) and pCLL-Erm (strain Eklund 17B) by PFGE and Southern hybridization analysis. (B) Ethidium bromide stained PFGE of nondigested DNA samples from *C. botulinum* strains: wild type CDC-A3 (Lane 1), CDC-A3580s1 (Lane 2), wild type 657Ba (Lane 3), 657Ba-CT4 (Lane 4), wild type Eklund 17B (Lane 5) and Eklund 17B-CT11 (Lane 6); Lambda PFG Marker (Lane M), (New England Biolabs). The position of BoNT-encoding plasmids is indicated with arrows. (A) Southern hybridization with the bont/A3 probe (Lanes 1 and 2); the bont/bvB probe (Lanes 3 and 4) and the bont/npB probe (Lanes 5 and 6); (C) Southern hybridization with the ermB probe. PFGE conditions: 6V/cm, 12° C., 1-20 s pulse time, 24 h.

FIG. 3. Confirmation of plasmid transfer from *C. botulinum* strains CDC-A3580s1, 657BaCT4-2 and Eklund 17BCT11-1 to strain LNT01. Pulsed-field gel electrophoresis of (A) SmaI digested DNA of *C. botulinum* strains LNT01 (Lane 1), CDC-A3580s1 (Lanes 2-4) and LNT01 transconjugants (pCLK-Erm) (Lanes 5-8), (B) XhoI digested DNA of *C. botulinum* strains LNT01 (Lane 1), 657BaCT4-3 (Lane 2) and LNT01 transconjugants (pCLJ-Erm) (Lanes 3-4), and (C) NarI digested DNA of *C. botulinum* strains LNT01 (Lane 1), Eklund 17BCT11-1 (Lane 2) and LNT01 transconjugants (pCLL-Erm) (Lanes 3-6), Lambda PFG Marker (Lane M), New England Biolabs. PFGE conditions for gels (A) and (B): 6V/cm, 12° C., 1-26 s pulse time, 24 h, and (C): 6V/cm, 12° C., 1-5 s, 24 h.

FIG. 4. Confirmation of plasmid pBotCDC-A3-Erm transfer from *C. botulinum* strain CDC-A3580s1 to strain LNT01 by PFGE and Southern hybridization analysis. (A) Ethidium bromide stained PFGE of *C. botulinum* DNA samples: (A) SmaI digested DNA of *C. botulinum* strain LNT01 (Lanes 1 and 7), CDC-A3 wild type (Lanes 2 and 8), CDC-A3580s1 (Lanes 3 and 9), and LNT01 transconjugants (pBotCDC-A3-Erm) (Lanes 4-6 and 10-12); (B) nondigested DNA samples (Lanes 1-6); SmaI-digested DNA samples (Lanes 7-12). Lambda PFG Marker (Lane M), New England Biolabs. The position of the pBotCDC-A3 plasmid is indicated with an arrow. Southern hybridization with: (C) the ermB probe, and (D) the bont/A3 probe. PFGE conditions: 6V/cm, 12° C., 1-26 s pulse time, 24 h.

FIG. 5. Confirmation of plasmid pCLJ-Erm transfer from *C. botulinum* strain 657BaCT4 to strain LNT01. (A) Ethidium bromide stained PFGE of *C. botulinum* strains: (A) LNT01 (Lanes 1 and 7), wild type strain 657Ba (Lanes 2 and 8); 657BaCT4 (Lanes 3 and 9) and LNT01 transconjugants (pCLJ-Erm) (Lanes 4-6 and 10-12); (B) nondigested DNA samples (Lanes 1-6); XhoI digested DNA samples (Lanes 7-12). Lambda PFG Marker (Lane M), New England Biolabs. The position of the pCLJ plasmid is indicated with an arrow. Southern hybridization with: (B) the ermB probe and (C) the bont/bvB probe. PFGE conditions: 6V/cm, 12° C., 1-26 s pulse time, 24 h.

FIG. 6. Confirmation of plasmid pCLL-Erm transfer from C. botulinum strain Eklund 17BCT11 to strain LNT01. (A-B) Ethidium bromide stained PFGE of C. botulinum strains: LNT01 (Lanes 1 and 7), wild type strain Eklund 17B (Lanes 2 and 8); Eklund 17BCT11 (Lanes 3 and 9) and LNT01 transconjugants (pCLL-Erm) (Lanes 4-6 and Lanes 10-12). (A) nondigested DNA samples (Lanes 1-6); Nan digested DNA samples (Lanes 7-12). Lambda PFG Marker (Lane M), New England Biolabs. The position of the pCLL plasmid is indicated with an arrow. Southern hybridization with: (C) the ermB probe, and (D) the bont/npB probe. PFGE conditions: 6V/cm, 12° C., 1-20 s pulse time, 24 h.

FIG. 9. Plasmid alignment of (A) pCLL (SEQ ID NO: 3; C. botulinum strain Eklund 17B); (B) pCW3 (SEQ ID NO: 27; C. perfringens strain CW92); (C) contig 1108490430999 (SEQ ID NO:29); (D) contig 1108490430283 (SEQ ID NO: 30; C. perfringens type D strain JGS1721) and (E) pCP8533etx (SEQ ID NO: 28; C. perfringens type B strain NCTC8533B4D). The alignment has five panels, one for each plasmid. The top portions of the panels are composed of segments corresponding to the boundaries of locally collinear blocks (LCBs) with lines connecting the homologous blocks in each plasmid. LCBs below a plasmid's center line are in the reverse complement orientation relative to the reference plasmid (pCLL).

FIG. 10. PFGE and Southern hybridization analysis of C. botulinum serotype A, B, Af and F strains. (A) PFGE of nondigested DNA; (B) Southern hybridizations with bont/A and (C) bont/F gene probes. Lanes: (M) Lambda PFGE ladder, (New England Biolabs), (1) ATCC 3502, (2) 5328A, (3) KyotoF, (4) Loch Maree, (5) 657Ba, (6) 14842, (7) Af84, (8) Langeland F, (9) 4852; (W) well position, (SCD) sheared chromosomal DNA.

FIG. 11. PFGE and Southern hybridization analysis of C. botulinum serotype B, Bf and F strains; (A) PFGE of nondigested DNA; (B) Southern hybridizations with bont/B and (C) bont/F gene probes. Lanes: (M) Lambda PFGE ladder (New England Biolabs), (1) OkraB, (2) 10068, (3) 17B, (4) 14842, (5) 657Ba, (6) 81E-1133, (7) 3281(32419), (8) 3281(32419), (9) Langeland F, (10) 4852.

FIG. 12. Plasmid alignment of the highly homologous virulence plasmids of proteolytic C. botulinum strains (A) Loch Maree (pCLK); (B) 675 Ba (pCLJ): (C) Bf 81E-1133 (pBot81E-1133); and (D) Okra B (pCLD).

FIG. 13. PFGE and Southern hybridization analysis of C. botulinum strain Bf 81E-1133. (A) PFGE of nondigested and digested DNA; (B) Southern hybridizations with bont/B and (C) bont/F gene probes. Lanes: (M) Lambda PFGE ladder, (New England Biolabs), (1) Nondigested DNA; Digests with (2) AatII, (3) ApaI, (4) BglI, (5) EagI, (6) MluI, (7) NaeI, (8) NarI, (9) NnuI, (10) PvuI, (11) RsnII, (12) SalI, (13) SacII, (14) SbfI, (15) SfiI, (16) SmaI, (17) XhoI.

FIG. 14. Plasmid alignment of (A) pCLK (Loch Maree) (SEQ ID NO: 1); (B) pCLJ (657) (SEQ ID NO: 2); (C) contigs 18 and 23 (Bf 81E-1133) (SEQ ID NOs: 68 and 69 respectively); and (D) pCLD (Okra) (SEQ ID NO: 4) in backbone view. Portions of LCBs in mauve colorrepresent regions of DNA conserved in all four plasmids. Homologous regions conserved between two plasmids are as follows: pCLK and pCLJ, pCLK and pBot81E-1133, pCLK and pCLD, pCLJ and pCLD, or pBot81E-1133 and pCLD. Homologous regions conserved between three plasmids are as follows: pCLK, pCLJ, and pBot81E-1133; pCLJ, pBot81E-1133, and pCLD; pCLK, pBot81E-1133, and pCLD; pCLK, pCLJ and pCLD. Regions of LCBs without color represent regions unique to each plasmid.

FIG. 15. Plasmid alignments magnified for the LCB containing the A toxin cluster of (A) pCLJ (SEQ ID NO: 2) (657); (B) contigs 18 & 23 (SEQ ID NOs: 68 and 69 respectively) (Bf 81E-1133); and (C) pCLK (SEQ ID NO: 1) (Loch Maree). The LCB containing the B toxin clusters of (D) pCLJ (657); (E) contigs 18 & 23 (Bf81E-1133); and (F) pCLD (SEQ ID NO: 4) (Okra).

FIG. 16. Plasmid alignment in backbone view magnified for the LCB containing the A toxin cluster of pCLJ (SEQ ID NO: 2) (657), contigs 18 & 23 (SEQ ID NOs: 68 and 69 respectively) (Bf81E-1133), and pCLK (SEQ ID NO: 1) (Loch Maree). Portions of LCBs in gray represent regions of DNA conserved in all three plasmids. Homologous regions conserved between two plasmids are as follows: pCLJ and pBot81E-1133, pCLJ and pCLK, or pBot81E-1133 and pCLK.

FIG. 17. (A) Schematic presentation of wild type and mutated botulinum neurotoxin genes. ClosTron insertion site is shown with a vertical arrow an (*). (B) ClosTron vector pMTL007C-E2 containing the re-targeted group II intron utilized in site specific gene inactivation. (C) Plasmids pCLK-Erm and pCLK-Erm.

DETAILED DESCRIPTION OF THE INVENTION

Figure 7:
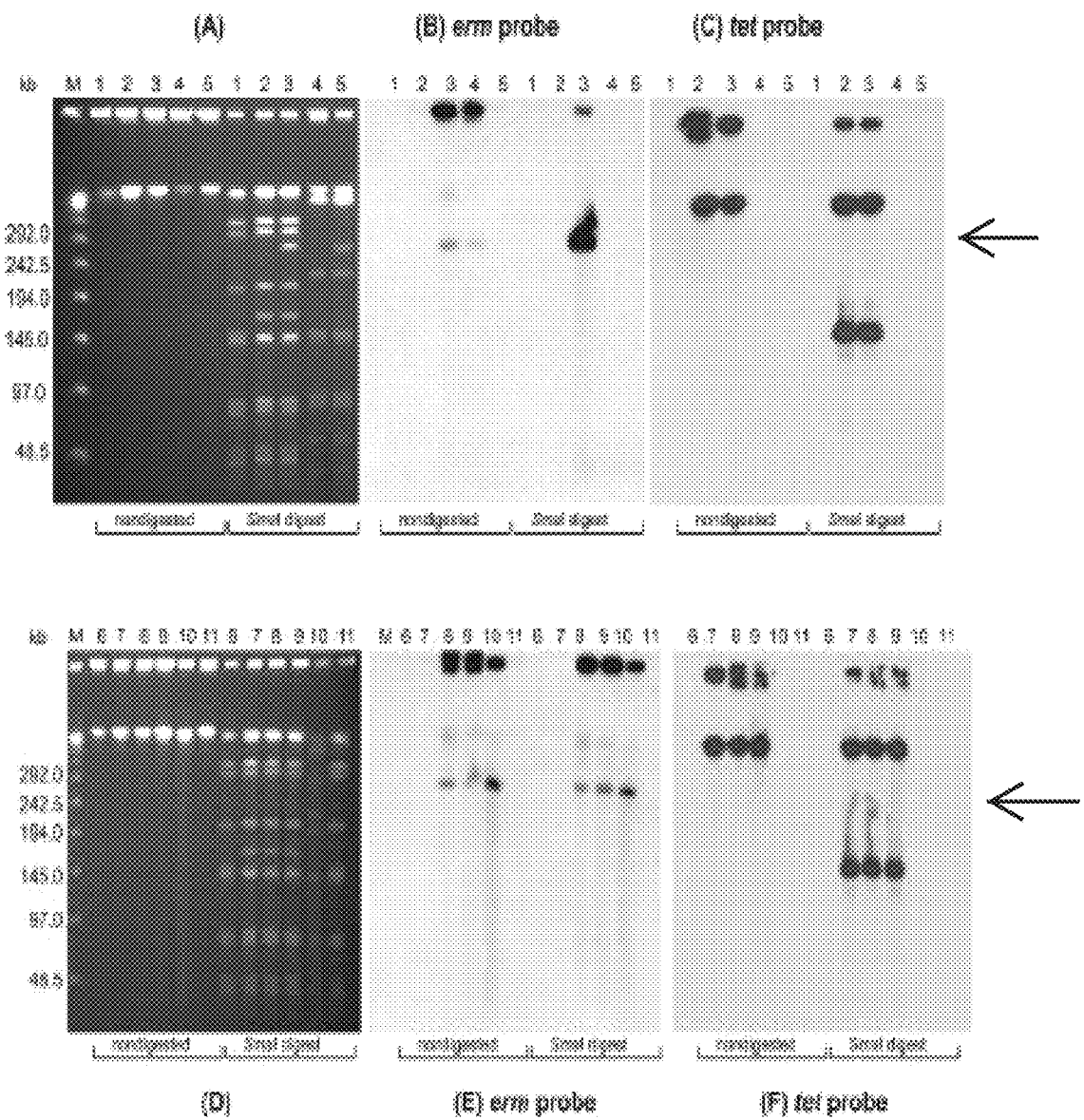
FIG. 7. Confirmation of plasmid pCLK-Erm and pCLJ-Erm transfer to C. botulinum Hall A-hyper-Tn916 mutant strain. (A) Ethidium bromide stained PFGE of C. botulinum strains: wild type Hall A-hyper (Lane 1), Hall A-hyper/Tn916 mutant (Lane 2); Hall A-hyper/Tn916/pBotCDCA3-Erm (Lane 3); CDC-A3 plasmid-cured (Lane 4); wild type CDC-A3 (Lane 5). (D) Ethidium bromide stained PFGE of C. botulinum strains: wild type Hall A-hyper (Lane 6), Hall A-hyper/Tn916 mutant (Lane 7); Hall A-hyper/Tn916/pCLJ-Erm (Lanes 8 and 9); 657Ba-CT4 (Lane 10); wild type Hall A-hyper (Lane 11). Nondigested DNA and SmaI digests were loaded on the gels as indicated below the lanes. Lambda PFG Marker (Lane M), New England Biolabs. The position of the pBotCDC-A3 and pCLJ plasmids is indicated with arrows. Southern hybridization with: (B and E) the ermB probe; and (C and F) the tet probe. PFGE conditions: 6V/cm, 12° C., 1-26 s pulse time, 24 h.

The present invention provides novel conjugatively transferable plasmids and methods of use thereof.

I. In General

In the specification and in the claims, the terms "including" and "comprising" are open-ended terms and should be interpreted to mean "including, but not limited to . . . ."

These terms encompass the more restrictive terms "consisting essentially of" and "consisting of."

As used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", "characterized by" and "having" can be used interchangeably.

Unless defined otherwise, all technical and scientific terms used herein have the same meanings as commonly understood by one of ordinary skill in the art to which this invention belongs. All publications and patents specifically mentioned herein are incorporated by reference in their entirety for all purposes including describing and disclosing the chemicals, instruments, statistical analyses and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

II. The Invention

The present invention provides novel conjugatively transferable plasmids and methods of use thereof.

A. Conjugatively Transferrable Plasmids and Methods of Synthesis Thereof.

The present invention provides novel *C. botulinum* conjugatively transmissible plasmids and methods of use thereof. By "conjugative transfer" we mean the horizontal transmission of genetic information from one bacterium to another (both uni- and multi-directionally). The genetic material transferred may be a plasmid or it may be part of a chromosome. Bacterial cells possessing a conjugative plasmid generally contain a surface structure (the sex pilus) that is involved in the coupling of donor and recipient cells, and the transfer of the genetic information. Conjugation involves contact between cells, and the transfer of genetic traits can be mediated by many plasmids. Among all natural transfer mechanisms, conjugation is the most efficient. For example, the F plasmid of *E. coli*, the pCF10 plasmid of *E. faecalis* and the pXO16 plasmid of *B. thuringiensis* are able to sustain conjugative transfer in liquid medium and exhibit transfer efficiencies of close to 100%. Thus, the conjugative process permits the very efficient delivery of plasmid DNA into a recipient bacterium.

Specifically, in one embodiment, the present invention provides novel, conjugatively transmissible plasmids and their derivatives capable of encoding a gene of interest, wherein the plasmid is capable of being transferred among and between clostridial species, thereby providing for the efficient delivery of the genes of interest into a clostridial host and the expression of said genes of interest in that host. More specifically, in one embodiment, the invention provides novel BoNT-encoding plasmids and their derivatives for conjugal transfer of these plasmid from donor *C. botulinum* strains into recipient *Clostridium* species, and used for expression of gene(s) of interest in the recipient *Clostridium* species. The novel conjugative plasmid derivatives may be comprised of replication and conjugal transfer functions derived from native conjugative plasmids found in various strains of *C. botulinum*, that can efficiently replicate in *Clostridium* species; are capable of modulating the conjugative transfer of the plasmids into recipient *Clostridium* species; and stably maintain large DNA inserts such as genes and/or gene clusters. The protein coding sequence for a gene or gene clusters of interest are operably joined to a promoter effective in *Clostridium* species; wherein the gene(s) of interest is(are) expressed in the recipient *Clostridium* species.

By "plasmid" we mean an extra-chromosomal DNA molecule separate from the chromosomal DNA. Plasmids are generally dispensable DNA molecules that are stably maintained in bacterial populations. Plasmids replicate extra-chromosomally inside the bacterium and can transfer their DNA from one cell to another by a variety of mechanisms. DNA sequences controlling extra chromosomal replication (ori) and transfer (tra) are distinct from one another; i.e., a replication sequence generally does not control plasmid transfer, or vice-versa. Replication and transfer are both complex molecular processes that make use of both plasmid- and host-encoded functions. In many cases, a plasmid is circular and double-stranded. Plasmids usually occur naturally in bacteria, but are sometimes found in eukaryotic organisms. Plasmid size varies from 1 to over 1,000 kilobase pairs (kbp). The number of identical plasmids within a single cell can range anywhere from one to even thousands under some circumstances.

The typical conjugative plasmid carries its own origin of replication (oriV) as well as an origin of transfer (oriT). It also typically includes a tra and a trb locus. When conjugation is initiated, an enzyme creates a "nick" in one plasmid DNA strand at the oriT. The enzyme may work alone or in a complex of over a dozen proteins. The transferred, or T-strand, is unwound from the plasmid and transferred into the recipient bacterium in a 5'-terminus to 3'-terminus direction. The remaining strand is replicated, either independent of conjugative action (vegetative replication, beginning at the oriV) or in concert with conjugative replication. Conjugation functions are usually plasmid encoded, but some conjugation genes can be found on the chromosome and can exhibit their activity of plasmid transfer in trans. Numerous conjugative plasmids (and transposons) are known, which can transfer associated genes within one species (narrow host range) or between many species (broad host range). Conjugation can occur between genera as widely diverse as anaerobes and aerobes.

In one embodiment, plasmids can be used from any donor *Clostridium* species. The conjugatively transferable plasmid of the present invention can be selected from any proteolytic or nonproteolytic donor *Clostridium* species. For instance, in one embodiment, the conjugatively transferable plasmid of the present invention may be selected from any *Clostridium* species. In one embodiment the plasmid is selected from *C. botulinum* serotypes A, B, C, D, E, F or G, or dual neurotoxin producing *Clostridium* strains Ba, Ab, Bf, Af and A(B). The bivalent A(B) strains contain both the BoNT/A and BoNT/B neurotoxin genes; however only BoNT/A is produced, as the BoNT/B neurotoxin gene in this strain contains a premature stop codon and thus is not expressed. In one embodiment, the plasmid pCLL (approximately 48 kb) from the nonproteolytic *C. botulinum* serotype B, strain Eklund 17B was used. In other embodiments, the plasmid may be selected from the group consisting of pBotCDC-A3, pCLJ, pBot81E-1133 and pCLD.

For instance, in on embodiment, conjugative *C. botulinum* plasmids pBotCDC-A3 (proteolytic subtype A3 strain CDC-A3, also referred to in the art as pCLK (SEQ ID NO: 1; GenBank Acc. # CP000963)), pCLJ (SEQ ID NO: 2; GenBank Acc # CP001081) and pCLL (SEQ ID NO: 3; GenBank Acc # CP001057) (tagged with antibiotic resistance markers for tracking purposes) were conjugatively transferred into other proteolytic *C. botulinum* strains, therefore these plasmids or their derivatives may be used for expression of any native or modified *botulinum* neurotoxin, its chains or subfragments or as a complex with its nontoxigenic protein components in any suitable recipient *Clostridium* species. The native toxin gene clusters of the plasmid may be replaced with any gene of interest (including other serotype or subtype native or modified botulinum neurotoxin gene clusters) for expression in the recipient *Clostridium* species.

By "gene of interest" we mean any heterologous or homologous gene capable of being expressed in the recipient *Clostridium* species. By "heterologous" we mean a nucleic acid or protein which is not native to *Clostridium* species. In one embodiment, the gene of interest may include those responsible for expressing clostridial toxins, toxin fragments, or antigenic portions thereof as well as other genes of interest known to one of skill in the art. For instance, the neurotoxin genes encoded on the plasmids pCLK (SEQ ID NO: 1) and pCLJ (SEQ ID NO: 2) are produced in very low quantities in their native hosts, *C. botulinum* strains CDC-A3 and 657Ba, respectively. Since these native BoNT-encoding plasmids pCLK (SEQ ID NO: 1) and pCLJ (SEQ ID NO: 2) are conjugative they may be transferred to a strain of *C. botulinum* that is capable of producing high quantities of neurotoxin, such as the Hall A-hyper strain. The "gene of interest" may also include fragments of the neurotoxin genes as well as other genes within the neurotoxin gene cluster that encode proteins that are and are not part of the botulinum progenitor toxin complex. By "gene of interest", we also mean any gene that is encoded by the genomes of proteolytic or nonproteolytic *C. botulinum* strain or any clostridial species that produces BoNTs including *C. baratii* and *C. butyricum*. Specifically, in one embodiment, the "gene of interest" may be selected from the group consisting of the *C. botulinum* serotypes A, B, C, D, E, F or G, *C. botulinum* strains Ba, Ab, Bf, Af or A(B), BoNT/A3 subtype gene, bont/A3 (pBotCDCA3), the bivalent BoNT/B gene, bont/bvB (pCLJ), and the nonproteolytic BoNT/B gene bont/npB (pCLL).

By "proteolytic" we mean *C. botulinum* strains which do not grow and produce toxin at temperatures below 10° C. By "nonproteolytic" we mean *C. botulinum* strains which can grow and produce toxin at 3.0° C.

The conjugatively transferable plasmid of the present invention is transferred into a recipient *Clostridium* species for expression of the gene of interest in the recipient *Clostridium* species. By "recipient *Clostridium* species" we mean a toxic or nontoxic *Clostridium* species which may be the same or different species as the *Clostridium* species of the plasmid or of the gene or interest. In one embodiment, the plasmid may be from the same *Clostridium* species as the recipient *Clostridium* species, although in other embodiments the plasmid may be from a different *Clostridium* species than the recipient *Clostridium* species. For instance, in one embodiment, transfer of plasmids from nonproteolytic *C. botulinum* to proteolytic *C. botulinum* may occur. In alternate embodiments, plasmids from proteolytic strains may be transferred to nonproteolytic strains *Clostridium* species.

By "toxic *Clostridium* species" we mean a *Clostridium* species which produces BoNT and carries their native BoNT gene on a chromosome. For instance, in one embodiment, the toxic recipient *Clostridium* species may include a *C. botulinum* strain Hall A-hyper which contains a BoNT/A1 neurotoxin gene. Plasmid transfer to this strain may also occur by contacting a BoNT encoding plasmid from a donor strain of the present invention with the recipient *Clostridium* species (i.e., Hall A-hyper) and allowing conjugation to take place, thereby yielding a toxic, recipient strain of Hall A-hyper capable of expressing the recombinant BoNT encoded by the conjugatively transferable plasmid.

By "nontoxic *Clostridium* species" we mean a *Clostridium* species which no longer produce their native BoNT because they no longer carry the BoNT gene or the BoNT gene is inactive. For instance, in one embodiment the nontoxic recipient *Clostridium* species is LNT01. *C. botulinum* strain LNT01 is a nontoxigenic, tetracycline resistant transposon Tn916 mutant of the parent *C. botulinum* subtype A1 strain 62A (subtype A1) that has lost a genome region containing the entire BoNT gene cluster (Johnson et al. 1997). However, other nontoxic recipient strains that may be used in the invention include any nontoxigenic *C. botulinum* strain. For instance, *Clostridium* strains that carry their BoNT genes on extrachromosomal plasmids or bacteriophages can be cured from these elements by several standard genetic techniques known to one of skill in the art. For instance, *C. botulinum* strain CDC-A3, which typically carries a 267 kb BoNT/A3 encoded plasmid, can be cured of its plasmid, resulting in a plasmid-less strain of CDC-A3 (CDC-A3TC5/Tn916) that is thus nontoxic. Other proteolytic *C. botulinum* strains may be constructed in this manner. Nonproteolytic *C. botulinum* strains could also be constructed in a similar fashion.

In one embodiment, the conjugatively transmissible plasmid of the present invention comprises a BoNT-encoding plasmid containing an origin of replication from the native BoNT-encoding plasmids that are effective in *Clostridium* species; and an origin of conjugative transfer from the native BoNT-encoding plasmids capable of modulating the conjugative transfer of the plasmid from a donor *Clostridium* species into a recipient *Clostridium* species, wherein the BoNT encoded by the plasmid is expressed in the recipient *Clostridium* species after transfer by the plasmid. In another embodiment, the conjugatively transmissible plasmid of the present invention comprises a BoNT-encoding plasmid containing an origin of replication from the native BoNT-encoding plasmids that are effective in *Clostridium* species; and an origin of conjugative transfer from the native BoNT-encoding plasmids capable of modulating the conjugative transfer of the plasmid from a donor *Clostridium* species into a recipient *Clostridium* species, wherein the BoNT encoded by the plasmid is expressed in the recipient *Clostridium* species after transfer by the plasmid.

By "BoNT-encoding plasmid" we mean a plasmid encoding proteolytic or nonproteolytic *Clostridium* neurotoxin genes for expressing clostridial toxins, toxin fragments, or antigenic portions thereof. In one embodiment, the BoNT-encoding plasmid is selected from the group consisting of pBotCDC-A3 (proteolytic subtype A3 strain CDC-A3, also referred to in the art as pCLK (SEQ ID NO: 1; GenBank Acc. # CP000963)), pCLJ (proteolytic subtype A4/bivalent B strain 657Ba; GenBank Acc. # CP001081), pBot81E-1133, pCLD (SEQ ID NO:4; GenBank Acc. # CP000964) and pCLL (nonproteolytic serotype B strain Eklund 17B; GenBank Acc. # CP001057).

By "origin of replication" we mean an origin of replication that is functional in a broad range of prokaryotic host cells (i.e., a normal or non-conditional origin of replication such as the ColE1 origin and its derivatives). In one embodiment the origin of replication is effective in *Clostridium* species and may be derived from native BoNT-encoding plasmids.

By "operably joined to a promoter effective in *Clostridium* species" we mean a segment of DNA that comprises sequences capable of providing both promoter and enhancer functions (i.e., the functions provided by a promoter element and an enhancer element. The availability of a *Clostridium* promoter such as is known to the art (see U.S. Pat. No. 5,955,368 to Johnson et al.) makes it possible to incorporate gene of interest into an existing plasmid wherein the resultant plasmid is transferred directly into the recipient *Clostridium* species by conjugative transfer, where the gene will be expressed and the cells of the recipient *Clostridium* species will produce protein. For example, the long terminal repeats of retroviruses contain both promoter and enhancer functions. The enhancer/promoter may be "endogenous" or "exogenous" or "heterologous." An "endogenous" enhancer/promoter is one which is naturally linked with a given gene in the genome. An "exogenous" or "heterologous" enhancer/promoter is one which is placed in juxtaposition to a gene by means of genetic manipulation (i.e., molecular biological techniques) such that transcription of that gene is directed by the linked enhancer/promoter. In one embodiment, the promoter is the native NTNH-BoNT promoter from *C. botulinum*. However, other promoter regions besides the native promoters controlling expression of the toxin and its associated proteins could be potentially introduced in the gene clusters during construction of recombinant genes. Currently, promoters such as those of the ferredoxin or thiolase genes from other clostridial species are used for gene expression in clostridia (Heap et al. 2009).

By "origin of conjugative transfer" we mean a short sequence (typically up to 500 bp) of DNA that is necessary for transfer of the plasmid from a bacterial host to recipient during bacterial conjugation. The oriT is cis-acting—it is found on the same plasmid that is being transferred, and is transferred along with the plasmid. The origin of transfer consists of three functionally-defined domains: a nicking domain, a transfer domain, and a termination domain and facilitates the transfer of plasmids across clostridial species.

By "plasmid derivative" we mean components of the novel conjugative plasmids of the present invention, including but not limited to the origin of replication, which may also be utilized in the construction of *C. botulinum*-specific shuttle vectors useful in the cloning and expression of clostridial toxins, including BoNTs and their protein complexes. For instance, any other *C. botulinum* gene of interest may be cloned into these newly constructed *C. botulinum* specific shuttle vectors. New conjugative expression vectors can be created using the replication and conjugal transfer systems from these native plasmids. This would allow one to reduce the size of these plasmids to facilitate their manipulation. The vectors currently used in our laboratory are derivatives of pJIR1457 and pJIR1456 (Bradshaw et al. 1998; U.S. Pat. No. 5,955,368), pMTL9361 (Pier et al. 2008) and modular clostridial vectors of pMTL80000 series (Heap et al, 2009). These vectors have been useful for the expression and purification of recombinant neurotoxins in a nontoxigenic strain LNT01 or other nontoxigenic *C. botulinum* host strains. Such host strains can be generated by curing the wild type strains from their BoNT-encoded plasmids or by insertionally inactivating or deleting their native BoNT genes located on the chromosome.

Accordingly, the present invention provides the first demonstration of the conjugative transfer of BoNT-encoding plasmids wherein the plasmid is from a toxic *Clostridium* species (i.e., an A3 subtype strain, an A4/bivalent B subtype strain and a nonproteolytic serotype B strain) and is effectively transferred to a non-toxic recipient *Clostridium* species (i.e., a subtype A1 strain) and the BoNT encoded by the plasmid is expressed in the recipient *Clostridium* species. Taken together, this invention provides for the efficient expression of specific genes of interest in *Clostridium* species. For instance, where the gene of interest is a specific *Clostridium* toxin, the novel plasmid and method of the present invention allows one of skill in the art to make any number of clostridial toxins, toxin fragments, or antigenic portions thereof in a clostridial host in a way that ensures abundant expression of the toxin and facilitates purification of said toxin. Furthermore, toxins with altered structures, chimeric toxins, and other toxin derivatives valuable in medicine could be synthesized in this system. Methods for conjugative transfer of the novel plasmids are described in the examples below.

B. Methods of Use.

The present invention also provides for the conjugative transfer of a gene of interest in a recipient *Clostridium* species. The method comprises conjugatively transferring a plasmid comprising an origin of replication effective in *Clostridium* species, a protein coding sequence for a gene of interest operably joined to a promoter effective in *Clostridium* species, and an origin of conjugative transfer capable of modulating the conjugative transfer of the plasmid into the recipient *Clostridium* species, wherein the gene of interest encoded by the plasmid is expressed in the recipient *Clostridium* species.

Methods of using the novel plasmid of the present invention, such as for the manufacture of therapeutic toxins or for the improved expression of pure or designer toxins or toxin fragments, are also envisioned and would be known to one of skill in the art.

III. Examples

The following examples are, of course, offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

Materials and Methods

Bacterial Strains.

Proteolytic *C. botulinum* strains CDC-A3 (BoNT subtype A3), 657Ba (subtype A4/bivalent B), LNT01 (nontoxigenic, subtype A1), Hall A-hyper (subtype A1) and nonproteolytic *C. botulinum* serotype B strain Eklund 17B were obtained from the Johnson laboratory culture collection. *C. botulinum* strain CDC-A3 was originally obtained from the Centers for Disease Control and Prevention (CDC) (Atlanta, Ga.). MLST and PFGE analyses indicated it was genetically identical to subtype A3 strain Loch Maree (Jacobson et al. 2008). *C. botulinum* strain 657Ba was isolated from a case of infant botulism in 1976 (Hatheway et al. 1981). *C. botulinum* strain Eklund 17B was isolated from marine sediments off the coast of Washington (Eklund et al. 1967). *C. botulinum* strain LNT01 is a nontoxigenic Tn916 mutant of the parent strain 62A (subtype A1) (Lin et al. 1991; Johnson et al. 1997). Hall A-hyper is a well characterized subtype A1 strain, which produces high quantities of BoNT/A1 (Brashaw et al. 2004). *Escherichia coli* strains DH10B and CA434 were used for cloning, maintenance and conjugal transfer of the retargeted ClosTron vectors. All *C. botulinum* strains were maintained as frozen stocks at −80° C. in TPGY broth (50 g/liter trypticase peptone, 5 g/liter Bacto peptone, 4 g/liter D-glucose, 20 g/liter yeast extract, 1 g/liter cysteine-HCl, pH 7.4) containing 20% glycerol. Bacterial strains were subsequently cultured anaerobically in TPGY.

Mating Experiments.

Mating experiments were conducted on nonselective TYG (30 g/liter Bacto Tryptone, 20 g/liter yeast extract, 1 g/liter sodium thioglycollate) (4% agar) media and then spread plated onto selective TYG (1.5% agar) plates supplemented with the appropriate antibiotics. Antibiotics were used at the following concentrations: cycloserine (250 µg/ml), sulfamethoxazole (76 µg/ml), thiamphenicol (15 µg/ml), tetracycline (10 µg/ml), erythromycin (2.5 µg/ml), chloramphenicol (25 µg/ml in agar plates and 12.5 mg/ml in broth). All bacterial media components and chemicals were purchased from Becton Dickinson Microbiology Systems, Sparks, Md. and Sigma-Aldrich, St. Louis, Mo.

Plasmid Tagging Using ClosTron.

To ascertain transfer of BoNT-encoding plasmids from the donor to the recipient strain, the plasmids were tagged with an erythromycin resistance gene using the ClosTron mutagenesis system. The ClosTron mutagenesis system (Heap et al. 2004; Heap et al. 2010) was used to insertionally inactivate bont/A3, bont/bvB and bont/npB of plasmids pBotCDC-A3 (strain CDC-A3), pCLJ (strain 657Ba) and pCLL (strain Eklund 17B), respectively. The computer algorithm available through the Targetron (group II intron) Design Site was used to design the PCR primers listed in Table 1 for intron re-targeting of the selected genes bont/A3, bont/bvB and bont/npB. Primers 580|581s-IBS (SEQ ID NO: 5), 580|581s-EBS1d (SEQ ID NO:6), 381|382s-IBS (SEQ ID NO:8), 381|382s-EBS1d (SEQ ID NO:9), 420|421s-IBS (SEQ ID NO:11), 420|421s-EBS1d (SEQ ID NO:12) and EBS Universal (SEQ ID NO:14) (Table 1) were purchased from Sigma-Aldrich (St. Louis, Mo.).

TABLE 1

Oligonucleotide Primers.

| Oligonucleotide Primer | Sequence (5'-3') |
| --- | --- |
| 580\|581s-IBS (SEQ ID NO: 5) | AAAAAAGCTTATAATTATCCTTACAGATCTTACATGTGCGCCCAGATAGGGTG |
| 580\|581s-EBS1d (SEQ ID NO: 6) | CAGATTGTACAAATGTGGTGATAACAGATAAGTCTTACATTTTAACTTACCTTTCTTTGT |
| 580\|581s-EBS2 (SEQ ID NO: 7) | TGAACGCAAGTTTCTAATTTCGGTTATCTGTCGATAGAGGAAAGTGTCT |
| 381\|382s-IBS (SEQ ID NO: 8) | AAAAAAGCTTATAATTATCCTTAGTTCCCCTCGAAGTGCGCCCAGATAGGGTG |
| 381\|382s-EBS1d (SEQ ID NO: 9) | CAGATTGTACAAATGTGGTGATAACAGATAAGTCCTCGAAGATAACTTACCTTTCTTTGT |
| 381\|382s-EBS2 (SEQ ID NO: 10) | TGAACGCAAGTTTCTAATTTCGATTGGAACTCGATAGAGGAAAGTGTCT |
| 420\|421S-IBS (SEQ ID NO: 11) | AAAAAAGCTTATAATTATCCTTAACTGTCAATAAAGTGCGCCCAGATAGGGTG |
| 420\|421S-EBS1d (SEQ ID NO: 12) | CAGATTGTACAAATGTGGTGATAACAGATAAGTCAATAAATTTAACTTACCTTTCTTTGT |
| 420\|421S-EBS2 (SEQ ID NO: 13) | TGAACGCAAGTTTCTAATTTCGATTACAGTTCGATAGAGGAAAGTGTCT |
| EBS Universal (SEQ ID NO: 14) | CGAAATTAGAAACTTGCGTTCAGTAAAC |
| A3KMCT1 (SEQ ID NO: 15) | GAGATCCTGTAAATGGTGTTGATATTGC |
| A3KMCT2 (SEQ ID NO: 16) | GGTATTATCCCTCTTACACATAGCAGC |
| BVBFCT4 (SEQ ID NO: 17) | CAAACAATGATCAAGTTATTTAATAG |
| BVBRCT4 (SEQ ID NO: 18) | TCATTTAAAACTGGCCCAGG |
| NPBFCT11 (SEQ ID NO: 19) | CAAATCAAAACCATTGGGTGAAAAG |
| NPBRCT11 (SEQ ID NO: 20) | CTGGACAAAATTTCATTTGCATTATACCCC |
| AnyBF (SEQ ID NO: 21) | CAGGAGAAGTGGAGCGAAAAAAAG |

TABLE 1-continued

Oligonucleotide Primers.

| Oligonucleotide Primer | Sequence (5'-3') |
|---|---|
| AnyBR (SEQ ID NO: 22) | TGGTAAGGAATCACTAAAATAAGAAGC |
| Erm-F (SEQ ID NO: 23) | CCGATACCGTTTACGAAATTGGAACAGG |
| Erm-R (SEQ ID NO: 24) | TTATTTCCTCCCGTTAAATAATAGATAACT |
| pMTL007-R1 (SEQ ID NO: 25) | AGGGTATCCCCAGTTAGTGTTAAGTCTTGG |

A two-step PCR reaction was used to generate the 350 bp re-targeted intron. The first step included two separate PCR reactions: one containing the IBS and EBS universal primers and the other containing the EBS2 and EBS1d primers. The intron PCR template supplied in the Targetron Gene Knockout System kit (Sigma-Aldrich, St. Louis, Mo.) was used as the DNA template. Five microliters of each PCR product obtained in the first PCR reactions were combined and used as the template in a second PCR reaction containing the IBS and EBS1 d primers. PCR reactions were performed using the GeneAmp High Fidelity PCR system (Applied Biosystems, Foster City, Calif.) under the following conditions: initial hold at 94° C. for 30s; followed by 20 cycles of 15 s of denaturation at 94° C., 30s of primer annealing at 55° C., and 30s of extension at 72° C. and then a final 7 min step at 72° C. The resulting PCR products of 350 bp representing the retargeted intron were purified by gel extraction (Qiagen) and cloned into the vector pMTL007C-E2 (Heap et al. 2010) using restriction endonucleases HindIII and BsrGI by standard cloning techniques (Sambrook 2001).

Transformants containing modified ClosTron vectors were selected from E. coli strain DH10B based on chloramphenicol resistance, and plasmid DNA was isolated using a plasmid minipreparation kit (Fermentas Inc., Glen Burnie, Md.). Plasmids were analyzed by restriction analysis with HindIII and BsrGI, and the correct sequence of the intron was verified by sequencing using the primer pMTL007-R1 (SEQ ID NO: 25) (Table 1). The sequencing primer was purchased from Integrated DNA Technologies, Inc. (Coralville, Iowa). Sequencing reactions were performed using an ABI PRISM BigDye Cycle Sequencing Ready Reaction kit (Applied Biosystems, Foster City, Calif.) then purified according to manufacturer's instructions, and analyzed at the University of Wisconsin Biotechnology Center. The nucleotide sequences were aligned and analyzed with sequence analysis software VectorNTI (Invitrogen, Carlsbad, Calif.).

Plasmid DNA from one of the clones containing the correct intron sequence for targeting each BoNT gene was named pMTL007C-E2:Cbo:bont/A-580s (bont/A3), pMTL007CE2:Cbo:bont/bvB-381s (bont/bvB), and pMTL007C-E2:Cbo:bont/npB-420s (bont/npB) and was transformed into the E. coli conjugation donor strain CA434. Plasmids pMTL007C-E2:Cbo:bont/A-580s, pMTL007CE2:Cbo:bont/bvB-381s, and pMTL007C-E2:Cbo:bont/npB-420s were transferred to C. botulinum strains CDC-A3, 657Ba and Eklund 17B, respectively, by conjugation from E. coli donor strain CA434 as previously described (Heap et al. 2007).

After mating, the bacterial mixture was scraped off of the mating plates, resuspended in 1×PBS (phosphate buffered saline), serially diluted and spread plated onto TYG agar supplemented with cycloserine, sulfamethoxazole (selection of C. botulinum) and thiamphenicol (selection for the vectors). Thiamphenicol resistant colonies were purified by restreaking onto fresh TYG agar supplemented with thiamphenicol. Individual colonies were re-suspended in 1×PBS, serially diluted and plated onto TYG agar containing erythromycin to select for the presence of the spliced Erm-RAM indicating intron integration.

Erythromycin resistant colonies were re-streaked onto fresh TYG agar containing erythromycin. Erythromycin resistant clones were replica plated onto TYG containing thiamphenicol to verify plasmid loss by a thiamphenicol sensitive phenotype. Chromosomal DNA was isolated from randomly selected erythromycin resistant, thiamphenicol sensitive clones as well as from wild type C. botulinum strains using the ChargeSwitch gDNA kit (Invitrogen, Carlsbad, Calif.) following the manufacturer's instructions.

Screening of the clones was performed by PCR using the gene specific primers A3KMCT1 (SEQ ID NO: 15), A3KMCT2 (SEQ ID NO: 16) (bont/A3), BVBFCT4 (SEQ ID NO: 17), BVBRCT4 (SEQ ID NO: 18) (bont/bvB), and NPBFCT11 (SEQ ID NO: 19), NPBRCT11 (SEQ ID NO: 20) (bont/npB) (Table 1) designed to anneal to regions flanking the site of intron integration. PCR was performed with AmpliTaq High Fidelity DNA polymerase, buffer and dNTPs (Applied Biosystems, Foster City, Calif.) using a GeneAmp PCR System 9700 (Applied Biosystems) according to manufacturer's instructions. PCR primers were purchased from Integrated DNA Technologies, Inc. (Coralville, Iowa). PCR products were visualized on 1% Trisacetate-EDTA gels, stained with ethidium bromide and photographed using a Gel Imaging System (BioRad, Hercules, Calif.) with UV transillumination. PCR products were purified using a PCR purification kit (Qiagen, Valencia, Calif.) according to manufacturer's instructions.

The nucleotide sequences of the PCR fragments generated from the wild type and the transconjugant clones were determined using the same primers as for the amplification of the DNA fragments (Table 1). The nucleotide sequences were analyzed as described above.

Tn916 Mutagenesis.

C. botulinum strain Hall A-hyper was chosen for Tn916 mutagenesis to generate tetracycline-resistant strains. The genome sequence of Hall A-hyper is known (GenBank Acc: CP000727). This strain does not contain any plasmids. Tn916 mutant clones of Hall A-hyper were generated using the methods for Tn916 mutagenesis (Lin et al. 1991). This strain containing a tetracycline resistance marker was used as an alternative recipient in the bacterial mating experiments with donors CDC-A3 and 657Ba.

Mating Experiments.

Donor and recipient strains were inoculated into TPGY broth from frozen stocks and incubated anaerobically overnight. The strains were subcultured into TPGY containing 2.5 µg/ml erythromycin (donors) and 10 µg/ml tetracycline (recipients). The donors and recipients were passed again in TPGY broth supplemented with antibiotics and incubated anaerobically for 12 h. Each strain was serially diluted to approximately $10^4$ to $10^5$ CFU/ml in TPGY broth and incubated until an $OD_{600\ nm}$ of 0.6 to 0.8. Matings between donors and recipients were performed on solid nonselective 4% TYG agar. Three different donor to recipient ratios (5:1, 1:1 and 1:5) were tested. Aliquots of 1 ml or 200 µl of donor (D) and recipient (R) cells were centrifuged at 3,000×g for 5 min and resuspended in 200 µl of recipient or donor cells, respectively, and spread plated onto 4% TYG agar. The mating plates were incubated right side up for 12 h at 37° C. or 30° C., depending on the optimal growth temperature of the donor cells. Separate plates spread plated with 200 µl of donor and recipient cells were also included as controls. Sensitivity of plasmid transfer to DNaseI was tested by treating 1 µl of donor cells with DNaseI (100 µg/ml) in a buffer containing 20 mM Tris-HCl, pH 7.5, 1 mM $MgCl_2$ and 1 mM $MgSO_4$ for 37° C. for 60 minutes (Neve et al. 1984). On the nonselective agar plate 25 ml of DNaseI (10 mg/ml) and 50 µl of 50 mM $MgSO_4$ were added, spread evenly and the plates were incubated at room temperature for 60 minutes. Donor cells incubated for 60 min with DNaseI, were spun down at 3,000×g for 5 min. The supernatant was discarded and the cell pellet was re-suspended in 200 µl of the recipient strain. DNaseI (100 µg/ml) and 1 mM $MgSO_4$ were added to the cell mixture and the cells were spread plated onto the TYG agar supplemented with DNaseI and $MgSO_4$. The plates were incubated at 37° C. for 12 h.

Mating experiments were also performed by separating the donor and recipient cells with a 0.45 µm nitrocellulose membrane to determine if cell-to-cell contact is required for plasmid transfer. In these experiments 200 µl of the donor cell suspensions were spotted in the middle of the plate and spread slightly, and plates incubated until all moisture was absorbed. Then nitrocellulose membrane was placed on top of the donor cells, the plates incubated until the membrane completely adhered to the agar, followed by spreading the recipient cells in the middle of the membrane. The mating plates were incubated right side up for 12 hours at 37° C. or 30° C. The recipient cells were then scraped off the surface of the membrane using cell scrapers, the cells were resuspended in the PBS and plated on selective plates.

To assess the possible involvement of bacteriophages in plasmid transfer, donor cell cultures were passed through a 0.45 µm filter (Millipore) and mixed 1:1 with the recipient cell culture (Blaiotta et al. 2000). $CaCl_2$ (1 mM) was added and the mixture was incubated for 12 h at 37° C.

Following matings, the controls and mating mixtures were scraped off of the TYG agar plates and re-suspended in 3 ml of sterile 1×PBS, serially diluted and plated in duplicate on TYG agar supplemented with tetracycline and erythromycin for selection of the transconjugants. Serial dilutions were also spread plated onto TYG supplemented with tetracycline for enumeration of recipients and transconjugants and TYG containing erythromycin for enumeration of donors and transconjugants. The plates were incubated anaerobically for three days at 30° C. or 37° C. The plasmid transfer frequency was calculated as the number of transconjugants per number of donor cells in matings in which the number of donors was greater than the number of recipients. Transfer frequencies were calculated as the number of transconjugants per number of recipient cells when the recipient counts were greater than the donor cell counts.

Colonies resistant to both tetracycline and erythromycin were re-streaked for isolation onto fresh TYG agar supplemented with tetracycline and erythromycin and kept for further analysis.

Pulsed-Field Gel Electrophoresis.

Confirmation of plasmid transfer was performed by pulsed-field gel electrophoresis (PFGE) of nondigested and digested DNA of the transconjugant, donor and recipient strains. C. botulinum strains were inoculated into 10 ml of TPGY and incubated anaerobically at 37° C. (proteolytic strains) or 30° C. (nonproteolytic strains) to an optical density at 600 nm ($OD_{600}$) of 0.6. One milliliter of formaldehyde (Fisher Scientific, Hampton, N.H.) was added, and the cultures were placed on ice for 15 to 30 minutes to inhibit nuclease activity. PFGE plugs were prepared (Johnson et al. 2005).

To increase the visualization of plasmids, pBotCDC-A3-Erm, pCLJ-Erm and pCLL-Erm in the LNT01 transconjugant clones, restriction digests of PFGE plugs were performed using restriction endonucleases chosen to linearize each plasmid. The nucleotide sequences of each plasmid were analyzed using VectorNTI version 10.3 (Invitrogen, Carlsbad, Calif.) and a rare cutting restriction enzyme that cleaves the plasmid once was selected. Restriction enzymes SmaI, XhoI and NarI (New England Biolabs) were selected to digest the PFGE plugs of LNT01 transconjugants to assess the presence of plasmids pBotCDC-A3-Erm, pCLJ-Erm and pCLLErm, respectively. Restriction digests of the PFGE plugs were performed according to the manufacturer's instructions (New England Biolabs). Two sets of nondigested and digested DNA samples were loaded on the same gel and DNA samples were separated by PFGE in a clamped homogenous electric field system (CHEF-DRII; Bio-Rad, Hercules Calif.). After the DNA was transferred onto the nylon membrane, the filter was cut in half, and each portion contained one set of undigested and digested DNA samples. One membrane was hybridized with a neurotoxin gene specific probe, while the other with an erythromycin gene probe.

Southern Hybridizations.

Primers for generation of hybridization probes for ermB (ErmF and ErmR; SEQ ID NOs: 23 and 24 respectively); bont/A3 (A3KMCT1 and A3KMCT2; SEQ ID NOs: 15 and 16 respectively); bont/bvB and bont/npB (AnyB-F and AnyB-R) are listed in Table 1. These gene probes were generated by PCR amplification with an AmpliTaq High Fidelity DNA polymerase, buffer and dNTPs (Applied Biosystems, Foster City, Calif.) using a GeneAmp PCR System 9700 (Applied Biosystems) according to the manufacturer's instructions. The PCR products were purified from agarose gels using the Qiagen gel extraction kit (Qiagen, Valencia, Calif.), and were radioactively labeled with [α-32P] ATP using the Megaprime DNA labeling system (GE Healthcare Bio-Sciences, Piscataway, N.J.).

The DNA samples separated by PFGE were transferred to a positively charged nylon membrane (Immobilon-NY+, Millipore, Bedford, Mass.) overnight by downward capillary transfer in 0.4 M NaOH, 1.5 M NaCl. The membranes were neutralized in 2 M Tris-HCl, pH 7.0 for 15 minutes, rinsed with 2×SSC (3M NaCl, 0.3M sodium citrate) and fixed at 80° C. for 30 minutes under vacuum.

Hybridizations were performed at 42° C. for 16 h in a solution containing 5×Denhardt's Solution, 6×SSPE, 50% formamide, 0.1% SDS, 100 μg/ml herring sperm DNA (Promega, Madison, Wis.) and $^{32}$P-labeled probes at approximately 2×10$^6$ cpm/ml. All hybridization solutions and buffers were prepared according to standard protocols (Sambrook et al. 2001). After hybridizations the membranes were washed twice with 2×SSPE, 0.1% SDS for 5 min each at room temperature and twice with 0.1×SSPE, 0.1% SDS for 30 min each at 42° C. Autoradiography of the membranes was performed for 6-24 h at −70° C. using Kodak BioMax MS film with a BioMax intensifying screen (Eastman Kodak, Rochester, N.Y.).

Plasmid Alignments.

Plasmid sequence alignments were performed to determine the relatedness of the plasmid pCLL (SEQ ID NO: 3) [Acc. No. CP001057] in *C. botulinum* strain Eklund 17B to plasmids, pCP13 (SEQ ID NO: 26) [Acc. No. AP003515] of *C. perfringens* strain 13, pCW3 (SEQ ID NO: 27) [Acc No. DQ366035] of *C. perfringens* strain CW92, pCP8533etx (SEQ ID NO: 28) [Acc. No. AB444205] of *C. perfringens* strain NCTC8533B4D, and two contigs, gcontig_1108490430999 (SEQ ID NO: 29) [Acc. No. ABOO01000010.1] and gcontig_1108490430283 (SEQ ID NO: 30) [Acc. No ABOO01000017] of *C. perfringens* type D strain JGS1721. Plasmid sequence files with annotations were obtained from NCBI. Plasmid alignments were conducted using progressive alignment option of Mauve 2.3.1 (Darling et al. 2004) with the default settings. Plasmid alignments were generated using the Mauve alignment viewer, which illustrates locally collinear blocks (LCBs) as regions without rearrangements in the homologous backbone sequence. LCBs below a plasmid's center line represent the reverse complement orientation relative to the reference genome (pCP13, FIG. 8; pCLL, FIG. 9). Sequence similarity plots are displayed in the LCBs, and the height of the sequence identity plot reflects the average column entropy for the region of the respective alignment. The NCBI blastp tool was used to compare the amino acid sequences of the pCLL ORFs with ORFs in *C. perfringens* strains.

Plasmid Tagging Using ClosTron.

The neurotoxin genes, bont/A3 of plasmid pBotCDC-A3 (strain CDC-A3), bont/bvB of plasmid pCLJ (657Ba), and bont/npB of plasmid pCLL (strain Eklund 17B) were insertionally inactivated using the ClosTron mutagenesis system (Heap et al. 2007; Heap et al. 2010). The potential intron target sites within each neurotoxin gene were identified using the computer algorithm at the group II intron (TargeTron) design site provided by Sigma-Aldrich (St. Louis, Mo.). The target sites chosen for bont/A3, bont/bvB and bont/npB were between nucleotides 580 and 581, 381 and 382, and 420 and 421 on the sense strands, respectively. Each re-targeted intron was amplified by PCR and cloned into the ClosTron vector pMTL007C-E2 between restriction sites HindIII and BsrGI (Heap et al. 2010) resulting in constructs, pMTL007C-E2:Cbo:bont/A-580s, pMTL007CE2: Cbo:bont/bvB-381s, and pMTL007C-E2: Cbo:bont/npB-420s. The constructs were transferred to their respective wild-type strains CDC-A3, 657Ba and Eklund 17B by conjugation from the *E. coli* donor strain CA434.

Following matings, the cells were plated onto agar containing thiamphenicol to select for *C. botulinum* clones harboring the ClosTron vector. Thiamphenicol-resistant transconjugants of *C. botulinum* containing the ClosTron vector were then plated onto agar supplemented with erythromycin for selection of intron integrants, since the erythromycin resistance gene is restored upon integration of the group II intron (Heap et al. 2007; Heap et al. 2010). Next, erythromycin-resistant clones were screened for the loss of the intron vector by replica plating, then erythromycin-resistant and thiamphenicol-sensitive clones were selected and further analyzed by PCR to determine whether the intron had integrated into its desired target site. The gene specific PCR primers (Table 1) were designed to anneal to regions flanking the insertion site for each neurotoxin gene in order to amplify the entire insertion element.

Insertion of the re-targeted introns into either the bont/A3, bont/bvB or bont/npB genes was confirmed by PCR analysis (FIG. 1). PCR amplification of the DNA from the wild type CDCA3 strain using the bont/A3 gene specific primers A3KMCT1 (SEQ ID NO:15) and A3KMCT2 (SEQ ID NO: 16) produced a PCR product of 1,264 bp (FIG. 1, Lane 1), whereas a DNA fragment of 3,044 bp was observed in the CDCA3 transconjugant clones analyzed (FIG. 1, Lanes 2 and 3), indicating integration of the intron element (approximately 1.8 kb) into the target gene. Similarly, amplification of the 657Ba and Eklund 17B transconjugant clones (FIG. 1, Lanes 5 and 6, and Lanes 8 and 9, respectively) using bont/bvB and bont/npB gene specific primers yielded expected PCR products that exhibited an approximately 1.8 kb increase in size compared to the PCR fragments generated from the wild type 657Ba (FIG. 1, Lane 4) and Eklund 17B (FIG. 1, Lane 7). These results confirmed that the re-targeted introns containing the erythromycin resistance determinant ermB were inserted into the bont/bvB and bont/npb (FIG. 1). Furthermore, the PCR fragments amplified from the tagged BoNT-encoding plasmids were sequenced and it was confirmed that the introns had inserted correctly into the chosen target sites within the neurotoxin genes in all three plasmids.

To verify that the plasmids were tagged, pulsed-field gel electrophoresis (PFGE) of nondigested DNA samples from the wild type strains CDC-A3, 657Ba and Eklund 17B, and the clones carrying the tagged plasmids pBotCDC-A3-Erm, pCLJ-Erm and pCLL-Erm, was performed followed by Southern hybridization analyses using probes specific to ermB and the respective neurotoxin genes. Hybridization signals were observed with the plasmid bands in all strains using the neurotoxin gene probes (FIG. 2). Hybridization of the ermB probe was detected with the tagged plasmid clones but not with the wild type strains, indicating that the plasmids were successfully tagged with the ErmB-RAM. The resultant strains with their tagged plasmids CDC-A3580s1 (pBotCDC-A3-Erm), 657BaCT4 (pCLJ-Erm) and Eklund 17BCT11 (pCLL-Erm) were used as the donors in the mating experiments.

Plasmid transfer was confirmed by pulsed-field gel electrophoresis of digested DNA of transconjugant and wild type *C. botulinum* strains. *C. botulinum* strains were inoculated into 10 ml of TPGY and incubated anaerobically at 37° C. (proteolytic strains) or 30° C. (nonproteolytic strains) to an optical density at 600 nm (OD$_{600}$) of 0.6. One milliliter of formaldehyde (Fisher Scientific) was added and the cultures were placed on ice for 15 to 30 minutes to inhibit nuclease activity and PFGE plugs were prepared (Johnson et al. 2005).

To increase the visualization of virulence plasmids, pCLK-Erm, pCLJ-Erm, and pCLL-Erm in the LNT01 transconjugant clones restriction digests of PFGE plugs were performed using restriction endonucleases chosen to linearize each plasmid. The nucleotide sequences of each plasmid were analyzed using VectorNTI version 10.3 (Invitrogen, Carlsbad, Calif.) and a rare cutting restriction enzyme that cleaves the plasmid once was selected. Restriction enzymes SmaI and XhoI (New England Biolabs), were selected to digest the PFGE plugs of LNT01 transconjugants to assess the presence of plasmids pCLK-Erm and pCLJ-Erm, respectively. Plasmid pCLL is quite smaller (approximately 48 kb) than pCLK and pCLJ, and finding an enzyme that only linearizes the plasmid without over digestion of the chromosome was challenging. Based on the nucleotide sequence of pCLL, the restriction enzyme NarI was chosen. Restriction digests of the PFGE plugs was performed according to the manufacturer's instructions (New England Biolabs). The digested DNA samples were separated by PFGE in a clamped homogenous electric field system (CHEF-DRII; Bio-Rad, Hercules Calif.).

PFGE plugs were prepared for several LNT01 transconjugants that were obtained from each mating experiment to confirm the transfer of each virulence plasmid to the recipient C. botulinum strain LNT01. The PFGE plugs were digested with restriction enzymes designed to linearize each plasmid so that it could be easily visualized in the ethidium bromide stained gel. PFGE analysis of the LNT01 transconjugants from all three separate matings is shown in FIG. 1. Each bacterial strain exhibits a unique restriction banding pattern when digested with a particular restriction enzyme. Digestion of PFGE plugs of LNT01, CDC-A3580s1, 657BaCT4-2 and Eklund 17BCT11-1 all exhibit unique restriction banding patterns when digested with SmaI, XhoI or NarI (FIG. 3). The restriction banding pattern of wild type LNT01 when digested with SmaI was identical to that of the transconjugants except that the banding pattern of all transconjugant clones contained an approximately 270 kb DNA band corresponding to the presence of pCLK-Erm (FIG. 3A). The presence of pCLJ-Erm was revealed as a approximately 270 kb DNA band in the transconjugant LNT01 clones, which exhibited restriction banding patterns that were otherwise identical to LNT01 (FIG. 3B). To separate the DNA fragments in the approximately 48 kb range, the gel loaded with the DNA samples of wild-type LNT01, Eklund 17BCT11-1 and the LNT01 transconjugant clones being analyzed for the presence of pCLL-Erm, was electrophoresed with a pulse-time of 1-5 s. Under these conditions the presence of pCLL-Erm migrating to a position in the gel corresponding to its approximate linear size of approximately 48 kb in the DNA samples of the LNT01 transconjugant clones was clearly observed. This analysis confirmed the transfer of plasmid pCLL-Erm from a non-proteolytic C. botulinum serotype B strain to a proteolytic C. botulinum nontoxigenic Tn916 mutant subtype A1 strain LNT01.

Mating Experiments.

Separate mixed plate matings between each donor strain, CDCA3580s1 (pBotCDC-A3-Erm), 657BaCT4 (pCLJ-Erm), and Eklund 17BCT11 (pCLL-Erm) and recipient strains LNT01 and Hall A-hyper/Tn916 mutant were performed inside an anaerobic chamber on solid 4% agar TYG media for 12 h. Initially, strain LNT01 was used as the recipient to determine if plasmids pBotCDC-A3-Erm, pCLJ-Erm, and pCLL-Erm could be transferred to a recipient C. botulinum strain. Several mating experiments were performed to optimize the mating conditions to establish the transfer frequencies. Since similar transfer frequencies were observed when matings were performed for 12 or 24 h (data not shown); all subsequent bacterial mating experiments were incubated for 12 h. The mating pairs between proteolytic strains were performed at their optimal growth temperature of 37° C. Matings of the nonproteolytic serotype B donor strain Eklund 17BCT11 and the recipient strain LNT01 were performed at 30° C., which is the optimal growth temperature for nonproteolytic C. botulinum strains, since higher transfer frequencies were observed at this temperature (data not shown). Three different donor to recipient ratios (5:1, 1:1 and 1:5) were tested, the donor:recipient (D:R) ratio of 1:1 yielded the highest transfer frequencies. After the mating conditions were established in LNT01 the same experimental parameters were used to evaluate the transfer frequencies of C. botulinum plasmids into C. botulinum strain Hall A-hyper/Tn916 mutant.

Transconjugants were selected by plating the mating mixtures onto TYG agar supplemented with erythromycin (selection of Erm-plasmid) and tetracycline (selection of recipient strain LNT01 or Hall A-hyper/Tn916. To determine the number of donors and recipients the mating mixtures were also plated onto TYG containing either erythromycin (donors) or tetracycline (recipients). The number of donor cells and recipients varied with respect to the mating pairs (Table 2). The transfer frequency was calculated as the number of transconjugants per recipient or donor depending on which strain had the highest CFU/ml.

The transfer frequency values are displayed in Table 2. Overall, the plasmid transfer frequencies were lower than those reported for plasmids found in strains of C. perfringens (Hughes et al. 2007; Rood et al. 1978; Brynestad et al. 2001). The conjugation frequencies for pBotCDC-A3-Erm and of pCLJ-Erm increased markedly when Hall A-hyper/Tn916 was used as the recipient. Similar conjugation frequencies of plasmid pCLL from the nonproteolytic strain Eklund 17B were observed when either strain LNT01 or Hall A-hyper/Tn916 was used as recipient (Table 2). In one embodiment, D:R ratios of 1:1, 5:1 and 1:5 were tested to determine the optimum ratio for plasmid transfer. A slight increase in the conjugation frequency was observed when a ratio of 1:1 was used over the ratio of 5:1. When a D:R ratio of 1:5 was used a significant decrease in the number of transconjugants was observed. An approximately 4-log reduction in the number of CFU/ml of donors CDC-A3580s1 and 657BaCT4-2 was observed during matings with LNT01.

TABLE 2

Transfer of C. botulinum BoNT-encoding plasmids to recipient strains LNT01 and Hall A-hyper/Tn916.

| Donor | Plasmid | Recipient (LNTO1) | Recipient (Hall A-hyper/Tn916) |
|---|---|---|---|
| CDC A3580 | pBotCDC A3 Erm | $1.5 \times 10^{-8} \pm 1.2 \times 10^{-8a}$ | $1.8 \times 10^{-6} \pm 9.4 \times 10^{-7b}$ |
| 657Ba-CT4 | pCLJ-Erm | $1.4 \times 10^{-6} \pm 1.1 \times 10^{-6a}$ | $1.7 \times 10^{-5} \pm 1.2 \times 10^{-5a}$ |
| Eklund 17BCT11 | pCLL-Erm | $1.5 \times 10^{-7} \pm 1.4 \times 10^{-7a}$ | $4.5 \times 10^{-7} \pm 2.8 \times 10^{-7a}$ |

Transfer frequencies were calculated as the number of tranconjugants per [a]recipient or [b]donor and are reported as the averages of at least three replicate experiments.

Pre-incubation of the donor cells with DNaseI, by combined addition of DNaseI to the agar medium and to the mating mixtures did not inhibit plasmid transfer, and the transfer frequencies were similar to that of matings in which DNaseI was not added. Furthermore, no transductants were obtained in matings performed with the filtered culture supernatants of each donor strain and the whole cell culture of the recipient strain LNT01. Importantly, no transconjugants were obtained when matings were performed in which the donors and recipients were separated by a 0.45 μm nitrocellulose membrane.

Confirmation of BoNT-Encoding Plasmid Transfer.

PFGE was performed using nondigested samples and samples digested with restriction enzymes designed to linearize each BoNTencoding plasmid. PFGE analysis of digested samples allowed us to use the unique restriction banding patterns of the strains as a genetic screen to visually determine whether the plasmids were transferred to the recipient strains. PFGE analyses of the recipient LNT01, donor strains and LNT01 transconjugants from three separate matings are shown in FIGS. 4-6. LNT01 (recipient), wild type and plasmid-tagged donor strains, and three clones of each transconjugants all exhibited unique restriction banding patterns when digested with SmaI, XhoI or NarI PFGE followed by Southern hybridization analyses using the ermB probe (intron probe) and the appropriate neurotoxin gene probes showed that the tagged plasmids were transferred to the recipient strains (FIGS. 4-6).

Transfer of pBotCDC-A3-Erm from CDC-A3 (donor) to LNT01 (recipient) is shown in FIG. 4. When PFGE is performed on nondigested C. botulinum DNA samples most of the DNA remains trapped in the wells because large circular DNA molecules that are nicked or enzymatically relaxed fail to enter the gel matrix (Beverley 1988). Linear forms of plasmids are able to migrate through the gel to a position which corresponds to their linear size relative to a reference marker (Beverley 1988). In addition, a small portion of sheared chromosomal DNA migrating a short distance from the well position is frequently observed in PFGE analysis of nondigested clostridial DNA (Marshall et al. 2007). The DNA restriction banding pattern of the wild type strain LNT01 (FIG. 4, lane 7A) digested with SmaI was identical to that of the transconjugants (FIG. 4, lanes 10-12A), except that the banding pattern of all transconjugants clones contained an additional band of approximately 270 kb. This band corresponds by size to the plasmid, pCDC-A3-Erm in the donor strain (FIG. 4A, lanes 2, 3 and 8, 9). This approximately 270 kb band was observed in digested (FIG. 4, lanes 10-12) and nondigested (FIG. 4, lanes 4-6) samples of the transconjugants hybridized with both bont/A3 (FIG. 4C, lanes 4-6, 10-12) and ermB probes (FIG. 4B, lanes 4-6, 10-12). These results confirmed the transfer of the tagged plasmid containing the intron interrupted bont/A3 gene. The same plasmid band in the donor strains hybridized with the bont/A3 probe (FIG. 4C, lanes 2, 3, 8, 9), but only the tagged donor hybridized with the ermB probe (FIG. 4B, lanes 3 and 9). No hybridization signals were detected with either probe in the recipient strain LNT01. PFGE of digested samples of the transconjugant and donor strains (FIG. 4A, lanes 8-12) showed an increase in the intensity of the approximately 270 kb band in the ethidium bromide stained gel as well as produced stronger hybridization signals with the neurotoxin gene (FIG. 4C, lanes 8-12) and ermB (FIG. 4B, lanes 9-12) probes, while the hybridization signals at the well positions decreased. This indicated that the plasmid was linearized by the restriction enzyme and migrated into the gel.

Similarly, transfer of the approximately 270 kb plasmid, pCLJ-Erm, from the donor strain 657BaCT4 to LNT01 (FIG. 5), and the approximately 48 kb plasmid, pCLL from Eklund 17BCT11 to LNT01 was confirmed (FIG. 6). Furthermore, transfer of plasmids pBotCDC-A3-Erm, and pCLJ-Erm to Hall A-hyper/Tn916 was also confirmed by PFGE and Southern hybridization analyses (FIG. 7).

Plasmid Alignments.

The genome alignment tool Mauve (Darling et al. 2004) was used to generate global alignments of C. botulinum plasmid pCLL (SEQ ID NO:3) (strain Eklund 17B) and C. perfringens plasmid pCP13 (SEQ ID NO: 26) (strain 13). Alignment of plasmids pCLL and pCP13 (FIG. 8) revealed 16 locally collinear blocks (LCBs) A3 probe (FIG. 8C: lanes 2, 3, 8, 9), with at least some portion of them found in pCP13. The LCB shown (FIG. 8) encompassed a region of 11ORFs which exhibited the highest degree of sequence homology with similar ORFs found on plasmid pCP13. The Mauve program was also used to generate global alignments of pCLL and C. perfringens plasmids pCW3 (SEQ ID NO: 27), pCP8533etx (SEQ ID NO: 28), and two contigs of C. perfringens type D strain JGS1721 (gcontig_1108490430283 [SEQ ID NO: 30] and gcontig_1108490430999 [SEQ ID NO: 29]). The alignments revealed several locally collinear blocks (LCBs) with at least some portion of them found in the C. perfringens plasmids (FIG. 9). Two neighboring LCBs shown were of particular interest because they shared homology with the conjugative C. perfringens plasmids. The region that contained the tcp locus common to C. perfringens conjugative plasmids is represented by the LCB (FIG. 9). The corresponding LCB observed in pCLL shares some sequence homology with this region as indicated in FIG. 9, however this region is truncated. The LCB of plasmid pCLL contains a gene that encodes for a putative type IV secretion system protein VirD4 (pCLL_0005). Comparison of homologous ORFs of pCLL and C. perfringens plasmids is presented in Table 3.

TABLE 3

Comparison of predicted ORFs of pCLL with plasmids of C. perfringens.

| pCLL Locus | Putative Function of pCLL gene product | Funciton of closest C. perfringens relative of gene product, strain and/or identity | Size (aa) | Coding Sequence position |
|---|---|---|---|---|
| pCLL_0004 | Hypothetical protein | Hypothetical protein, C. perfringens pCP13, PCP53, and conserved hypothetical, C. perfringens E str. JGS1987, CPC_A0335, 53/78 (67%) | 78 | 717-953 |
| pCLL_0005 | VirD4 component | TraG/TraD family, C. perfringens D str. JGS1721, CJD_A0258, 383/747 (51%) | 739 | 1017-3236 |
| pCLL_0006 | Hypothetical protein | Putative membrane protein, C. perfringens C str. JGS1495, CPC_A0332, 162/353 (45%), hypothetical protein C. perfringens pCP13, PCP50, 162/353 (45%) | 711 | 3241-5376 |

TABLE 3-continued

Comparison of predicted ORFs of pCLL with plasmids of *C. perfringens*.

| pCLL Locus | Putative Function of pCLL gene product | Funciton of closest *C. perfringens* relative of gene product, strain and/or identity | Size (aa) | Coding Sequence position |
|---|---|---|---|---|
| pCLL_0007 | Hypothetical protein | Hypothetical protein, *C. perfringens* pCP13, PCP49, 47/87 (54%) | 91 | 5377-5652 |
| pCLL_0008 | Hypothetical protein | Hypothetical protein, *C. perfringens* pCP13, PCP48, 66/124 (53%) | 138 | 5764-6402 |
| pCLL_0009 | Hypothetical protein | Conserved hypothetical, *C. perfringens* C str. JGS1495, CPC_A0328, 406/627 (64%) | 637 | 6458-8371 |
| pCLL_0010 | Hypothetical protein | Hypothetical protein, *C. perfringens* pCP13, PCP45, 55/161 (34%) | 167 | 8373-9053 |
| pCLL_0011 | Probable cell wall-binding protein | Probable cell wall-binding protein, *C. perfringens* E str. JGS1987, AC3_A0050, 224/370 (60%), TcpG, *C. perfringens* C str. JGS1495, CPC_A0146, 83/134 (61%) | 389 | 9114-10283 |
| pCLL_0012 | Hypothetical protein | Conserved hypothetical protein, *C. perfringens* D str. JGS1721, CJD_1944, 106/267 (39%) | 270 | 10302-11114 |
| pCLL_0013 | Hypothetical protein | Conserved hypothetical protein, *C. perfringens* C str. JGS1495, CPC_A0323, 42/82 (51%) | 91 | 11397-11672 |
| pCLL_0014 | Hypothetical protein | Conserved hypothetical protein, *C. perfringens* D str. JGS1721, CJD_A0233, 48/123 (39%) | 136 | 11678-12088 |
| pCLL_0015 | Hypothetical protein | Conserved hypothetical protein, *C. perfringens* C str. JGS1495, CPC_A0321, 200/377 (53%) | 379 | 12102-13241 |
| pCLL_0016 | Hypothetical protein | Conserved hypothetical protein, *C. perfringens* D str. JGS1721, CJD_A0227, 55/116 (47%) | 365 | 13267-14388 |
| pCLL_0017 | Conserved hypothetical protein | Hypothetical protein, *C. perfringens* str. 13 pCP13, PCP34, 31/74 (41%) | 171 | 14453-14968 |
| pCLL_0040 | Resolvase/recombinase | Resolvase/Recombinase, *C. perfringens* D str. JGS 1721, CJD_1891, 78/210 (37%) | 210 | 33462-34094 |
| pCLL_0042 | Site-specific recombinase resolvase family | DNA-invertase, *C. perfringens* CPE str. F4969, AC5_A0225, 80/191 (41%) | 181 | 34265-34810 |
| pCLL_0045 | Replication protein | Replication protein, *C. perfringens* B str. ATCC 3626, AC1_A0161, 164/388 (42%) | 446 | 35980-37320 |
| pCLL_0047 | Putative ATPase | Putative ATPase, *C. perfringens* E str. JGS1987, AC3_0198, 145/302 (48%) | 297 | 38545-39438 |
| pCLL_0048 | Hypothetical protein | Hypothetical protein, *C. perfringens* E str. JGS1987, AC3_0197, 21/41 (51%) | 119 | 37431-39790 |
| pCLL_0051 | Putative LexA repressor | LexA repressor, *C. perfringens* B str. ATCC 3626, AC1_A0290, 34/78 (43%) | 235 | 40570-41277 |
| pCLL_0053 | Hypothetical protein | Conserved hypothetical protein, *C. perfringens* B str. ATCC 3626 AC1_A0334, 33/105 (31%) | 120 | 41747-42109 |
| pCLL_0056 | Cell wall binding repeat domain protein | Cell wall binding repeat domain protein, *C. perfringens* D str. JGS1721, CJD_0682, 83/183 (45%) | 152 | 42953-47533 |

The numbering for the coding sequence position starts at position 1. There are total of 56 ORFs in the pCLL plasmid, but only those that showed homology with *C. perfringens* ORFs are listed in Table 3. Any protein sequences for these ORFs are available from GenBank (http://www.ncbi.nlm-.nih.gov.ezproxy/nuccore/CP001057).

Results.

The present invention provides BoNT-encoding plasmids capable of conjugatively transferring genetic information of interest among other *Clostridium* species (where the plasmid is from the same *Clostridium* species, as well as where the plasmid is from different *Clostridium* species). Mating experiments were conducted between *Clostridium* species harboring a BoNT-encoding plasmid and a nontoxigenic *C. botulinum* strain LNT01 as the recipient. Plasmids from *C. botulinum* strains CDC-A3 and 657Ba, plasmids pBotCDC-A3 (267 kb) and pCLJ (270 kb), respectively, were selected to represent proteolytic *Clostridium* species. Plasmid pCLL (48 kb) from *C. botulinum* serotype B, strain Eklund 17B was selected as a representative of nonproteolytic *Clostridium* species. The recipient strain LNT01 was selected because it is nontoxigenic, and it contains a tetracycline resistance marker due to presence of the transposon Tn916 on the genome.

To ascertain transfer of the plasmids from the donor *Clostridium* species to the recipient *Clostridium* species, the plasmids were tagged with an antibiotic resistant gene, wherein the antibiotic resistant gene confers resistance to antibiotics selected from the group consisting of erythromycin, tetracycline, chloramphenicol or thiamphenicol. While any antibiotic resistant gene may be used, the present examples used the erythromycin resistance gene via the ClosTron mutagenesis system. The antibiotic resistance gene inserted on the plasmids is required only to track the plasmid transfer from the donor *Clostridium* species to the recipient *Clostridium* species, and is not required for plasmid maintenance in the recipient *Clostridium* species. The example above demonstrates that positive selection of transconjugants was facilitated by the presence of the tetracycline resistance determinant in combination with erythromycin resistance provided by the tagged plasmids.

Discussion.

Early studies attempting to demonstrate plasmid-associated BoNT genes were unsuccessful, except for discovery of the plasmid-borne BoNT/G gene (Zhou et al. 1995). The recent finding of plasmids in *C. botulinum* serotypes A and B housing BoNT/A, BoNT/B or both BoNT/A and BoNT/B genes (Marshall et al. 2007; Smith et al. 2007) prompted surveys of serotype B strains (Franciosa et al. 2009; Umeda et al. 2009) and dual neurotoxin *C. botulinum* strains producing subtypes Bf, Af and Ab BoNTs (Marshall 2009; Franciosa et al. 2009). These studies have invigorated interest in the field of plasmid biology in *C. botulinum*. The present invention demonstrates that plasmids encoding BoNTs can be transferred to other *Clostridium* species.

Specifically, the present invention therefore provides BoNT-encoding plasmids (such as pBotCDC-A3 and pCLJ from two proteolytic *Clostridium* species), and pCLL from a nonproteolytic *Clostridium* species, to other proteolytic *Clostridium* species, providing a novel conjugatively transferable plasmid capable of transferring BoNT-encoding plasmids to other recipient *Clostridium* species. Transductants were not obtained when the recipient cells were incubated with filtered donor culture supernatants, demonstrating that bacteriophages were not involved in BoNT gene transfer. Furthermore, since BoNT gene transfer was not inhibited by the addition of DNaseI, and no transconjugants were obtained during matings in which the donor and recipient cells were separated by a 0.45 μm filter, cell-to-cell contact is required for the transfer of these plasmids (demonstrating that plasmid transfer across *Clostridium* species is likely due to conjugation or a conjugation-like mechanism rather than by transformation).

Previously, *C. perfringens* was the only *Clostridium* described to harbor plasmids capable of intraspecies conjugative transfer (Hughes et al. 2007; Rood et al. 1978; Byrnestad et al. 2001; Rood et al. 2004; Bannam et al. 2006). Here, conjugative transfer of plasmid pCLL from the nonproteolytic *C. botulinum* serotype B strain Eklund 17B to a proteolytic *C. botulinum* strain supports interspecies transfer since proteolytic and nonproteolytic groups have long been considered to comprise different *Clostridium* species based on different genomic, genotypic and phenotypic characteristics (Carter et al. 2009; Peck et al. 2009).

Intraspecies conjugal transfer of plasmids in *C. perfringens* has been reported to be a highly efficient process with conjugation frequencies of $10^{-1}$ to $10^{-2}$ transconjugants per donor (Hughes et al. 2007; Rood et al. 1978; Byrnestad et al. 2001). Conversely, the conjugation frequencies for the *C. botulinum* plasmids tested in this study were much lower ranging from $10^{-5}$ to $10^{-8}$ (Table 2). *C. botulinum* strain LNT01 was initially selected as a recipient, since it is nontoxigenic and contained the tetracycline resistance marker for positive selection of transconjugants. Although each of the plasmids was successfully transferred to LNT01, we observed a decrease in the number of donor cells during matings. For example, an approximately 4-log reduction in the number of CFU/ml of donors CDC-A3580s1 and 657BaCT4-2 was observed during matings with LNT01. A possible explanation may be that strain LNT01 produces a bacteriocin (unpublished data) that could inhibit the growth or kill the donor cells. *C. perfringens* strain F4969 was also reported to produce a bacteriocin which interfered with the transfer of plasmid pMRS4969 from this strain to the recipient *C. perfringens* strain because the bacteriocin greatly inhibited or killed the recipient cells (Byrnestad et al. 2001).

Interestingly, only a 1-2 log reduction of donor (CFU/ml) was observed when the nonproteolytic *C. botulinum* strain Eklund 17BCT11 was used as the donor. To further investigate if a plasmid-endoded bacteriocin affected transfer efficiencies, another *C. botulinum* strain (Hall A-hyper/Tn916) that does not contain any plasmids nor a plasmid encoded-bacteriocin similar to those identified in *C. botulinum* strains ATCC 3502 (Acc. No. AM412318) (Sebaihia et al. 2007) and 213B (Dineen et al. 2000), was tested as a recipient. The plasmid transfer frequency of pCLJ and pBotCDC-A3 into Hall A-hyper/Tn916 increased by at least a log compared to that of LNT01 as a recipient while the transfer frequency of pCLL from the nonproteolytic strain Eklund 17B was similar when both recipients were tested (Table 2).

*C. botulinum* strain CDC-A3 is identical to strain Loch-Maree based on MLST (Jacobson et al. 2008) and PFGE analyses (Marshall 2009), and it is highly likely that the plasmids are identical in both strains. The nucleotide sequences of pCLK (SEQ ID NO: 1) (strain Loch Maree, A3), pCLJ (SEQ ID NO: 2) (strain 657Ba, A4) and pCLL (SEQ ID NO: 3) (strain 17B) genome sequences have been deposited in GenBank (Hughes et al. 2007). Although plasmids pCLK and pCLJ share significant sequence homology, the sequence of plasmid pCLL is unrelated to pCLJ and pCLK (Marshall 2009; Hill et al. 2009). Detailed sequence analysis of the botulinum gene clusters of plasmids pCLK and pCLJ have been performed, but little emphasis has been given to the functions of other plasmid genes (Smith et al. 2007). Most of the ORFs of these plasmids are described as putatively encoding hypothetical or conserved hypothetical proteins. The mechanism for plasmid replication is unknown, because gene homologues involved in typical rolling-circle or theta replication have not been identified on these plasmids (Smith et al. 2007). Similarly, the mechanism of plasmid transfer is also unknown, but genes homologous in plasmids pCLK and pCLJ that may be involved in plasmid transfer are suggested by the genome annotations. For example, TraK analogs (CLK_A0294; CLJ_A0213) and TraG/D (CLK_A0293; CLJ_A0212) flanked by hypothetical ORFs, as well as genes that encode for putative type II and type IV secretion system proteins, such as pili, have been described.

Figure 8:
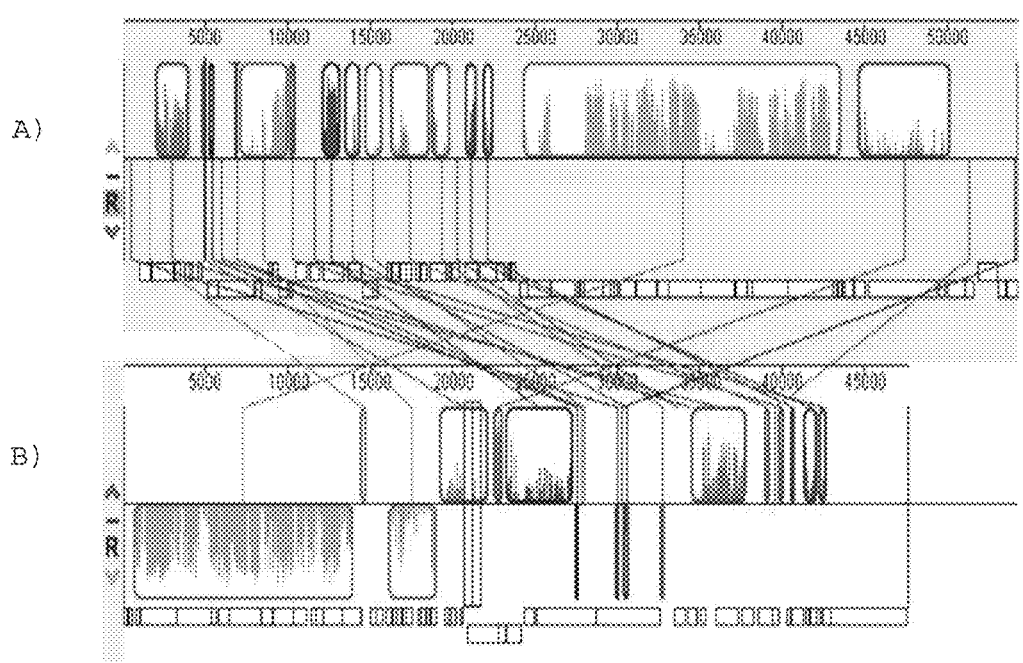
FIG. 8. Plasmid alignment of (A) pCP13 (C. perfringens strain 13) and (B) pCLL (C. botulinum strain Eklund 17B). The alignment has two panels, one for each complete plasmid: pCP13 [top position] and pCLL [bottom position]. The top portions of the panels are composed of colored segments corresponding to the boundaries of locally collinear blocks (LCBs) with lines connecting the homologous blocks in each plasmid. LCBs below a plasmid's centerline are in the reverse complement orientation relative to the reference plasmid (pCP13). The lower portion of the panels represent the predicted open reading frames (ORFs) for the corresponding segments of double stranded DNA with ORFs on top representing top strand and below (bottom strand).

Plasmid pCLL of nonproteolytic *C. botulinum* serotype B strain Eklund 17B is approximately 48 kb in size and contains 56 putative ORFs. As mentioned above, pCLL does not exhibit homology with sequenced plasmids in proteolytic *C. botulinum* strains. Therefore, homology searches of pCLL were performed with genome sequences of other clostridial species. Initially, a nucleotide sequence alignment of pCLL with pCP13 of *C. perfringens* strain 13 was performed using Mauve. Surprisingly, this analysis identified regions of homology between pCLL and pCP13, which are graphically displayed as colored locally collinear blocks (LCBs) (FIG. 8). More detailed BLAST analyses revealed eleven ORFs within the gold-colored LCB (CLL_0004 to CLL_0017) with a range of identity from 34 to 67% with ORFs of plasmid pCP13 (Table 3). Considering that pCP13 is not a conjugative plasmid, further sequence analyses were performed between pCLL and completed sequences of conjugative *C. perfringens* plasmids and draft genome sequences of several *C. perfringens* strains.

Interestingly, two conjugative *C. perfringens* plasmids pCW3 (SEQ ID NO: 27) and pCP8533etx (SEQ ID NO: 28) as well as two contigs representing potential plasmids in a type D strain were identified by the Mauve program to contain regions homologous to pCLL (SEQ ID NO:3) (FIG. 9). The Mauve program revealed two LCBs, which represented regions of pCLL homologous to the *C. perfringens* nucleotide sequences. The LCB encompassed the tcp (Transfer of *Clostridium* Plasmids) locus common to conjugative *C. perfringens* plasmids (Bannam et al. 2006). Although plasmid pCLL does not seem to contain the entire tcp locus, it does carry genes that encode for proteins that exhibit 61% (CLL_0011) identity to TcpG (CPC_A0146 of *C. perfringens* C strain JGS1495) (Bannam et al. 2006). The ORF pCLL_0005 (a putative VirD4 homolog) in the LCB showed 51% identity to CJD_A0258 (a putative VirD4 component) of *C. perfringens* type D strain JGS 1721. Further BLAST analyses revealed that *C. perfringens* type D strain JGS 1721 contained several ORFs with identities ranging from 37%-51% with ORFs of pCLL (Table 3). *C. perfringens* type D strains carry several plasmids ranging in size from approximately 48 to 110 kb. These strains produce both alpha-toxin (plc gene) and epsilon-toxin (etx gene). The epsilon toxin is ranked third in potency following BoNTs and tetanus neurotoxin (Smedley et al. 2005). *C. perfringens* type D strains that produce alpha-toxin and epsilontoxins, but not the enterotoxin (cpe gene) or the beta 2 toxin (cpb2 gene) have been reported to carry the etx gene on a plasmid of 48 kb (Sayeed et al. 2007). The etx plasmid in *C. perfringens* type D strain JGS 1721 also contains the tcp locus (Sayeed et al. 2007). The draft genome sequence of *C. perfringens* strain JGS 1721 consists of 221 contigs. The pCLL ORFs shared homology with 16 and 8 ORFs within two of these contigs, gcontig_1108490430999 (SEQ ID NO: 29) and gcontig_1108490430283 (SEQ ID NO:30), respectively. Interestingly, gcontig_1108490430283 carries the genes that encode for etx and the tcp locus.

Overall, homology searches revealed that BoNT-encoding plasmid pCLL of the nonproteolytic *C. botulinum* strain exhibited some degree of homology with both conjugative and nonconjugative plasmids in *C. perfringens*. The presence of BoNT genes on conjugative plasmids in both proteolytic and nonproteolytic strains of *C. botulinum* is highly significant and could facilitate the dissemination of neurotoxin genes to other species of clostridia. It is conceivable that BoNT-encoding plasmids were involved in the transfer of BoNT/E and BoNT/F genes to *C. butyricum* and *C. baratii*.

In summary, the present invention provides for the first time the novel conjugative transfer of proteolytic and nonproteolytic *C. botulinum* plasmids encoding BoNT genes to other proteolytic *C. botulinum* strains. Since BoNT is the most potent toxin known, BoNT gene transfer to other bacteria could lead to the generation of new pathogens of high impact, such as emergence of new BoNT-forming clostridia with resistant phenotypes, and strains with higher spore heat resistance than *C. botulinum*. The finding that pCLL of the nonproteolytic *C. botulinum* serotype B strain contains gene regions that are homologous with plasmids in *C. perfringens* is intriguing and illustrates the potential transfer of plasmids to other clostridial species.

Identification of Botulinum Neurotoxin Genes on a Plasmid in *C. Botulinum* Bf Strains.

Bacterial Strains.

The *C. botulinum* strains were obtained from the Johnson laboratory culture library and are listed in Table 4.

TABLE 4

| BoNT genes on plasmids in *C. botulinum* strains. | | | | | |
|---|---|---|---|---|---|
| | Neurotoxin gene | | Virulence plasmid | | |
| Strain | Serotype | Location | Name | Size (kb) | Source or reference[a] |
| 81E-1133 | B | Plasmid | pBot81E-1133 | ~190 | This study |
| | F | Plasmid | pBot81E-1133 | ~190 | This study |
| 3281(32419) | B | Plasmid | pBot3281 | ~260 | This study |
| | F | Plasmid | pBot3281 | ~260 | This study |
| 84 | A2 | Chromosome | | | This study |
| | F | Chromosome | | | This study |
| ATCC 3502 | A1 | Chromosome | | | Sebaihia |
| 5328A | A1 | Chromosome | | | Mars. Raphael |
| KyotoF | A2 | Chromosome | | | Mars.&Smit |
| Loch Maree | A3 | Plasmid | pCLK | 266,785 | Mars&SMit |
| 657Ba | A4 | Plasmid | pCLJ | 270,346 | Mars.&Smit |
| | B | Plasmid | pCLJ | 270,346 | Mars and Smith |
| OkraB | B | Plasmid | pCLD | 148,780 | Smith et al. |
| 14842 | B | Plasmid | pBot14842 | ~260 | This study |
| 10068 | B | Plasmid | pBot10068 | ~48 | This study |
| 17B | B | Plasmid | pCLL | 47,642 | GenBank (CP001056) |
| Alask E | E | Chromosome | | | GenBank (CP001078) |

TABLE 4-continued

BoNT genes on plasmids in *C. botulinum* strains.

| Strain | Serotype | Neurotoxin gene Location | Virulence plasmid Name | Size (kb) | Source or reference[a] |
|---|---|---|---|---|---|
| Langeland F | F | Chromosome | | | GenBank (CP000728) |
| 4852 | F | Chromosome | | | This study |

[a]Source or reference for determination of plasmid or chromosomally encoded neurotoxin genes BoNT Strain Af 84 is a soil sample isolate from the Mendoza province in Argentina (Gimenez 1978), and strains Bf 81E-1133 and Bf 3281(32419) were isolated from separate cases of infant botulism in New Mexico, USA (Hatheway 1987). *C. botulinum* strains representing four BoNT/A subtypes (A1-A4) and proteolytic and nonproteolytic serotypes B and F were included in the PFGE and Southern blot analyses for comparison with the Bf and Af subtype strains. All strains were maintained as frozen stocks at −80° C. in TPGY broth (50 g/liter trypticase peptone, 5 g/liter Bacto peptone, 4 g/liter D-glucose, 20 g/liter yeast extract, 1 g/liter cysteine-HCl, pH 7.4) supplemented with 40% glycerol. Bacterial strains were subsequently cultured anaerobically in TPGY broth sparged with nitrogen gas prior to autoclaving.

The prevalence of virulence plasmids appears to be highest among proteolytic and nonproteolytic serotype B strains (Franciosa et al. 2009). In agreement with other reports, plasmids of nonproteolytic serotype B strains are significantly smaller than the virulence plasmids found in proteolytic serotype B and bivalent strains analyzed (FIG. 10A). Plasmids of approximately 48 kb were consistently observed in several nonproteolytic serotype B strains (FIG. 10A; unpublished data), whereas the plasmids in bivalent and proteolytic B strains ranged in size from approximately 148 kb to 270 kb (FIG. 10A). Whole genome sequencing of the nonproteolytic serotype B strain 17 B has been completed (GenBank Acc. No. CP001056) and the presence of virulence plasmid pCLL (47.6 kb) has been confirmed in this study and by other researchers (Franciosa et al. 2009). The new virulence plasmid, pBot10068 identified in the nonproteolytic serotype B strain 10068, was similar in size (approximately 48 kb) to plasmid pCLL (FIG. 10). No other plasmids of nonproteolytic serotype B strains have been sequenced, but it is likely that they are highly homologous, since virulence plasmids of consistent size (approximately 48 kb) are common among nonproteolytic serotype B strains (unpublished data; Franciosa et al. 2009).

Attempts to align pCLL (SEQ ID NO: 3) (17B) with pCLD (SEQ ID NO: 4) (Okra B) using the MAUVE software were not successful, indicating that the plasmids are not sufficiently related. The only homologous regions identified between these two plasmids using the comparison tools at the Pathema-*Clostridium* website were the type B neurotoxin gene clusters. The physiological and metabolic properties of proteolytic and nonproteolytic *C. botulinum* strains vary. Thus, it is not surprising that these strains carry plasmids that differ significantly in size as well as in gene content. The relatedness of plasmids found in nonproteolytic *C. botulinum* strains to the plasmids in other toxigenic clostridia remains to be determined.

Pulsed-Field Gel Electrophoresis.

Bacterial strains were inoculated into 10 ml of TPGY and incubated anaerobically at 37° C. to an optical density at 600 nm ($OD_{600}$) of 0.6. Formaldehyde was added to inhibit nuclease activity, and the PFGE plugs were prepared as described (Johnson et al. 2005). Restriction digests of PFGE plugs were performed using restriction endonucleases AatII, ApaI, BglI, EagI, NaeI, NarI, NnuI, PvuII, RsnII, SacII, SalI, SfiI, SmaI and XhoI, (New England Biolabs) according to the manufacturer's instructions. Digested and nondigested DNA samples were separated by PFGE in a clamped homogenous electric field system (CHEF-DRII; Bio-Rad, Hercules Calif.) under the following conditions: pulse time 1-30 seconds, 6 V/cm, at 14° C. for 24 h.

Hybridization Probes.

Regions of the light chain (LC) of the BoNT/A, BoNT/B and BoNT/F genes were amplified by PCR using the primers listed in Table 5 to generate DNA fragments for hybridization probes.

TABLE 5

Oligonucleotide primers used in PCR and sequencing reactions.

| Gene | Amplicon length (bp) | Primer name | Primer sequence (5' - 3') |
|---|---|---|---|
| Primers used to generate hybridization probes | | | |
| bont/A | 268 | bontAF6[a] (SEQ ID NO: 31) | GCTACTAATGCATCACAGGCAGGCG |
| | | bontAR6[a] (SEQ ID NO: 32) | CCCATGAGCAACCCAAAGTCC |
| bont/B | 592 | bontBF1[a] (SEQ ID NO: 33) | TTTGCATCAAGGGAAGGCTTCG |
| | | bontBR1[a] (SEQ ID NO: 34) | AGGAATCACTAAAATAAGAA |
| bont/F | 1317 | CLP10F (SEQ ID NO: 35) | AGAGAGCTCATGCCAGTTGTAATAAATAG |
| | | CLP10R (SEQ ID NO: 36) | AGAAGATCTCTTTGTACCTTTTCTAGGAA |

TABLE 5-continued

Oligonucleotide primers used in PCR and sequencing reactions.

| Gene | Amplicon length (bp) | Primer name | Primer sequence (5' - 3') |
|---|---|---|---|
| Primers used for sequencing of the neurotoxin genes | | | |
| bont/A2 | | CLP2R (SEQ ID NO: 37) | AGAAGACTCTTATTGTATCCTTCATCTA |
| | | CLP3F (SEQ ID NO: 38) | AGAGGATCCGCATTAAATGATTTATGTATCAAAG |
| | | CLP3R (SEQ ID NO: 39) | AGACTGCAGCAGTGAACTTTCTCCCCATC |
| | | HC/A2a (SEQ ID NO: 40) | CTGTATTTGGTACTTTTGCA |
| | | HC/A2b (SEQ ID NO: 41) | CGATAGAGTATATTATGATTCAATA |
| | | HC/A2c (SEQ ID NO: 42) | GGTAGCGTAGTGACTACAAA |
| | | 12243F (SEQ ID NO: 43) | GGATGATATGTAATAATGATATGTC |
| | | 12804F (SEQ ID NO: 44) | GGACCCTCAGCTGATATTATACAG |
| | | 13328R (SEQ ID NO: 45) | TCCAGATGTATCTTCAGATAGGAG |
| | | 13940R (SEQ ID NO: 46) | ATTAGGCATAGGCTCTAATTGGCC |
| | | 14681R (SEQ ID NO: 47) | AGCGCTATTTATAGACTCATTAAG |
| | | 15418R (SEQ ID NO: 48) | TTAGTTAGTCTATTATTAGTGATAG |
| | | 16337R (SEQ ID NO: 49) | ATACATAGCAATACTCATATTAG |
| bont/F | | FNTNHF (SEQ ID NO: 50) | GGATGATATGTAATAATGAAAGCAAC |
| | | CLP10F (SEQ ID NO: 35) | AGAGAGCTCATGCCAGTTGTAATAAATAG |
| | | CLP10R (SEQ ID NO: 36) | AGAAGATCTCTTTGTACCTTTTCTAGGAA |
| | | LC/Fa (SEQ ID NO: 51) | CAGAGATTGACTTAGCAAAT |
| | | F711R (SEQ ID NO: 52) | CCGTATAATCCATGCAGTGCATGTATC |
| | | F750F (SEQ ID NO: 53) | AGCAAGCACCTCTTATGATAGCCG |
| | | F1702R (SEQ ID NO: 54) | CGATTCTTCTGATAATCGTGTATC |
| | | CLP11F (SEQ ID NO: 55) | AGAGGATCCGCGCCACCGCGACTATGCATTAGAGTA |
| | | CLP11R (SEQ ID NO: 56) | AGACTGCAGGTTTTCTTGCCATCCATGCT |
| | | HC/Fa (SEQ ID NO: 57) | AATATAGGTAATGAGGTACAAA |
| | | HC/Fb (SEQ ID NO: 58) | ATTAAATGATTTAGTGACTAGTACT |
| | | HC/Fc (SEQ ID NO: 59) | AATGGAAATTTAATAGATGAA |
| | | F2106F (SEQ ID NO: 60) | GTTGGATAGTATCAAATTGGCTTAC |
| | | F2729F (SEQ ID NO: 61) | ATAGTGGTAAGCTTAGTGAAGTT |
| | | F2826R (SEQ ID NO: 62) | GGAATCCTTACCCAGAAACTAATAC |
| | | F3198R (SEQ ID NO: 63) | CCAACATATCTTGTATCATTACAACC |
| | | F3245F (SEQ ID NO: 64) | GTGATGAGCCAGATCCAAGTATC |
| | | F3260F (SEQ ID NO: 65) | AGTGATGAGCCAGATCCAAGTATC |
| | | F3506F (SEQ ID NO: 66) | GGCGATCTGGCATACATTAATGTAG |
| | | KM425R (SEQ ID NO: 67) | CTGGTACATATGTTAATGATAGCCATTCC |

[a]Referenced in Marshall et al. 2007

PCR primers were purchased from Integrated DNA Technologies, Inc. (Coralville, Iowa), and PCR reactions were performed using the GeneAmp High Fidelity PCR system (Applied Biosystems, Foster City, Calif.). PCR conditions were optimized for each primer pair utilized. Total genomic DNA was isolated from *C. botulinum* strains Loch Maree, 657Ba, Bf 81E-1133 and Af 84 using the ChargeSwitch gDNA Mini Bacteria kit (Invitrogen, Carlsbad, Calif.) according to the manufacturer's instructions, and used as templates in PCR. The PCR products were purified from agarose gels using the Qiagen gel extraction kit (Qiagen, Valencia, Calif.), and were radioactively labeled with [α-$^{32}$P]ATP using the Megaprime DNA labeling system (GE Healthcare Bio-Sciences, Piscataway, N.J.).

Southern Hybridizations.

The DNA samples separated by PFGE were transferred to a positively charged nylon membrane (Immobilon-NY+, Millipore, Bedford, Mass.) overnight by downward capillary transfer in 0.4 M NaOH, 1.5 M NaCl. The membranes were neutralized in 2 M Tris-HCl, pH 7.0 for 15 minutes, rinsed with 2×SSC (3M NaCl, 0.3M sodium citrate) and fixed at 80° C. for 30 minutes under vacuum. Hybridizations were performed at 42° C. for 16 h in a solution containing 5×Denhardt's Solution, 6×SSC, 50% formamide, 0.1% SDS, 100 g/ml herring sperm DNA (Promega, Madison, Wis.) and $^{32}$P-labeled probes at 2×10$^6$ cpm/ml. All hybridization solutions and buffers were prepared according to standard protocols (Sambrook and Russell, 2001). After hybridizations, the membranes were washed twice for 5 min, at room temperature with 2×SSC, 0.1% SDS and twice for 15 min each at 42° C. Autoradiography of the membranes was performed for 16-18 h at −70° C. using Kodak BioMax MS film with a BioMax intensifying screen (Eastman Kodak, Rochester, N.Y.).

Plasmids carrying neurotoxin genes have been identified in numerous *C. botulinum* strains of serotypes A and B, and in bivalent subtypes Ba and Ab (Marshall et al., 2007; Smith et al., 2007; Franciosa et al., 2009). Here pulsed-field gel electrophoresis (PFGE) and Southern hybridization analysis identified four new virulence plasmids, one in the proteolytic serotype B strain 14842 (pBot14842; approximately 260 kb), one in the nonproteolytic serotype B strain 10068 (pBot10068; approximately 48 kb), and two bivalent Bf subtype strains Bf 3281 (pBot3281; approximately 260 kb) and Bf 81E-1133 (pBot81E-1133; approximately 190 kb). The plasmids identified in the Bf subtype strains differ significantly in size and harbor genes encoding for BoNT/bvB and BoNT/bvF. The presence of two neurotoxin genes on the same plasmid is a phenomenon which has been described for the megaplasmid pCLJ found in strain 657Ba (Marshall et al. 2007; Smith et al. 2007) and for plasmids recently identified in three bivalent Ab strains (Franciosa et al. 2009). The identification of two additional virulence plasmids each harboring different neurotoxin subtype genes supports the hypothesis that plasmids serve as vehicles for the transfer of these genes to other *C. botulinum* strains and are responsible for the generation of dual neurotoxin producing strains.

Results.

Both BoNT/A4 and BoNT/bvB genes were found to be located on the same plasmid in the bivalent *C. botulinum* strain 657Ba. PFGE is a genetic typing method that has been used as an epidemiological tool to assess the genetic diversity of a variety of bacterial pathogens. PFGE was utilized as a method to identify large plasmids in nondigested DNA samples of Bf subtype strains Bf 81E-1133 and Bf 3281 (32419) and the Af subtype strain 84. Strains representing four serotype A subtypes (A1-A4), and proteolytic and nonproteolytic serotypes B and F were included in the analysis for comparison with the Bf and Af subtype strains (FIGS. 10-11). For example, the proteolytic and nonproteolytic serotype B strains Okra B and 17B and the bivalent strain 657Ba were included in this analysis as positive controls because they contain the virulence plasmids pCLD, pCLL and pCLJ, respectively (Smith et al. 2007; Marshall et al. 2007; Franciosa et al. 2009). To determine whether the neurotoxin genes are located on plasmids observed in the PFGE gels, Southern blot analyses were performed using probes designed to hybridize to all subtypes of BoNT/A, BoNT/B and BoNT/F genes.

In all PFGEs of nondigested DNA samples a significant portion of the DNA remained in the wells representing intact chromosomal DNA (FIGS. 10A and 11A). Beneath the well position was a band of sheared chromosomal DNA, characteristic of *C. botulinum* strains due to their high nuclease activity. Faint bands of DNA were observed beneath the sheared chromosomal DNA that represented linear plasmid DNA molecules.

The subtype A3 (Loch Maree) and A4 (657Ba) strains were included as positive controls and their plasmids pCLK (267 kb) and pCLJ (270 kb) were observed in the ethidium bromide stained gel beneath the prominent band corresponding to sheared chromosomal DNA (FIG. 11A). As expected hybridization signals with the BoNT/A gene probe occurred with the plasmids in the A3 (Loch Maree) and A4 (657Ba) subtype strains (FIG. 11B). Nucleotide bands similar in size to pCLK (Loch Maree) and pCLJ (657Ba) were observed for both serotype B strain 14842 and strain Af 84 (FIG. 11A). The proteolytic serotype B strain 14842 was included in the PFGE analysis of Af 84 as a negative control and as expected hybridization signals were not detected with either BoNT/A or BoNT/F gene probes (FIGS. 11B, C). Hybridization with type A and F neurotoxin gene probes produced signals that were observed only at the well position and at the level of sheared chromosomal DNA in strain Af 84 indicating that both type A and F neurotoxin genes are located on the chromosome in this strain (FIG. 11B, C).

Plasmids were observed in the PFGE of nondigested DNA of proteolytic and nonproteolytic serotype B strains and bivalent Bf strains Bf 81E-1133 and Bf 3281(32419) (FIG. 10A). A new virulence plasmid was identified in the nonproteolytic serotype B strain 10068 that was similar in size (approximately 48 kb) to pCLL of strain 17B. PFGE analysis of nondigested DNA of several other nonproteolytic strains revealed that all carried similarly sized plasmids (approximately 48 kb) (data not shown). Conversely, plasmids among proteolytic serotype B strains were found to be much larger; ranging in size from approximately 150 kb to 270 kb. Plasmid DNA molecules of varying sizes were observed in the bivalent Bf strains Bf 81E-1133 and Bf 3281(32419) (FIG. 10A).

Hybridization of the BoNT/B gene probe was observed with the 270 kb plasmid, pCLJ (657Ba), the 148 kb plasmid pCLD (Okra B), and the ~48 kb plasmid pCLL (17B), as expected. Hybridization with the BoNT/B gene probe was also detected with two newly identified plasmids, one in the nonproteolytic B strain 10068 (pBot10068), and one in the proteolytic B strain 14842 (pBot14842) (FIG. 10B).

Interestingly, both BoNT/B and BoNT/F gene probes produced strong hybridization signals with the approximately 260 kb DNA band in *C. botulinum* strain Bf 3281 (32419) (FIG. 10B, C), indicating that both neurotoxin genes in this strain are encoded on the same plasmid. The same neurotoxin gene probes produced weak hybridization signals with the 190 kb DNA band in *C. botulinum* strain Bf 81E-1133, suggesting that the BoNT/B and BoNT/F genes may reside on a plasmid in this strain. However, strong hybridization signals were also detected at the well position and at the level of sheared chromosomal DNA (FIG. 10B, C), which could indicate chromosomal BoNT gene location. Thus, in order to accurately determine the location of the neurotoxin genes in this strain, chromosomal DNA was digested with 16 different rare cutting restriction enzymes. Based on the nucleotide sequences of pCLK (SEQ ID NO: 1) (Loch Maree) and pCLJ (SEQ ID NO: 2) (657Ba) restriction enzymes were chosen based on their potential to linearize the plasmid in strain Bf 81E-1133, cleave it more than once, or not at all. The digested DNA was separated by PFGE (FIG. 11A), and Southern hybridizations of the PFGE gel was performed using probes specific to BoNT/B (FIG. 11B) and BoNT/F (FIG. 11C) genes.

Several of the restriction enzymes chosen did not cleave the plasmid at all since the hybridization signals detected were similar to those observed with nondigested DNA samples (FIG. 11B, C). Six restriction enzymes resulted in an increase in the hybridization signals with both BoNT/B and BoNT/F gene probes with the approximately 190 kb DNA band, while hybridization signals at the well positions decreased (FIG. 11B, C). This clearly demonstrates that the BoNT/B and BoNT/F neurotoxin genes are located on the same plasmid of approximately 190 kb in C. botulinum strain Bf 81E-1133 (FIG. 11).

Unlike the Bf subtype strains, the BoNT/A2 and BoNT/F genes were determined to be located on the chromosome in C. botulinum strain Af 84, despite the presence of a large (approximately 240 kb) plasmid in this strain (FIG. 10A).

DNA Sequencing and Analysis.

The nucleotide sequences were determined for the BoNT/A and BoNT/F genes in C. botulinum strain Af 84 using the oligonucleotide primers listed in Table 4 to establish the subtype of each neurotoxin. Sets of overlapping PCR fragments were generated for both BoNT/A and BoNT/F genes. The nucleotide sequences were determined on both strands of the PCR fragments derived from two separate PCR experiments. Sequencing reactions were performed using the ABI PRISM BigDye Cycle Sequencing reaction kit (Applied Biosystems), and the sequences were determined using an Applied Biosystems 3730×1 automated DNA sequencing instrument at the University of Wisconsin-Madison, Biotechnology Center. The nucleotide sequences were aligned and analyzed with sequence alignment software Vector NTI version 10.3 (Invitrogen, Carlsbad, Calif.).

Sequence analysis of the BoNT/A gene of strain Af 84 confirmed that it is a BoNT/A2 subtype gene, as previously reported (Hill et al. 2007). Furthermore, strain Af 84 is genetically related to other C. botulinum subtype A2 strains KyotoF and FRI-H1A2 (Hill et al. 2007). The gene encoding NTNH has been reported as chimeric in several proteolytic C. botulinum strains and was suggested to be a hot spot for recombination (Hutson et al. 1996; East et al. 1996; Jovita et al. 1998; Smith et al. 2007). Santos-Buelga et al. 1998 characterized the BoNT/bvB and BoNT/bvF gene clusters of strain Bf 3281(32419) and showed that although the BoNT/F neurotoxin gene was more similar to the nonproteolytic BoNT/F of strain 202F, the NTNH of the BoNT/bvF cluster shared a higher degree of sequence identity to the NTNH of proteolytic strains Langeland F and KyotoF (subtype A2).

Plasmid Alignments.

Figure 15:
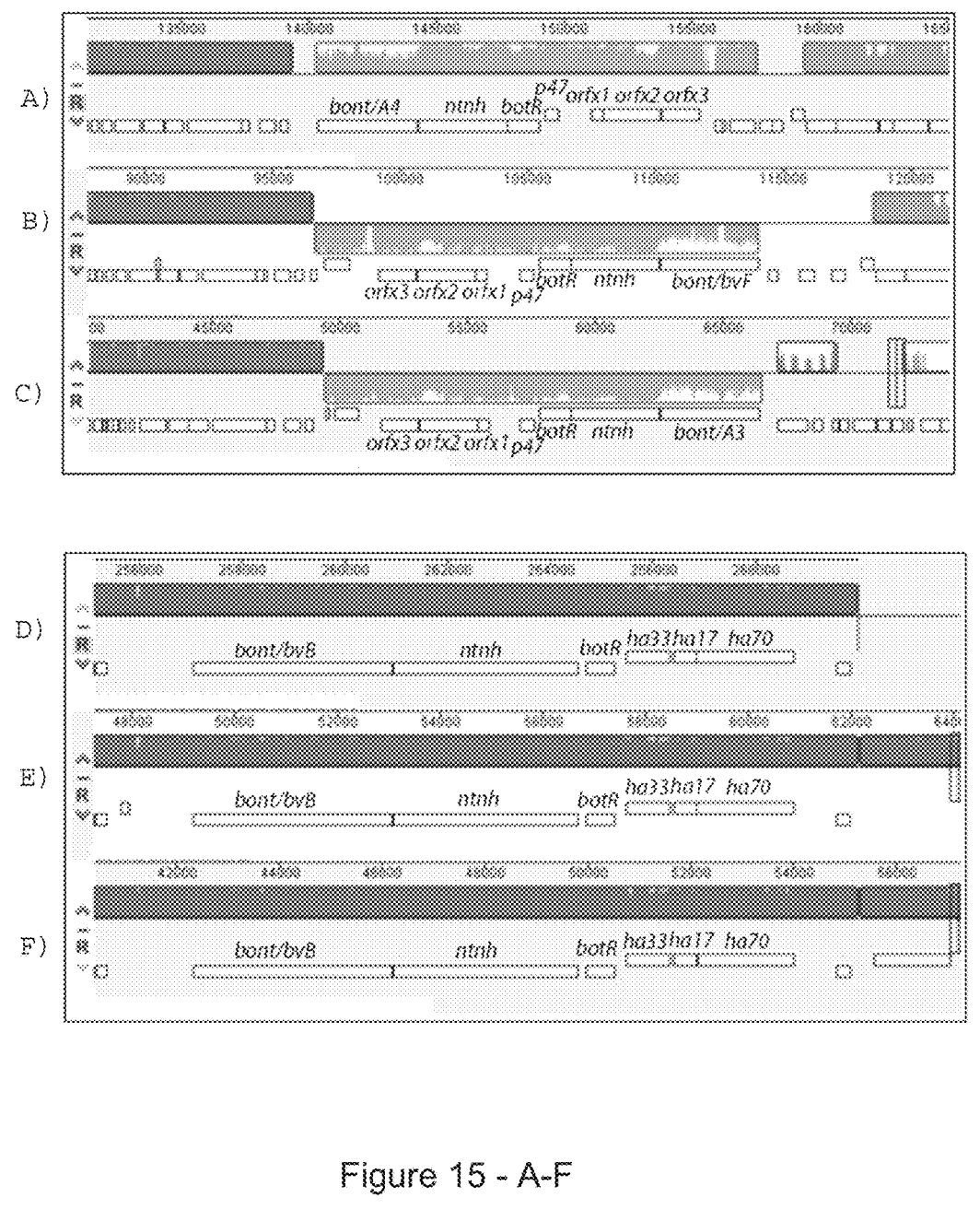

Plasmid sequence alignments were performed to determine the relatedness of the plasmid in strain Bf 81E-1133 to known plasmids in other proteolytic C. botulinum strains. Plasmid sequence files with annotations were obtained from NCBI for plasmids pCLK (strain Loch Maree) and pCLD (strain Okra B) and the draft sequence of pCLJ (strain 657Ba) was generously provided by Theresa Smith (USAMRIID). For strain Bf 81E-1133, contigs 18 (SEQ ID NO: 68; containing the BoNT/bvB gene) and 23 (SEQ ID NO: 69; containing the BoNT/bvF gene) were obtained from NCBI ABDP01000018 and ABDP01000023, respectively. Plasmid alignments were conducted using the progressive alignment option of Mauve 2.2.0 (Darling et al. 2004) with the default settings (FIG. 12). Figures were generated using the Mauve alignment viewer, which illustrates locally collinear blocks (LCBs) as regions without rearrangements in the homologous backbone sequence. LCBs below a plasmid's center line represent the reverse complement orientation relative to the reference genome (pCLK for alignments shown in FIGS. 13-14, pCLJ for alignments shown in FIG. 15). Sequence similarity plots are displayed in the LCBs, and the height of the sequence identity plot reflects the average column entropy for the region of the respective alignment (Darling et al. 2004).

Results.

The genome alignment tool Mauve was used to generate global alignments of three C. botulinum plasmids pCLK (Loch Maree), pCLJ (657Ba) and pCLD (Okra B) with two contigs from the draft genome of C. botulinum strain Bf 81E-1133. A total of 71 contigs (4,217,949 bp) representing the draft genome for strain Bf 81E-1133 were ordered using Mauve with either the chromosome of C. botulinum strain Okra B or strain Langeland F as the reference genome to sift out contigs comprised of prospective plasmid regions. Contigs 18 and 23 were identified as potential plasmid regions, based on the lack of alignment to whole genomes of strains Okra B and Langeland F (data not shown). Contig 18 (SEQ ID NO: 68) contained the BoNT/B gene, and contig 23 (SEQ ID NO: 69) contained the BoNT/F gene. Alignment of plasmids pCLK (SEQ ID NO: 1), pCLD (SEQ ID NO: 4), and pCLJ (SEQ ID NO:2) with Bf81E-1133 contigs 18 and 23 (FIG. 13) revealed eight locally collinear blocks (LCBs) with at least some portion of them found in pCLK (SEQ ID NO: 1), pCLJ (SEQ ID NO:2), and pCLD (SEQ ID NO: 4). The LCB containing the BoNT/A gene cluster for pCLK, pCLJ, and the BoNT/F gene cluster for contigs 18 and 23 also identified a region in pCLD that contained a small degree of sequence similarity although this plasmid lacks either BoNT/A or BoNT/F toxin gene clusters. In backbone view, the alignment of plasmids pCLK, pCLD, and pCLJ with Bf 81E-1133 contigs 18 and 23, identified regions conserved in only two out of four of the plasmid files, and also regions conserved in three out of four of the plasmid files (FIG. 14).

For BoNT gene cluster analysis, alignments were generated using pCLJ, pCLK, and Bf 81E-1133 contig 23 for BoNT/A and BoNT/bvF gene clusters (FIG. 15A), or pCLJ, pCLD, and Bf contig 18 for the BoNT/B cluster (FIG. 15B). The LCB containing the BoNT/bvF cluster in Bf 81E-1133 (contig 23) and the BoNT/A3 cluster in pCLK is in the reverse complement orientation relative to the BoNT/A4 cluster in pCLJ. The alignment viewer was magnified to observe the similarity of the ORFs in both toxin gene cluster types, and revealed that the greatest amount of sequence variation occurred primarily between the neurotoxin genes rather than the other ORFs in the toxin gene clusters. When viewed in the backbone view (FIG. 16), islands were identified that were unique to either Bf 81E-1133 (contigs 18 and 23) and pCLJ or Bf 81E-1133 (contigs 18 and 23) and pCLK, but none of these correspond to regions contained in the ORFs of the toxin cluster. Analysis of the BoNT/B gene cluster revealed a conserved sequence with high sequence identity for the entire LCB that contains the ORFs for the B toxin cluster (FIG. 15B).

Surprisingly, a region of the BoNT/F NTNH of strain Bf 81E-1133 spanning 277 amino acid residues was found to be homologous to the corresponding region of the NTNH of Alaska E (Table 6).

TABLE 6

Amino acid identities of regions of the BoNT/F NTNH of *C. botulinum* strain Bf 81E-1133.

| Strain | % Identity of amino acid residues of NTNH | | | |
|---|---|---|---|---|
| | 1-294 | 295-572 | 573-1131 | 1132-1168 |
| 657Ba[a] | 99.0 | 76.0 | 91.0 | 63.8 |
| Loch Maree[b] | 88.8 | 76.0 | 96.8 | 72.2 |
| Alaska E[c] | 83.3 | 89.9 | 80.8 | 52.8 |
| Langeland F[d] | 90.8 | 80.5 | 92.1 | 88.0 |
| 202 F[e] | 72.7 | 72.0 | 86.0 | 88.0 |

[a]NTNH of BoNT/A4 cluster
[b]NTNH of BoNT/A3 cluster
[c]NTNH of BoNT/E cluster
[d]NTNH of proteolytic BoNT/F cluster
[e]NTNH of nonproteolytic BoNT/F cluster The BoNT/E gene cluster is located on the chromosome in strain Alaska E (Acc: CP0001078), but isolates of *C. butyricum* producing type E neurotoxin have been associated with four cases of infant botulism (Aureli et al. 1986; McCroskey et al. 1986) suggesting the lateral transfer of the neurotoxin gene. Hauser et al. 1992 suggested the type E neurotoxin gene was located on a plasmid in two *C. butyricum* isolates, however other researchers have reported the toxin gene being chromosomally encoded in toxigenic strains of *C. butyricum* (Zhou et al. 1993; Wang et al. 2000). The acquisition of the BoNT/E gene by toxigenic isolates of *C. butyricum* is presently unknown.

Sequence Analysis of the BoNT/bvF NTNH of Strain Bf 81E-1133.

Pairwise comparisons of the amino acid sequences of the nontoxic nonhemagglutinin (NTNH) of the BoNT/bvF cluster of strain Bf 81E-1133 with the NTNH of several strains of serotype A, strains of proteolytic and nonproteolytic serotypes B and F and the nonproteolytic serotype E strain Alaska E were performed using the AlignX (ClustalW) module of Vector NTI version 10.3 (Invitrogen, Carlsbad, Calif.).

The BoNT/A gene of *C. botulinum* strain Af 84 has been reported as an A2 subtype (Hill et al. 2007). However, the nucleotide sequences of BoNT/A and BoNT/F have not been determined. Thus, nucleotide sequencing of the BoNT/A and BoNT/F genes of strain Af 84 was conducted to establish each neurotoxin subtype. The BoNT/A gene exhibited 100% identity to BoNT/A2 of *C. botulinum* subtype A2 strain KyotoF at the nucleotide and amino acid level (data not shown) and was confirmed to be a subtype A2. The results of the sequence comparisons of the BoNT/F gene of *C. botulinum* strain Af 84 and the four known BoNT/F subtypes are presented in Table 7.

TABLE 7

Nucleotide and amino acid identities of BoNT/F among strains representative of the four serotype F subtypes.

| | | % Identity (Nucleotide/amino acid) | | | | |
|---|---|---|---|---|---|---|
| Strain | Neurotoxin subtype | 202 F | Af 84 | Bf 81E-1133 | Bf 3281 | C. baratii 43756 |
| Langeland F | pF[a] | 94/88 | 96/92 | 92/84 | 92/84 | 83/74 |
| 202 F | npF[b] | | 94/87 | 96/90 | 96/90 | 81/70 |
| Af 84 | pF[a] | | | 92/84 | 92/84 | 82/72 |
| Bf 81E-1133 | bvF[c] | | | | 100/100 | 80/69 |
| Bf 3281 | bvF[c] | | | | | 80/69 |
| C. baratii 43756 | F (baratii) | | | | | |

[a]proteolytic F
[b]nonproteolytic F
[c]bivalent F

Although *C. botulinum* strain Af 84 is a bivalent strain, the BoNT/F amino acid sequence differed by 16% from the BoNT/bvF of bivalent strains Bf 3281(32419) and Bf 81E-1133, and it showed the highest level of identity (96/92%) at the nucleotide and amino acid level with the BoNT/pF of proteolytic *C. botulinum* strain Langeland F. Because the toxin differed from the other BoNT/F subtypes by more than 2.6% (Arndt et al., 2006; Smith et al., 2005), it was classified as a new neurotoxin subtype named BoNT/F5.

The amino acid sequences of the BoNT/F subtypes vary more than the subtypes of the other neurotoxin serotypes, ranging from 10-32% identity (Smith et al. 2005). Even though new subtypes are defined by their amino acid sequences differing by 2.6% (Arndt et al. 2006; Smith et al. 2005), the amino acid sequence of BoNT/F of strain Af 84 differs from the other BoNT/F subtypes by at least 8% and thus represents a new subtype BoNT/F5. Despite strain Af 84 being a bivalent strain, BoNT/F5 shared higher homology with the BoNT/pF subtype of *C. botulinum* strain Langeland F rather than the BoNT/bvF subtype of bivalent Bf subtype strains (Table 7). The BoNT/pF gene is located on the chromosome in strain Langeland F (Accession number: CP000728), but toxigenic strains of *C. baratii* have been found to produce BoNT/F (McCroskey et al. 1991; Gimenez et al. 1992; Hall et al. 1985; Harvey et al. 2002). The mechanism of BoNT/F gene cluster transfer to strains of *C. baratii* is unknown at this time, but virulence plasmids carrying the BoNT/F gene cluster may be involved.

Since the BoNT/A3, BoNT/A4 and BoNT/bvF toxin gene clusters exhibit identical gene content and organization, it is unclear whether the entire neurotoxin gene cluster or a region of the cluster is being exchanged between the highly homologous plasmids pCLJ (657Ba), pCLK (Loch Maree) and pBot81E-1133 (Bf 81E-1133). The gene encoding NTNH was targeted for analysis since it has been reported as being chimeric in several proteolytic strains and is suggested to be a hot spot for recombination (Hutson et al. 1996; East et al. 1996; Jovita et al. 1998; Smith et al. 2007). Pairwise comparisons of the amino acid sequence of NTNH of the BoNT/bvF cluster in Bf 81E-1133 with the NTNH of several strains of serotype A, proteolytic and nonproteolytic strains of serotypes B and F, and to serotype E strain Alaska E revealed that it was highly chimeric (data not shown). Four different regions of the BoNT/bvF NTNH of strain Bf 81E-1133 were identified that exhibit a high level of homology to the corresponding NTNH region of five different strains (Table 7). The amino terminal region of NTNH comprising amino acid residues 1-294 exhibited a 99% identity with the corresponding region of NTNH of the BoNT/A4 cluster of strain 657Ba (Table 7). However, the next region comprising 277 amino acid residues (295-572) shared the highest level of homology (89.9%) with the corresponding region of NTNH in the nonproteolytic *C. botulinum* serotype E strain Alaska E. The largest region of NTNH (residues 573-1131) was most identical (96.8%) to the similar region of NTNH of the BoNT/A3 cluster of strain Loch Maree. The C-terminal 36 residues showed the same level of identity (88.0%) with the corresponding residues of both the NTNH of the proteolytic strain Langeland F and that of the nonproteolytic strain 202F.

Results.

Sequence analysis of the BoNT/B and BoNT/F genes of strain Bf 81E-1133 revealed that these genes were identical to the BoNT/bvB and BoNT/bvF of strain Bf 3281(32419) and to the BoNT/bvB of strain 657Ba (Table 6). Identical subtype BoNT genes on highly homologous plasmids in these strains provides strong evidence that plasmids are the likely vehicles for BoNT gene transfer. The location of the BoNT/bvB and BoNT/bvF gene clusters on plasmid, pBot81E-1133 (Bf 81E-1133) was analyzed in relation to the BoNT/bvB and BoNT/pB gene clusters on plasmids pCLJ (657Ba) and pCLD (Okra B), as well as to the BoNT/A3 and BoNT/A4 gene clusters on plasmids pCLK (Loch Maree) and pCLJ (657Ba) to provide insight as to how highly homologous plasmids carry genes encoding neurotoxins of distinct serotypes. The BoNT/bvB gene cluster of pBot81E-1133 is in the same position on the plasmid as the BoNT/bvB and BoNT/pB gene clusters of pCLJ (657Ba) and pCLD (Okra B) (FIG. 15B). Alignment of plasmids pBot81E-1133 (Bf 81E-1133), pCLK (Loch Maree) and pCLJ (657Ba) shows that the BoNT/bvF cluster of strain Bf 81E-1133 is in the same orientation and position as the BoNT/A3 cluster of pCLK and is in opposite orientation to the BoNT/A4 cluster of pCLJ (FIG. 15A). Smith et al. 2007 reported that the BoNT/A4 gene cluster of pCLJ was in opposite orientation to the BoNT/A3 cluster of pCLK, indicating recombination of the entire gene cluster.

Pairwise comparisons of the amino acid sequence of the NTNH of the BoNT/bvF cluster in Bf 81E-1133 with the NTNH of several strains of serotype A, proteolytic and nonproteolytic strains of serotypes B and F, and with serotype E strain Alaska E was performed and revealed four distinct regions (Table 7). The highly chimeric nature of the BoNT/bvF NTNH of strains Bf 81E-1133 and 3281(32419) suggest that the neurotoxin gene and the 3' end of NTNH may be the region of the cluster that is being interchanged between *C. botulinum* virulence plasmids. For example, a region containing a portion of the NTNH gene and the BoNT/bvF gene of pBot81E-1133 may replace a similar region in the BoNT/A4 (pCLJ) or BoNT/A3 (pCLK) gene clusters generating a BoNT/F encoding plasmid.

Nucleotide Sequence Accession Numbers.

The nucleotide sequences of the BoNT/A2 (SEQ ID NO: 70) and BoNT/F5 (SEQ ID NO:71) genes of strain Af 84 presented in this paper were submitted to GenBank and were assigned the Accession Nos. FJ968749 (BoNT/A2 gene) and FJ968748 (BoNT/F5 gene).

It should be noted that the above description, attached figures and their descriptions are intended to be illustrative and not limiting of this invention. Many themes and variations of this invention will be suggested to one skilled in this and, in light of the disclosure. All such themes and variations are within the contemplation hereof. For instance, while this invention has been described in conjunction with the various exemplary embodiments outlined above, various alternatives, modifications, variations, improvements, and/or substantial equivalents, whether known or that rare or may be presently unforeseen, may become apparent to those having at least ordinary skill in the art. Various changes may be made without departing from the spirit and scope of the invention. Therefore, the invention is intended to embrace all known or later-developed alternatives, modifications, variations, improvements, and/or substantial equivalents of these exemplary embodiments.

REFERENCES

Arndt et al. 2006. J. Mol. Biol. 362(4):733-742.
Aureli et al. 1986. J. Infect. Dis. 154:207-211.
Bannan et al. 2007. J. Bacteriol. 188:4942-4951.
Bannam et al. 2006. J Bacteriol. 188: 4942-4951.
Beverley. 1988. Nucleic Acids Res 16: 925-939.
Blaiotta et al. 2000. Lett Appl Microbiol 31:343-348.
Bradshaw et al. 2004. Anaerobe 10: 321-333.
Brynestad et al. 2001. Infect. Immun. 69:3483-3487.
Carter et al. 2009. BMG Genomics
Darling et al. 2004. Genome Res. 14:1394-1403.
Dineen et al. 2000. Appl Environ Microbiol 66: 5480-5483.
Dover et al. 2009. J. Clin. Microbiol.
East et al. 1996. Int. J. Syst. Bacteriol. 46(4):1105-1112.
Eklund et al. 1988. Appl. Environ. Microbiol. 54:1405-1408.
Eklund et al. 1967. J. Bacteriol. 93:1461-1462.
Franciosa et al. 2004. Appl. Environ. Microbiol. 70:7192-7199.
Franciosa et al. 2009. PLoS ONE 4(3): e4829. doi:10.1371/journal.pone.0004829.
Gimenez et al. 1978. Zbl. Bakt. Hyg. 240:215-220.
Gimenez et al. 1983. Rev. Argent. Microbiol. 15:51-55.
Gimenez et al. 1992. Infect. Immun. 60(2):518-522.
Hall et al. 1985. J. Clin. Microbiol. 21(4):654-655.
Harvey et al. 2002. J. Clin. Microbiol. 40(6):2260-2262.
Hatheway. 1990. Clin. Microbiol. Rev. 3:66-98.
Hatheway et al. 1987. J. Clin. Microbiol. 25:2334-2338.
Hatheway et al. 1981. J Clin. Microbiol 14: 607-611.
Hause et al. 1992. FEMS Microbiol. Lett. 99:251-256.
Heap et al. 2010. J. Microbiol. Methods 80:49-55.
Heap et al. 2009. J Microbiol. Methods 78:79-85.
Heap et al. 2004. J Microbiol. Methods 70: 452-464.
Hill et al. 2007. J. Bacteriol. 189:818-832.
Hill et al. 2009. BMC Biol 7: 66.
Hutson et al. 1996. J. Biol. Chem. 271:10786-10792.
Hughes et al. 2007. J. Bacteriol. 189:7531-7538.
Jacobson et al. 2008. Microbiology. 154:2408-2415.
Johnson et al. 2005. J. Clin. Microbiol. 43(6):2602-2607.
Johnson et al. 1997. Clin. Infect. Dis. 25(Suppl2):5168-170.
Jovita et al. 1998. Curr. Microbiol. 36:226-231.
Lin et al. 1991. Appl Environ Microbiol 57: 2946-2950.
Lynt et al. 1982. J. Food Prot. 45:466-474.
Marshall et al. 2007. Biochem. Biophys. Res. Comm. 361: 49-54.
McCroskey et al. 1986. J. Clin. Microbiol. 23:201-202.
McCroskey et al. 1991. J. Clin. Microbiol. 29(11):2618-2620.
Neve et al. 1984. J Bacteriol. 157: 833-838.
Parsons et al. 2007. J. Bacteriol. 189:7782-7790.
Peck et al. 2009. Adv. Microb. Physiol. 55: 183-320.
Raphael et al. 2008. Appl. Environ. Microbiol. 74:4390-4397.
Rood et al. 1978. Plasmid 1: 563-570.
Rood. 2004. Virulence Plasmids of Spore-Forming Bacteria. In: Funnell B E, Phillips J G, eds. Plasmid Biology. Washington D.C.: ASM Press. pp 413-422.

Sakaguchi et al. 2005. Proc. Natl. Acad. Sci. 102(48):17472-17477.
Sambrook et al. 2001. Molecular Cloning—A laboratory manual, 3rd ed. Cold Spring Harbor Laboratory Press, Cold Spring Harbor, N.Y.
Santos-Buelga et al. 1998. Curr. Microbiol. 37:312-318.
Sayeed et al. 2007. Infect Immun 75: 2391-2398.
Schantz et al. 1992. Microbiol. Rev. 56:80-99.
Scott et al. 1978. FEMS Microbiol. Lett. 4:55-58.
Sebaihia et al. 2007. Genome Res. 17:1082-1092.
Smedley et al. 2005. Rev Physiol Biochemi Pharm 152:183-204.
Smith et al. 2005. Infect. Immun. 73(9):5450-5457.
Smith et al. 2007. PLoS ONE 2:e1271. doi:10.1371/journal.pone0001271
Strom et al. 1984. Appl. Environ. Microbiol. 48:956-963.
Umeda et al. 2009. J Clin Microbiol 47: 2720-2728.
Wang et al. 2000. Appl. Environ. Microbiol. 66(11):4992-4997.
Zhou et al. 1993. Appl. Environ. Microbiol. 59(11):3825-3831.
Zhou et al. 1995. Infect. Immun. 63:2087-2091.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09637748B2). An electronic copy of the "Sequence Listing" will also be available from the USPTO upon request and payment of the fee set forth in 37 CFR 1.19(b)(3).

We claim:

1. A method of conjugatively transferring a gene of interest into a recipient *Clostridium* strain, the method comprising
   (a) conjugatively transferring a plasmid comprising
      (i) a native plasmid of a donor *C. botulinum* strain capable of being conjugatively transferred into a recipient *Clostridium* strain, wherein the plasmid comprises a selective marker and wherein the plasmid is selected from the group consisting of pCLJ (SEQ ID NO: 2), pCLL (SEQ ID NO: 3), pBot81E-1133, and pCLD (SEQ ID NO:4); and
      (ii) a nucleotide sequence of a gene of interest capable of being expressed in the recipient *Clostridium* strain, wherein the gene is not native to the donor *C. botulinum* strain,
   wherein the gene of interest is incorporated into the plasmid of the donor *C. botulinum* strain by being operably joined to a promoter effective in *Clostridium* strain, and
   wherein the gene of interest is expressed in the recipient *Clostridium* strains.

2. The method of claim 1, wherein the donor *C. botulinum* strain is selected from *C. botulinum* serotypes A, B, C, D, E, F or G.

3. The method of claim 1, wherein the donor *C. botulinum* strain is selected from *C. botulinum* strains Ba, Ab, Bf, Af or A(B).

4. The method of claim 1, wherein the gene of interest is a gene for expressing clostridial toxins, toxin fragments, or antigenic portions thereof.

5. The method of claim 1, wherein the promoter is a NTNH promoter.

6. The method of claim 1, wherein the donor *Clostridium* strain and the recipient *Clostridium* strain are the same species.

7. A method of conjugatively transferring a gene of interest into a recipient *Clostridium* strain, the method comprising conjugatively transferring a plasmid comprising
   (i) a native plasmid of a donor *C. botulinum* strain capable of being conjugatively transferred into a recipient *Clostridium* strain, wherein the plasmid comprises a selective marker and wherein the plasmid is selected from the group consisting of pBotCDC-A3 (SEQ ID NO: 1), pCLJ (SEQ ID NO: 2), pCLL (SEQ ID NO: 3), pBot81E-1133, and pCLD (SEQ ID NO:4), and
   (ii) a nucleotide sequence of a gene of interest capable of being expressed in the recipient *Clostridium* strain, wherein the gene is not native to the donor *C. botulinum* strain,
   wherein the gene of interest is incorporated into the plasmid of the donor *C. botulinum* strain by being operably joined to a promoter effective in *Clostridium* strains, wherein the gene of interest is expressed in the recipient *Clostridium* strain, and wherein the donor *Clostridium* strain and the recipient *Clostridium* strain are different species.

8. A method of conjugatively transferring a gene of interest into a recipient *Clostridium* strain, the method comprising conjugatively transferring a plasmid comprising
   (i) a native plasmid of a donor *C. botulinum* strain capable of being conjugatively transferred into a recipient *Clostridium* strain, wherein the plasmid comprises a selective marker and wherein the plasmid is selected from the group consisting of pBotCDC-A3 (SEQ ID NO: 1), pCLJ (SEQ ID NO: 2), pCLL (SEQ ID NO: 3), pBot81E-1133, and pCLD (SEQ ID NO:4), and
   (ii) a nucleotide sequence of a gene of interest capable of being expressed in the recipient *Clostridium* strain, wherein the gene is not native to the donor *C. botulinum* strain,
   wherein the gene of interest is incorporated into the plasmid of the donor *C. botulinum* strain by being operably joined to a promoter effective in *Clostridium* strains, wherein the gene of interest is expressed in the recipient *Clostridium* strain, and wherein the recipient *Clostridium* strain is toxic.

9. A method of conjugatively transferring a gene of interest into a recipient *Clostridium* strain, the method comprising conjugatively transferring a plasmid comprising
   (i) a native plasmid of a donor *C. botulinum* strain capable of being conjugatively transferred into a recipient

*Clostridium* strain, wherein the plasmid comprises a selective marker and wherein the plasmid is selected from the group consisting of pBotCDC-A3 (SEQ ID NO: 1), pCLJ (SEQ ID NO: 2), pCLL (SEQ ID NO: 3), pBot81E-1133, and pCLD (SEQ ID NO:4), and (ii) a nucleotide sequence of a gene of interest capable of being expressed in the recipient *Clostridium* strain, wherein the gene is not native to the donor *C. botulinum* strain, wherein the gene of interest is incorporated into the plasmid of the donor *C. botulinum* strain by being operably joined to a promoter effective in *Clostridium* strains, wherein the gene of interest is expressed in the recipient *Clostridium* strain, and wherein the recipient *Clostridium* strain is proteolytic.

10. The method of claim 1 wherein the recipient *Clostridium* strain is LNT01 or Hall A-Hyper.

11. The method of claim 1 wherein the plasmid that is conjugative transferred is larger than 150 kb.

12. The method of claim 1 wherein the conjugative transfer plasmid is further genetically tagged with an antibiotic resistance gene for conferring resistance to erythromycin, tetracycline, chloramphenicol or thiamphenicol.

13. The method of claim 1 wherein the recipient *Clostridium* strain is nontoxic.

14. The method of claim 1 wherein the recipient *Clostridium* strain is nonproteolytic.

\* \* \* \* \*

UNITED STATES PATENT AND TRADEMARK OFFICE
CERTIFICATE OF CORRECTION

PATENT NO. : 9,637,748 B2  
APPLICATION NO. : 14/096584  
DATED : May 2, 2017  
INVENTOR(S) : Eric A. Johnson et al.

Page 1 of 1

It is certified that error appears in the above-identified patent and that said Letters Patent is hereby corrected as shown below:

In the Specification

Column 7, Line 10, "Nan" should be --NarI--.

Column 8, Line 18, "NnuI" should be --NruI--.

Column 8, Line 18, "RsnII" should be --RsrII--.

Column 34, Line 35, "NnuI" should be --NruI--.

Column 34, Line 35, "RsnII" should be --RsrII--.

Column 34, Line 35-36, "SalI, SfiI" should be --SalI, SbfI, SfiI--.

Column 44, Line 50, "5168" should be --S168--.

Signed and Sealed this  
Twentieth Day of November, 2018

Andrei Iancu  
*Director of the United States Patent and Trademark Office*